US010376654B2

(12) United States Patent
Sanders et al.

(10) Patent No.: US 10,376,654 B2
(45) Date of Patent: Aug. 13, 2019

(54) SYSTEM FOR CLOSED TRANSFER OF FLUIDS AND MEMBRANE ARRANGEMENTS FOR USE THEREOF

(71) Applicant: Becton Dickinson and Company Limited, Dun Laoghaire (IE)

(72) Inventors: Laurie Sanders, Glen Ridge, NJ (US); Yan Yevmenenko, New York, NY (US); Jude Cancellieri, Oakland, NJ (US); Olaf Garcia Pohl, Madrid (ES)

(73) Assignee: Becton Dickinson and Company Limited, Dun Laoghaire (IE)

( * ) Notice: Subject to any disclaimer, the term of this patent is extended or adjusted under 35 U.S.C. 154(b) by 166 days.

(21) Appl. No.: 14/691,922

(22) Filed: Apr. 21, 2015

(65) Prior Publication Data

US 2015/0297839 A1 Oct. 22, 2015

Related U.S. Application Data

(60) Provisional application No. 61/982,061, filed on Apr. 21, 2014.

(51) Int. Cl.
*A61M 5/34* (2006.01)
*A61J 1/14* (2006.01)
(Continued)

(52) U.S. Cl.
CPC .............. *A61M 5/34* (2013.01); *A61J 1/1406* (2013.01); *A61J 1/2055* (2015.05); *A61J 1/2096* (2013.01);
(Continued)

(58) Field of Classification Search
CPC ............ A61M 2005/3103; A61M 5/34; A61M 2039/1077; A61M 2039/1083;
(Continued)

(56) References Cited

U.S. PATENT DOCUMENTS

| 4,436,125 A | 3/1984 | Blenkush |
| 4,564,054 A | 1/1986 | Gustavsson |

(Continued)

FOREIGN PATENT DOCUMENTS

| EP | 2462971 A1 | 6/2012 |
| WO | 02076374 A1 | 10/2002 |

(Continued)

*Primary Examiner* — Quynh-Nhu H. Vu
(74) *Attorney, Agent, or Firm* — The Webb Law Firm

(57) ABSTRACT

A syringe adapter includes a housing having a first end and a second end with the first end configured to be secured to a first container, a cannula having a first end and a second end with the second end of the cannula positioned within the housing, and a collet having a first end and a second end. At least a portion of the collet is received within the housing. The collet includes a body defining a passageway, a membrane received by the passageway, and a locking member connected to the body of the collet. The membrane has a body with a first end and a second end. The body of the membrane defines a passageway. The collet is movable from a first position where the locking member is open to receive a mating connector to a second position where radially outward movement of the locking member is restricted.

19 Claims, 62 Drawing Sheets

(51) Int. Cl.
*A61J 1/20* (2006.01)
*A61M 5/31* (2006.01)

(52) U.S. Cl.
CPC .............. *A61J 1/201* (2015.05); *A61J 1/2065* (2015.05); *A61M 2005/3103* (2013.01)

(58) Field of Classification Search
CPC ............ A61M 2039/1088; A61J 1/1406; A61J 1/201; A61J 1/2055; A61J 1/2065; A61J 1/2096
See application file for complete search history.

(56) References Cited

U.S. PATENT DOCUMENTS

| | | |
|---|---|---|
| 4,673,404 A | 6/1987 | Gustavsson |
| 4,932,937 A | 6/1990 | Gustavsson et al. |
| 5,052,725 A | 10/1991 | Meyer et al. |
| 5,104,158 A | 4/1992 | Meyer et al. |
| 5,122,129 A | 6/1992 | Olson et al. |
| 5,280,876 A | 1/1994 | Atkins |
| 5,290,254 A | 3/1994 | Vaillancourt |
| 5,322,518 A | 6/1994 | Schneider et al. |
| 5,334,188 A | 8/1994 | Inoue et al. |
| 5,360,011 A | 11/1994 | McCallister |
| 5,395,348 A | 3/1995 | Ryan |
| 5,437,650 A | 8/1995 | Larkin et al. |
| 5,464,123 A | 11/1995 | Scarrow |
| 5,472,430 A | 12/1995 | Vaillancourt et al. |
| 5,478,328 A | 12/1995 | Silverman et al. |
| 5,487,728 A | 1/1996 | Vaillancourt |
| 5,492,147 A * | 2/1996 | Challender ............ F16L 29/005 137/614.05 |
| 5,507,733 A | 4/1996 | Larkin et al. |
| 5,509,911 A | 4/1996 | Cottone, Sr. et al. |
| 5,545,152 A | 8/1996 | Funderburk et al. |
| 5,607,392 A | 3/1997 | Kanner |
| 5,609,584 A | 3/1997 | Gettig et al. |
| 5,611,792 A | 3/1997 | Gustafsson |
| 5,647,845 A | 7/1997 | Haber et al. |
| 5,685,866 A | 11/1997 | Lopez |
| 5,807,347 A | 9/1998 | Bonaldo |
| 5,879,345 A * | 3/1999 | Aneas .................... A61J 1/2089 215/277 |
| 5,897,526 A | 4/1999 | Vaillancourt |
| 6,063,068 A | 5/2000 | Fowles et al. |
| 6,089,541 A | 7/2000 | Weinheimer et al. |
| 6,113,583 A | 9/2000 | Fowles et al. |
| 6,132,404 A | 10/2000 | Lopez |
| 6,139,534 A | 10/2000 | Niedospial, Jr. et al. |
| 6,221,041 B1 | 4/2001 | Russo |
| 6,221,056 B1 | 4/2001 | Silverman |
| 6,343,629 B1 | 2/2002 | Wessman et al. |
| 6,358,236 B1 | 3/2002 | DeFoggi et al. |
| 6,409,708 B1 | 6/2002 | Wessman |
| 6,474,375 B2 | 11/2002 | Spero et al. |
| 6,478,788 B1 | 11/2002 | Aneas |
| 6,544,246 B1 | 4/2003 | Niedospial, Jr. |
| 6,551,299 B2 | 4/2003 | Miyoshi et al. |
| 6,585,695 B1 * | 7/2003 | Adair .................... A61M 5/162 604/183 |
| 6,599,273 B1 | 7/2003 | Lopez |
| 6,610,040 B1 | 8/2003 | Fowles et al. |
| 6,629,958 B1 | 10/2003 | Spinello |
| 6,656,433 B2 | 12/2003 | Sasso |
| 6,715,520 B2 | 4/2004 | Andreasson et al. |
| 6,814,726 B1 | 11/2004 | Lauer |
| 6,852,103 B2 | 2/2005 | Fowles et al. |
| 6,875,203 B1 | 4/2005 | Fowles et al. |
| 6,875,205 B2 | 4/2005 | Leinsing |
| 6,911,025 B2 | 6/2005 | Miyahara |
| 6,997,917 B2 | 2/2006 | Niedospial, Jr. et al. |
| 7,040,598 B2 | 5/2006 | Raybuck |
| 7,083,605 B2 | 8/2006 | Miyahara |
| 7,097,209 B2 | 8/2006 | Unger et al. |
| 7,261,707 B2 | 8/2007 | Frezza et al. |
| 7,306,584 B2 | 12/2007 | Wessman et al. |
| 7,326,194 B2 | 2/2008 | Zinger et al. |
| 7,350,535 B2 | 4/2008 | Liepold et al. |
| 7,354,427 B2 | 4/2008 | Fangrow |
| 7,452,349 B2 | 11/2008 | Miyahara |
| 7,547,300 B2 | 6/2009 | Fangrow |
| 7,628,772 B2 | 12/2009 | McConnell et al. |
| 7,648,491 B2 | 1/2010 | Rogers |
| 7,658,734 B2 | 2/2010 | Adair et al. |
| 7,743,799 B2 | 6/2010 | Mosler et al. |
| 7,744,581 B2 | 6/2010 | Wallen et al. |
| 7,758,560 B2 | 7/2010 | Connell et al. |
| 7,803,140 B2 | 9/2010 | Fangrow, Jr. |
| 7,857,805 B2 | 12/2010 | Raines |
| 7,867,215 B2 | 1/2011 | Akerlund et al. |
| 7,879,018 B2 | 2/2011 | Zinger et al. |
| 7,900,659 B2 | 3/2011 | Whitley et al. |
| 7,927,316 B2 | 4/2011 | Proulx et al. |
| 7,942,860 B2 | 5/2011 | Horppu |
| 7,975,733 B2 | 7/2011 | Horppu et al. |
| 8,096,525 B2 | 1/2012 | Ryan |
| 8,122,923 B2 | 2/2012 | Kraus et al. |
| 8,123,738 B2 | 2/2012 | Vaillancourt |
| 8,137,332 B2 | 3/2012 | Pipelka |
| 8,167,863 B2 | 5/2012 | Yow |
| 8,177,768 B2 | 5/2012 | Leinsing |
| 8,196,614 B2 | 6/2012 | Kriheli |
| 8,206,367 B2 | 6/2012 | Warren et al. |
| 8,211,069 B2 | 7/2012 | Fangrow, Jr. |
| 8,225,826 B2 | 7/2012 | Horppu et al. |
| 8,226,628 B2 | 7/2012 | Muramatsu et al. |
| 8,257,286 B2 | 9/2012 | Meyer et al. |
| 8,267,127 B2 | 9/2012 | Kriheli |
| 8,277,424 B2 * | 10/2012 | Pan ........................ A61M 39/26 604/249 |
| 8,287,513 B2 * | 10/2012 | Ellstrom ................ A61M 39/10 141/319 |
| 8,317,741 B2 | 11/2012 | Kraushaar |
| 8,317,743 B2 | 11/2012 | Denenburg |
| 8,398,607 B2 | 3/2013 | Fangrow, Jr. |
| 8,403,905 B2 | 3/2013 | Yow |
| 8,425,487 B2 | 4/2013 | Beiriger et al. |
| 8,449,521 B2 | 5/2013 | Thorne, Jr. et al. |
| 8,454,579 B2 | 6/2013 | Fangrow, Jr. |
| 8,900,212 B2 * | 12/2014 | Kubo .................... A61J 1/2096 604/403 |
| 9,724,269 B2 * | 8/2017 | Sjogren ................ A61J 1/2096 |
| 2003/0070726 A1 | 4/2003 | Andreasson et al. |
| 2004/0116892 A1 | 6/2004 | Burroughs et al. |
| 2005/0065495 A1 | 3/2005 | Zambaux |
| 2005/0182383 A1 | 8/2005 | Wallen |
| 2005/0215976 A1 | 9/2005 | Wallen |
| 2007/0079894 A1 | 4/2007 | Kraus et al. |
| 2008/0045919 A1 | 2/2008 | Jakob et al. |
| 2008/0287914 A1 | 11/2008 | Wyatt et al. |
| 2009/0159485 A1 | 6/2009 | Jakob et al. |
| 2010/0179506 A1 | 7/2010 | Shemesh et al. |
| 2010/0217226 A1 | 8/2010 | Shemesh |
| 2011/0004183 A1 | 1/2011 | Carrez et al. |
| 2011/0062703 A1 | 3/2011 | Lopez et al. |
| 2011/0074148 A1 * | 3/2011 | Imai ..................... A61J 1/2089 285/308 |
| 2011/0106046 A1 * | 5/2011 | Hiranuma ............. A61J 1/2096 604/414 |
| 2011/0257621 A1 | 10/2011 | Fangrow |
| 2011/0291406 A1 | 12/2011 | Kraft et al. |
| 2012/0035580 A1 | 2/2012 | Fangrow |
| 2012/0046636 A1 | 2/2012 | Kriheli |
| 2012/0123381 A1 | 5/2012 | Kraus et al. |
| 2012/0184938 A1 | 7/2012 | Lev et al. |
| 2012/0192968 A1 | 8/2012 | Bonnal et al. |
| 2012/0192976 A1 | 8/2012 | Rahimy et al. |
| 2012/0203193 A1 | 8/2012 | Rogers |
| 2012/0215183 A1 | 8/2012 | Halili et al. |
| 2012/0265163 A1 | 10/2012 | Cheng et al. |
| 2012/0279884 A1 | 11/2012 | Tennican et al. |
| 2012/0316536 A1 * | 12/2012 | Carrez ............... A61M 39/1011 604/535 |

(56) References Cited

U.S. PATENT DOCUMENTS

| | | |
|---|---|---|
| 2013/0006211 A1 | 1/2013 | Takemoto |
| 2013/0012908 A1 | 1/2013 | Yeung |
| 2013/0066293 A1 | 3/2013 | Garfield et al. |
| 2013/0072893 A1 | 3/2013 | Takemoto |
| 2013/0076019 A1 | 3/2013 | Takemoto |
| 2013/0079744 A1 | 3/2013 | Okiyama et al. |
| 2015/0297454 A1* | 10/2015 | Sanders ................ A61J 1/2048 604/414 |

FOREIGN PATENT DOCUMENTS

| | | |
|---|---|---|
| WO | 2005011781 A1 | 2/2005 |
| WO | 2006103074 A1 | 10/2006 |
| WO | 2009024807 A1 | 2/2009 |
| WO | 2009090627 A1 | 7/2009 |
| WO | 2011039747 A1 | 4/2011 |
| WO | 2011050333 A1 | 4/2011 |
| WO | 2012069401 A1 | 5/2012 |
| WO | 2012115911 A2 | 8/2012 |
| WO | 2012117648 A1 | 9/2012 |
| WO | 2012119225 A1 | 9/2012 |
| WO | 2012168235 A1 | 12/2012 |
| WO | 2013025946 A1 | 2/2013 |
| WO | 2013054323 A1 | 4/2013 |
| WO | 2013066779 A1 | 5/2013 |
| WO | 2013115730 A1 | 8/2013 |
| WO | 2013179596 A1 | 12/2013 |
| WO | 2014122643 A1 | 8/2014 |
| WO | 2014181320 A1 | 11/2014 |

\* cited by examiner

SYSTEM FOR CLOSED TRANSFER OF FLUIDS AND MEMBRANE ARRANGEMENTS FOR USE THEREOF

CROSS-REFERENCE TO RELATED APPLICATION

This application claims priority to U.S. Provisional Application Ser. No. 61/982,061, filed Apr. 21, 2014, which is hereby incorporated by reference in its entirety.

BACKGROUND OF THE INVENTION

1. Field of the Disclosure

The present disclosure relates generally to a system for the closed transfer of fluids. More particularly, the present disclosure relates to a system that provides leak-proof sealing during fluid transfer from a first container to a second container and membrane arrangements for use with such a system.

2. Description of the Related Art

Health care providers reconstituting, transporting, and administering hazardous drugs, such as cancer treatments, can put themselves at risk of exposure to these medications and present a major hazard in the health care environment. For example, nurses treating cancer patients risk being exposed to chemotherapy drugs and their toxic effects. Unintentional chemotherapy exposure can affect the nervous system, impair the reproductive system, and bring an increased risk of developing blood cancers in the future. In order to reduce the risk of health care providers being exposed to toxic drugs, the closed transfer of these drugs becomes important.

Some drugs must be dissolved or diluted before they are administered, which involves transferring a solvent from one container to a sealed vial containing the drug in powder or liquid form, by means of a needle. Drugs may be inadvertently released into the atmosphere in gas form or by way of aerosolization, during the withdrawal of the needle from the vial and while the needle is inside the vial if any pressure differential between the interior of the vial and the surrounding atmosphere exists.

SUMMARY OF THE INVENTION

In one aspect, a syringe adapter includes a housing having a first end and a second end with the first end configured to be secured to a first container, a cannula having a first end and a second end with the second end of the cannula positioned within the housing, and a collet having a first end and a second end. At least a portion of the collet is received within the housing. The collet includes a body defining a passageway, a membrane received by the passageway, and a locking member connected to the body of the collet. The membrane has a body with a first end and a second end. The body of the membrane defines a passageway. The collet is movable from a first position where the locking member is open to receive a mating connector to a second position where radially outward movement of the locking member is restricted.

The passageway of the membrane may extend from the first end of the body of the membrane towards the second end of the body of the membrane. The passageway may terminate at a position intermediate the first and second ends of the body of the membrane. The membrane may include a first head portion and a second head portion. The first head portion of the membrane may be positioned within the passageway of the collet, and the second head portion may be engaged with an end of the body of the collet. The first head portion may include a frusto-conical surface and the second head portion may include a convex surface. The first end of the collet may define a counterbore with the first head portion of the membrane engaging the collet and positioned within the counterbore. At least a portion of at least one of the cannula and the membrane may include a lubricant configured to reduce friction between the cannula and the membrane.

In a further aspect, a system for closed transfer of fluids includes a syringe adapter including a housing having a first end and a second end with the first end configured to be secured to a first container, a cannula having a first end and a second end with the second end positioned within the housing, and a collet having a first end and a second end. At least a portion of the collet is received within the housing. The collet includes a body defining a passageway, a first membrane, and a locking member connected to the body. The first membrane includes a body having a first end and a second end with the body of the first membrane defining a passageway. The collet is movable from a first position where the locking member is open to receive a mating connector to a second position where radially outward movement of the locking member is restricted. The system further includes a second component comprising a second membrane and a collet interface surface configured to receive and engage the locking member of the collet.

The second membrane may include a body having a first end and a second end with the first end of the body of the second membrane having a convex surface configured to engage the second end of the first membrane. The second component may include a membrane seat that receives the second membrane.

In a further aspect of the invention, a syringe adapter includes a housing having a first end and a second end with the first end configured to be secured to a first container, a cannula having a first end and a second end with the second end of the cannula positioned within the housing, and a collet having a first end and a second end with at least a portion of the collet received within the housing. The collet including a body defining a passageway, a membrane received by the passageway, and a locking member connected to the body of the collet. The membrane includes a body having a first end and a second end with the body of the membrane including a first head portion and a second head portion. The first and second head portions extend radially outward from the body. The first head portion of the membrane includes a frusto-conical surface and the second head portion of the membrane includes a convex surface. The collet is movable from a first position where the locking member is open to receive a mating connector to a second position where radially outward movement of the locking member is restricted.

The body of the membrane may a passageway extending from the first end of the body of the membrane towards the second end of the body of the membrane.

The passageway may terminate at a position intermediate the first and second ends of the body of the membrane.

BRIEF DESCRIPTION OF THE DRAWINGS

The above-mentioned and other features and advantages of this disclosure, and the manner of attaining them, will become more apparent and the disclosure itself will be better understood by reference to the following descriptions of aspects of the disclosure taken in conjunction with the accompanying drawings, wherein.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

Figure 1:
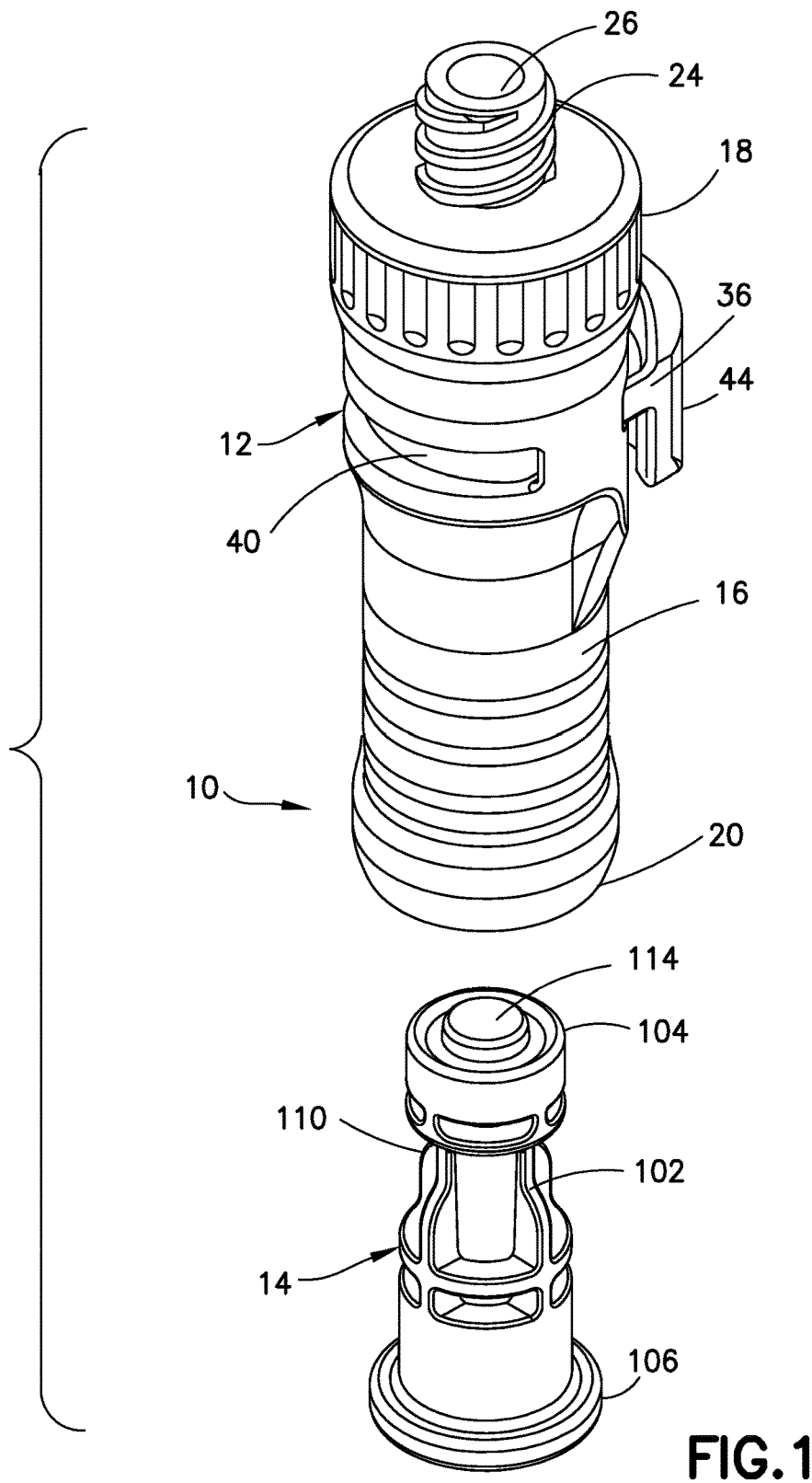
FIG. 1 is a perspective view of a system according to one aspect of the present invention.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

Referring to FIG. 1, one aspect of a system 10 for the closed transfer of fluids includes a syringe adapter 12 and a patient connector 14. The system 10 provides substantially leak-proof sealing during transfer of a fluid from a first container (not shown), such as a vial, to a second container (not shown), such as a syringe, IV bag, or patient IV line. The leak-proof sealing of the system 10 substantially prevents leakage of both air and liquid during use of the system 10. Although not shown, the system 10 may further include a vial adapter, pressure equalization device, or IV bag adapter, as well as other components typically utilized in closed system transfer devices, such as infusion lines and extension sets.

Referring to FIGS. 2-14, one aspect of the syringe adapter 12 includes a housing 16 having a first end 18 and a second end 20 and defining interior space 22. The first end 18 of the housing 16 of the syringe adapter 12 includes a syringe attachment 24, such as a female luer connector, that defines a passageway 26. Although a female luer connector is shown for connection with a corresponding male luer connector of a syringe (not shown), other suitable connection arrangements may be utilized for connection to a syringe, container, or any other medical device. The syringe attachment 24 is secured to the first end 18 of the housing 16 via a threaded connection, although any other suitable connection may be utilized. A cannula 28 having a distal end 30 is secured to the syringe attachment 24 and in fluid communication with the passageway 26 of the syringe attachment 24. The syringe adapter 12 further includes a seal arrangement positioned within the housing 16 of the syringe adapter 12. The seal arrangement includes a collet 32 that receives a first membrane 34. The collet 32 is configured to move within the interior space 22 of the housing 16 of the syringe adapter 12 as discussed in more detail below. The housing 16 of the syringe adapter 12 may include structure to enhance gripping of the syringe adapter 12 by a user. Additional or alternative grip structures and surfaces may be provided to assist a user in gripping the body of the syringe adapter 12.

Referring to FIGS. 2-8, the syringe adapter 12 includes a first connection interface 36 positioned intermediate the first and second ends 18, 20 of the housing 16 of the syringe adapter 12 that includes a lock member 38 that is received within a transverse opening 40 in the housing 16 of the syringe adapter 12. The lock member 38 is configured to move between a closed position and an open position. The lock member 38 defines a central opening 42 and includes a button 44 that is configured to be engaged by a hand of a user or operator of the syringe adapter 12. The lock member 38 further includes a cantilever spring 46 that extends in a longitudinal direction of the syringe adapter 12. The lock member 38 is configured to engage a cam surface that extends radially outward from the housing 16 of the syringe adapter 12. In particular, the lock member 38 is configured to be provided in the closed position, where a portion of the lock member 38 adjacent to the central opening 42 of the lock member 38 is positioned within the interior space 22 of the syringe adapter 12 when no external forces are applied to the lock member 38. When the lock member 38 is moved to the open position where the central opening 42 of the lock member 38 is aligned with the interior space 22 of the syringe adapter 12 or does not create an interference or barrier to objects being inserted into the interior space 22, the cantilever spring 46 engages the cam surface to create a biasing force that urges the lock member 38 back towards the closed position. Accordingly, when the lock member 38 is moved to the open position, the lock member 38 will be urged back to the closed position when the external force acting on the lock member 38 is released. Although the lock member 38 is shown with the cantilever spring 46, any other suitable biasing member may be provided including, but not limited to, compression springs, extension springs, elastomeric material, etc.

Figure 2:
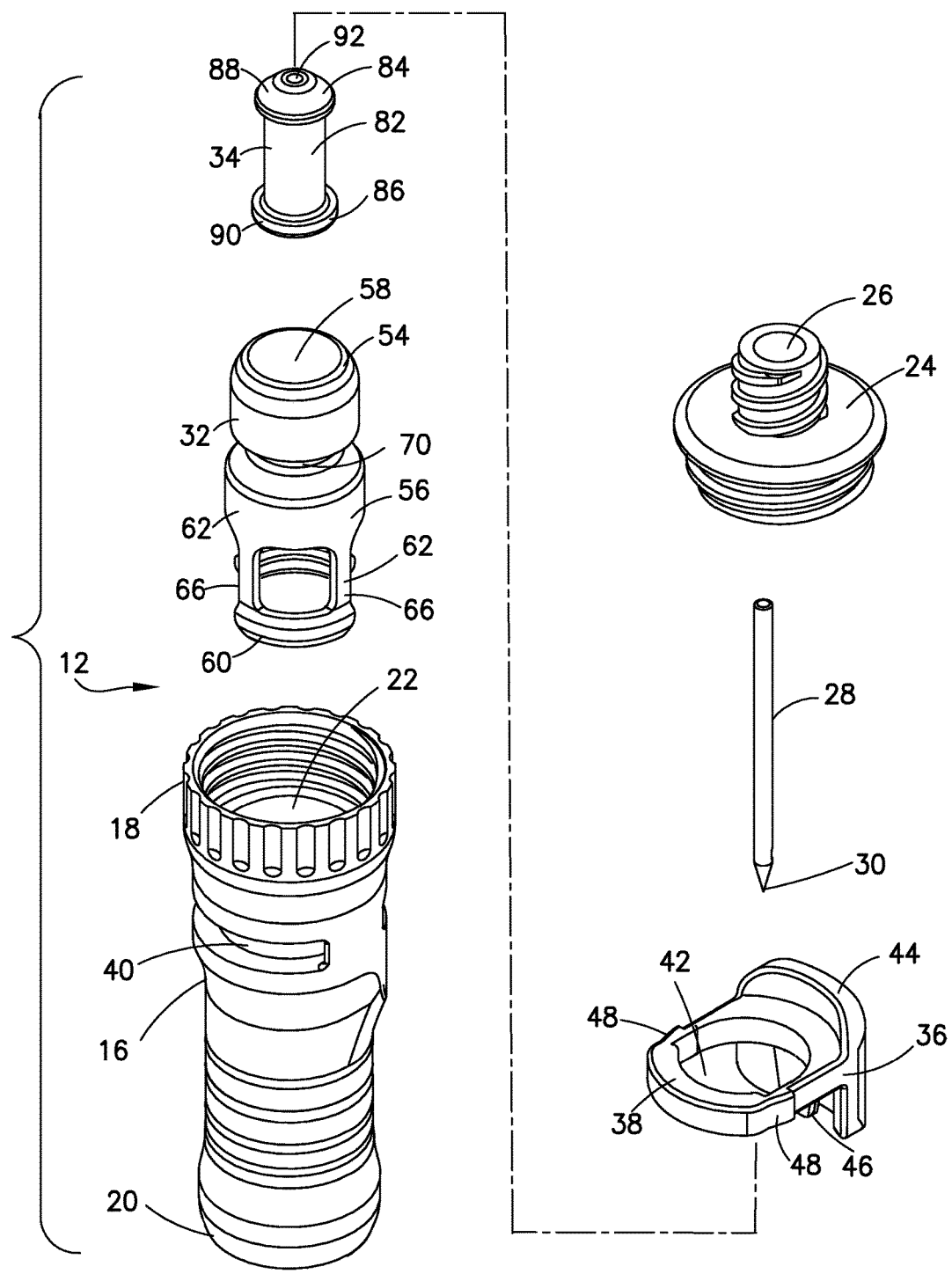
FIG. 2 is an exploded, perspective view of a syringe adapter of the system of FIG. 1 according to one aspect of the present invention.
Figure 3:
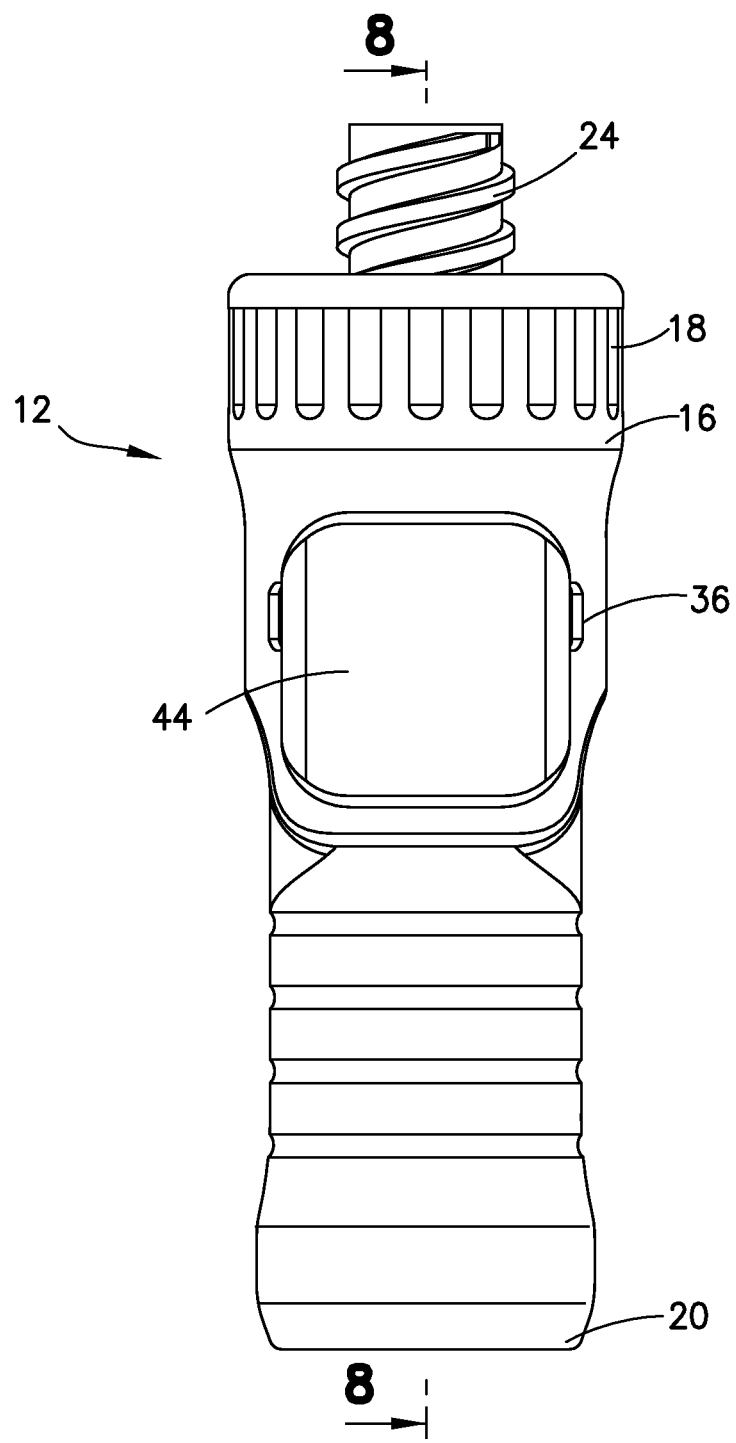
FIG. 3 is a front view of the syringe adapter of FIG. 2 according to one aspect of the present invention.
Figure 4:
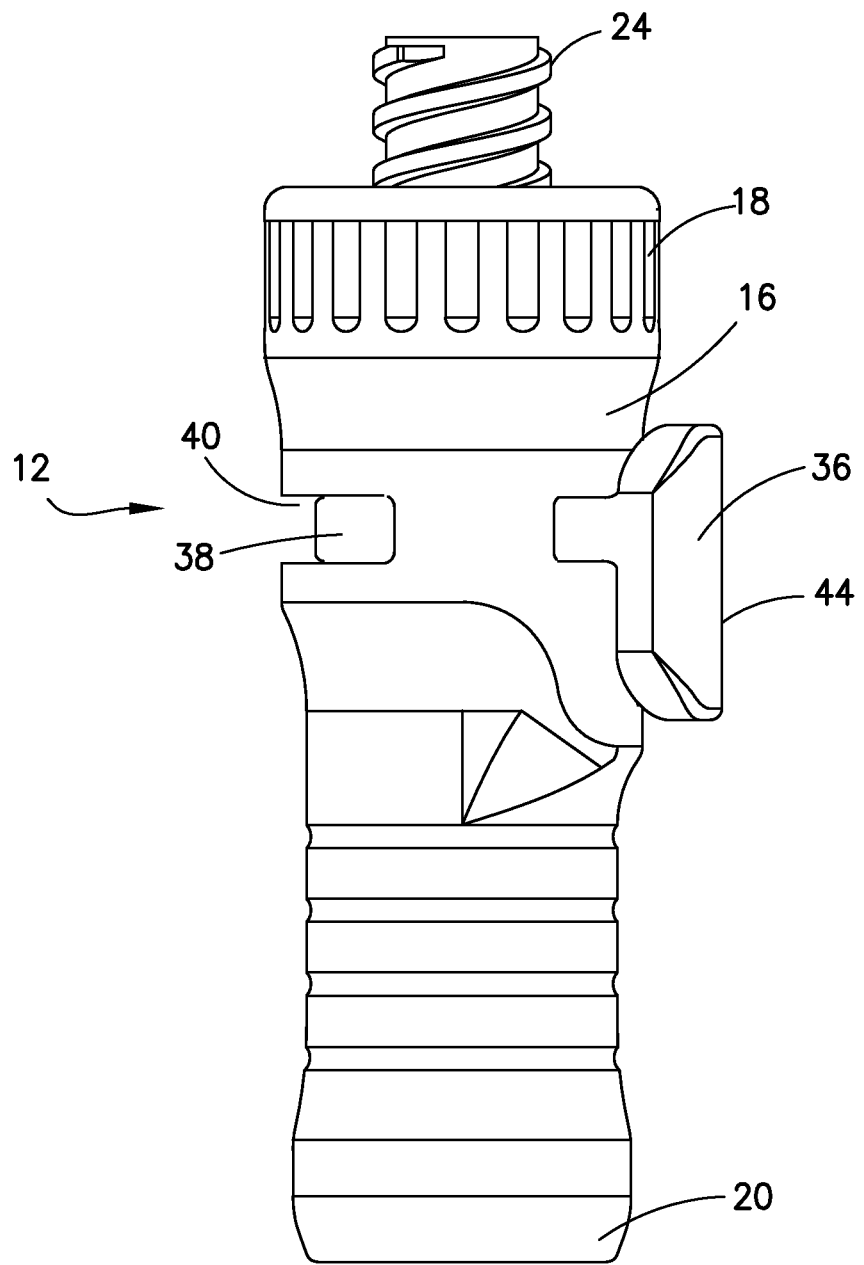
FIG. 4 is a left side view of the syringe adapter of FIG. 2 according to one aspect of the present invention.
Figure 5:
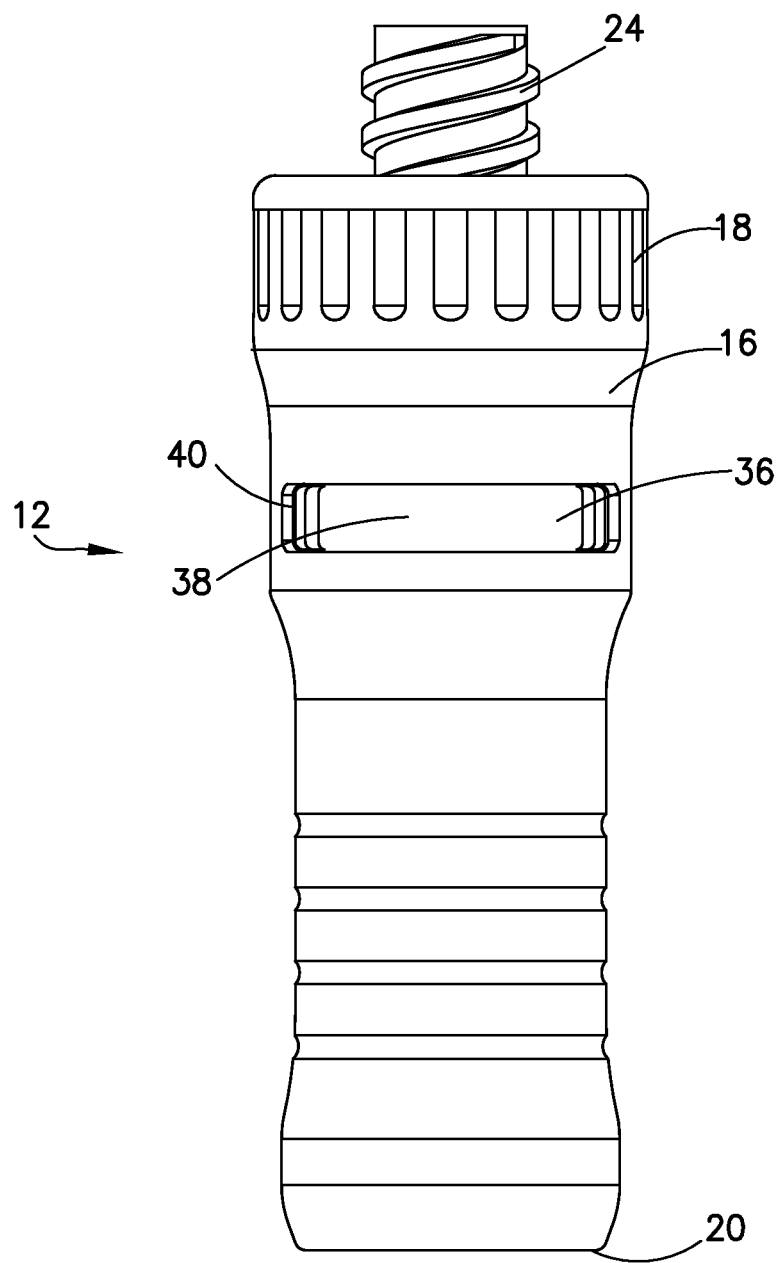
FIG. 5 is a rear view of the syringe adapter of FIG. 2 according to one aspect of the present invention.
Figure 6:
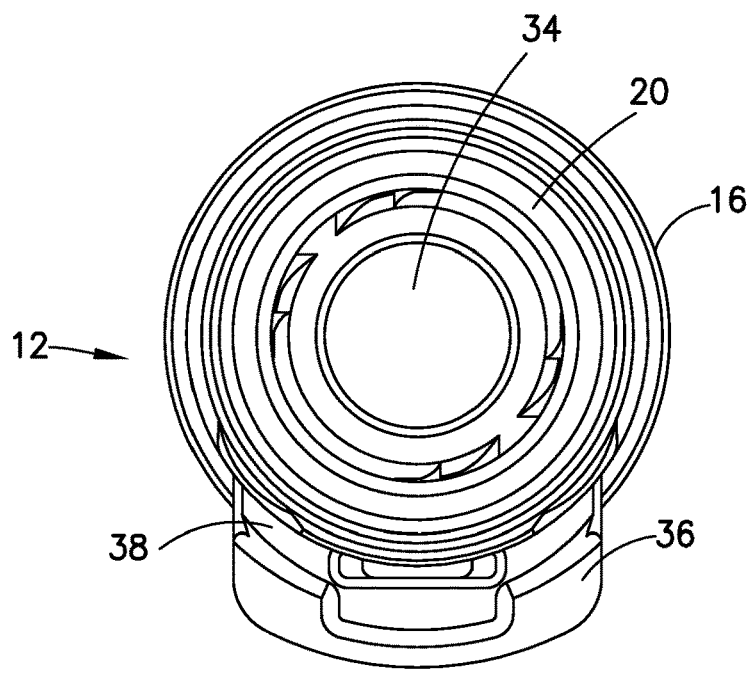
FIG. 6 is a top view of the syringe adapter of FIG. 2 according to one aspect of the present invention.
Figure 7:
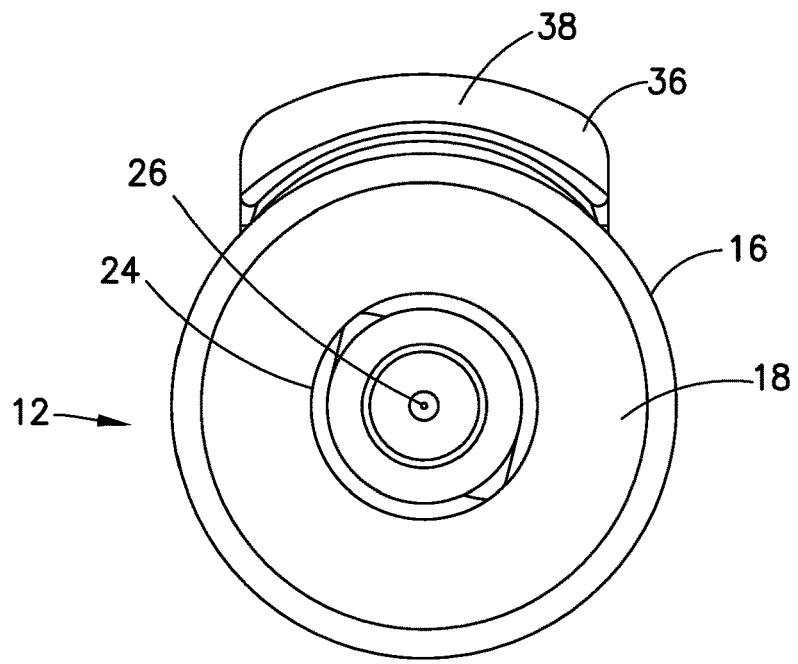
FIG. 7 is a bottom view of the syringe adapter of FIG. 2 according to one aspect of the present invention.

Referring to FIG. 2, the lock member 38 further includes a pair of projections 48 that extend radially outward from the lock member 38. The pair of projections 48 is configured to engage corresponding projections provided on the housing 16 of the syringe adapter 12 to retain the lock member 38 to the housing 16 of the syringe adapter 12. In other words, the projections 48 of the lock member 38 are configured to engage the projections of the housing 16 of the syringe adapter 12 to prevent the lock member 38 from being disconnected and removed from the transverse opening 40 of the housing 16 of the syringe adapter 12.

Referring to FIGS. 8-11, the collet 32 has a body 52 with a first end 54 and a second end 56. The body 52 defines a passageway 58 that extends through the body 52. The body 52 is generally cylindrical, although other suitable shaped collets may be utilized. The collet 32 further includes a locking member 60 connected to the body 52 of the collet 32. As discussed in more detail below, the collet 32 is movable from a first position where the locking member 60 is open to receive a mating connector (shown in FIG. 18), such as the patient connector 14, to a second position where radially outward movement of the locking member 60 is restricted. The locking member 60 is connected to the body 52 via a plurality of arms 62. The locking member 60 is arcuate and resilient as a result of the connection of the locking member 60 to the body 52 via the plurality of arms 62. More specifically, the plurality of arms 62 are flexible and allow the locking member 60 to expand radially outward or radially inward. In one aspect, the locking member 60 is configured to expand radially outward when a mating connector, such as the patient connector 14, is inserted into the locking member 60 and subsequently moving radially inward as the collet 32 is transitioned from the first position to the second position. Alternatively, the locking member 60 may not move radially inward or outward when a mating connector, such as the patient connector 14, is inserted into the locking member 60 and may subsequently move radially inward as the collet 32 is transitioned from the first position to the second position. The second end 20 of the housing 16 of the syringe adapter 12 defines an annular recess 64 adjacent to the interior space 22 that receives the locking member 60 when the collet 32 is in the first position. The annular recess 64 of the housing 16 provides the space for the locking member 60 to expand radially outward. When the collet 32 is transitioned from the first position to the second position, the collet 32 moves axially toward the first end 18 of the syringe adapter 12 with the locking member 60 being biased radially inward due to the engagement of the locking member 60 with the housing 16 of the syringe adapter 12.

Figure 9:
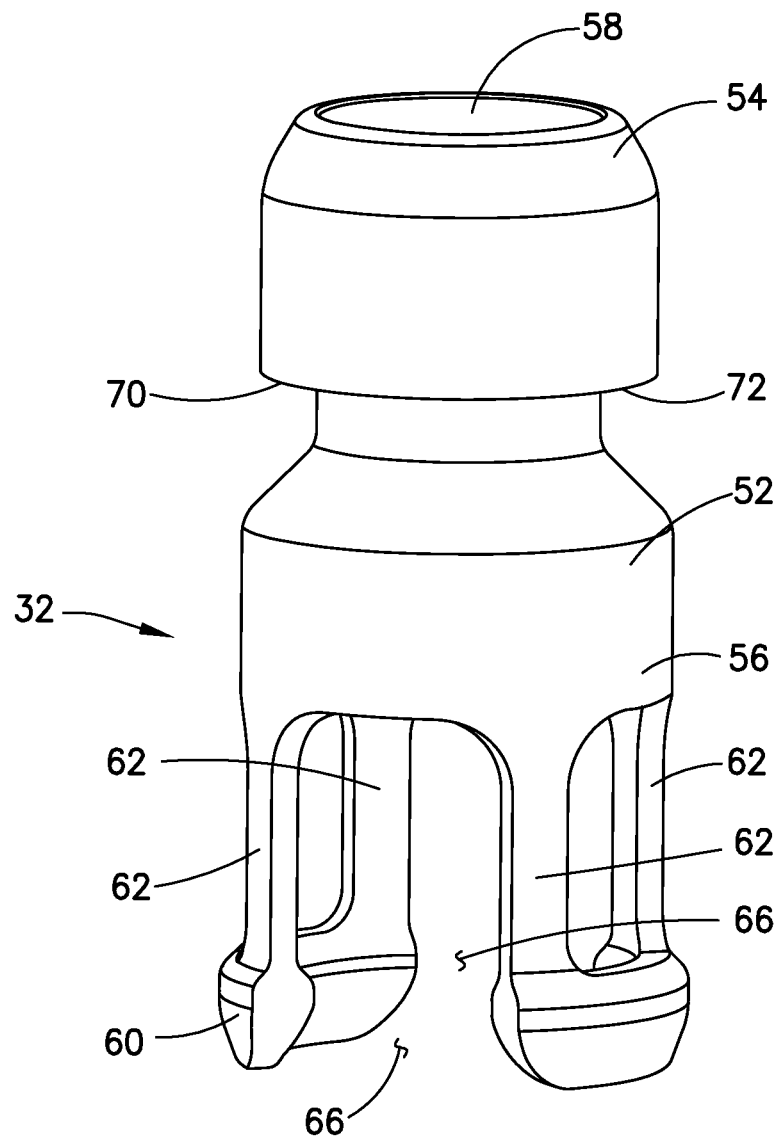
FIG. 9 is a perspective view of a collet of the syringe adapter of FIG. 2 according to one aspect of the present invention.

As shown in FIG. 9, the locking member 60 of the collet 32 defines a pair of openings 66 that extend in a direction perpendicular to a longitudinal axis of the collet 32. The openings 66 bifurcate the locking member 60 into two arcuate portions that are each connected to the body 52 of the collet 32 by two arms 62. However, as discussed in more detail below, other suitable arrangements and shapes for the collet 32 and the locking member 60 may be utilized. The locking member 60 of the collet 32 protrudes radially inward and radially outward relative to the plurality of arms 62.

Referring again to FIGS. 8-11, the body 52 of the collet 32 includes a second connection interface 70 that is configured to mate with and lock with the first connection interface 36 of the syringe adapter 12. The second connection interface 70 is defined by the body 52 of the collet 32 and, more particularly, is defined by a locking surface 72. The second connection interface 70 further includes a lead-in surface defined by the first end 54 of the collet 32. The lead-in surface of the second connection interface 70 defines a rounded transition between the body 52 of the collet 32 and the lead-in surface. The locking surface 72 is a ring-shaped recess that is recessed relative to the body 52 of the collet 32 and configured to receive the lock member 38 of the first connection interface 36. The locking surface 72 is defined by 90 degree angles, although other suitable shapes and angles may be utilized. The first end 54 of the collet 32 is configured to be received within the interior space 22 of the syringe adapter 12 when the lock member 38 of the first connection interface 36 is in the open position and restricted from moving within the interior space 22 of the syringe adapter 12 when the lock member 38 is in the closed position. The lead-in surface of the second connection interface 70 is configured to engage the lock member 38 of the first connection interface 36 to further move the lock member 38 and further bias the cantilever spring 46. When the second connection interface 70 is fully mated to the first connection interface 36, the lock member 38 of the first connection interface 36 is configured to be in the closed position and received within the locking surface 72 to lock the first connection interface 36 from longitudinal and transverse movement relative to the second connection interface 70, but still allowing rotational movement relative thereto.

Figure 8:
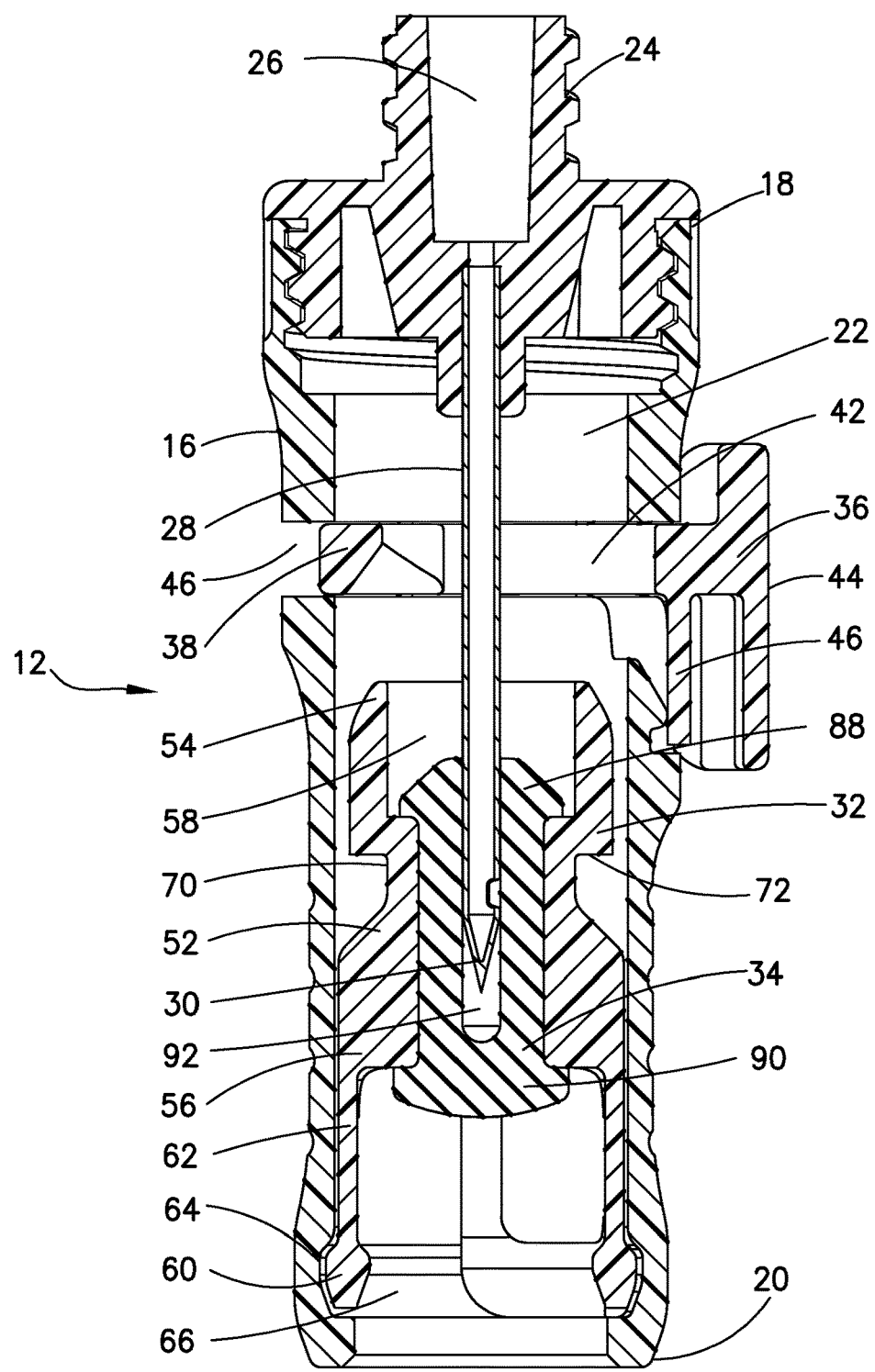
FIG. 8 is a cross-sectional view of the syringe adapter along line 8-8 in FIG. 3 according to one aspect of the present invention.

Referring to FIGS. 2 and 8, the first membrane 34 includes a body 82 having a first end 84 and a second end 86. The first end 84 and the second end 86 of the body 82 of the first membrane 34 include a first head portion 88 and a second head portion 90, respectively. The body 82 of the first membrane 34 defines a passageway 92 extending from the first end 84 towards the second end 86 of the body 82. The passageway 92 terminates at a position intermediate the first and second ends 84, 86 of the body 82. As shown in FIG. 8, the body 82 of the first membrane 34 is received by the passageway 58 of the collet 32 and is secured to the collet 32. The first head portion 88 of the first membrane 34 engages a counter-bored portion of the collet 32 adjacent to the passageway 58 of the collet 32. The second head portion 90 extends beyond the passageway 58 of the body 52 of the collet 32 with the second head portion 90 engaging the body 52 of the collet 32. The second head portion 90 defines a convex surface, although other suitable membrane arrangements may be provided as discussed in more detail below. The cannula 28 is received within the passageway 92 of the first membrane 34 with the distal end 30 of the cannula 28 positioned within the passageway 92 when the collet 32 is in the first position. The distal end 30 of the cannula 28 is configured to pierce the first membrane 34 and extend through the first membrane 34 when the collet 32 is transitioned from the first position to the second position. The first membrane 34 is configured to engage and seal an intermediate portion of the cannula 28 during use of the syringe adapter 12 to maintain a sealed and leak-free connection with the patient connector 14 or mating component.

As discussed in more detail below, upon engagement of the first membrane 34 by a corresponding membrane during use, such as a membrane from the patient connector 14, a vial adapter, or IV bag spike, the collet 32 is configured to move toward the first end 18 of the syringe adapter 12 and transition from the first position to the second position such that the distal end 30 of the cannula 28 pierces the first membrane 34 to place the syringe adapter 12 in fluid communication with corresponding devices secured to the syringe adapter 12. When the collet 32 is returned to the first position, the first membrane 34 can be disengaged from the corresponding membrane thereby positioning the distal end 30 of the cannula 28 within the passageways 58, 92 of the collet 32 and the first membrane 34. Such an arrangement shields the distal end 30 of the cannula 28 to prevent accidental needle sticks and also prevents the leakage of any fluid during transfer of fluids when using the syringe adapter 12.

Referring to FIGS. 12-16, the patient connector 14 includes a body 102 having a first end 104 and a second end 106 and defining a passageway 108 that extends therethrough. The first end 104 of the patient connector 14 also includes a collet interface 110. The collet interface 110 is defined by a portion of the body 102 of the patient connector 14 that is recessed relative to the first end 104 of the body 102 of the patient connector 14. The first end 104 of the body 102 of the patient connector 14 also includes a membrane seat 112 that receives a second membrane 114. As discussed above in connection with the syringe adapter 12, the second membrane 114 of the patient connector 14 is configured to engage the first membrane 34 of the syringe adapter 12 and provide a substantially leak-free connection with the syringe adapter 12 during fluid transfer. The second end 106 of the patient connector 14 includes an IV line attachment 116, such as a male luer connector, although any other suitable connection arrangement may be utilized.

Figure 17:
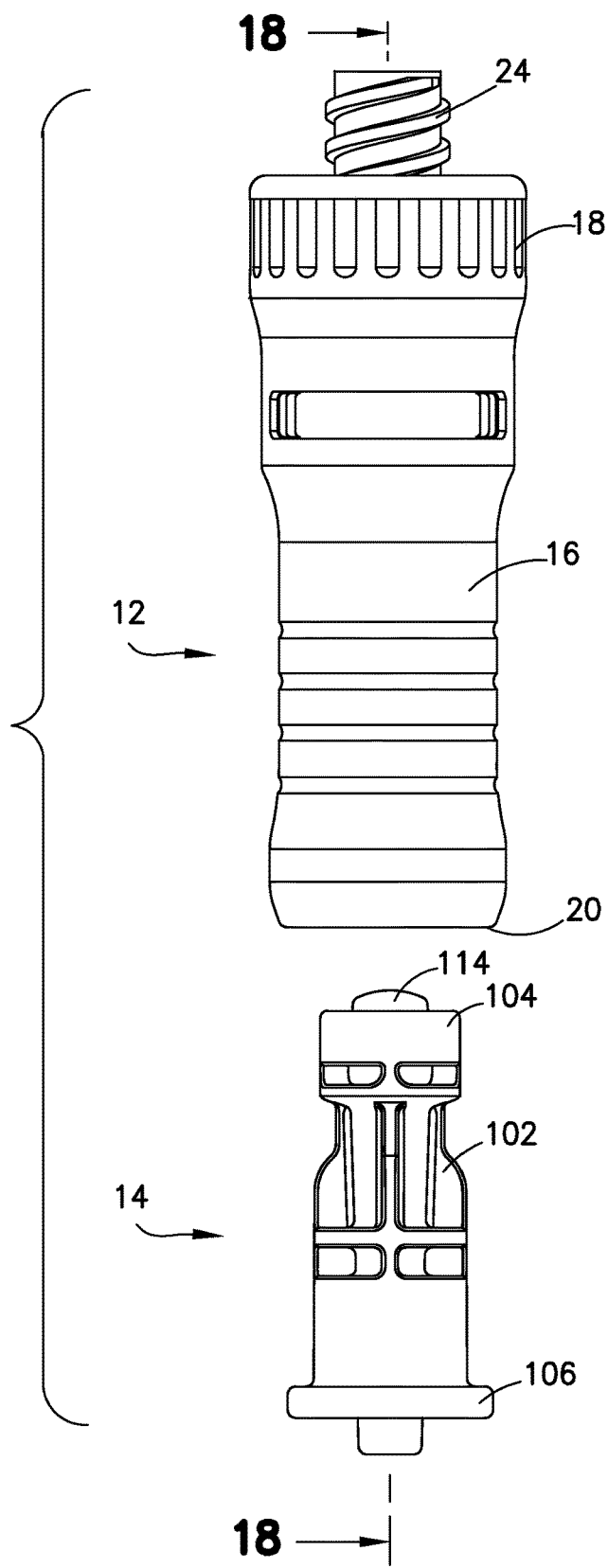
FIG. 17 is a rear view of the system of FIG. 1 showing a first stage of securing a syringe adapter to a patient connector according to one aspect of the present invention.
Figure 18:
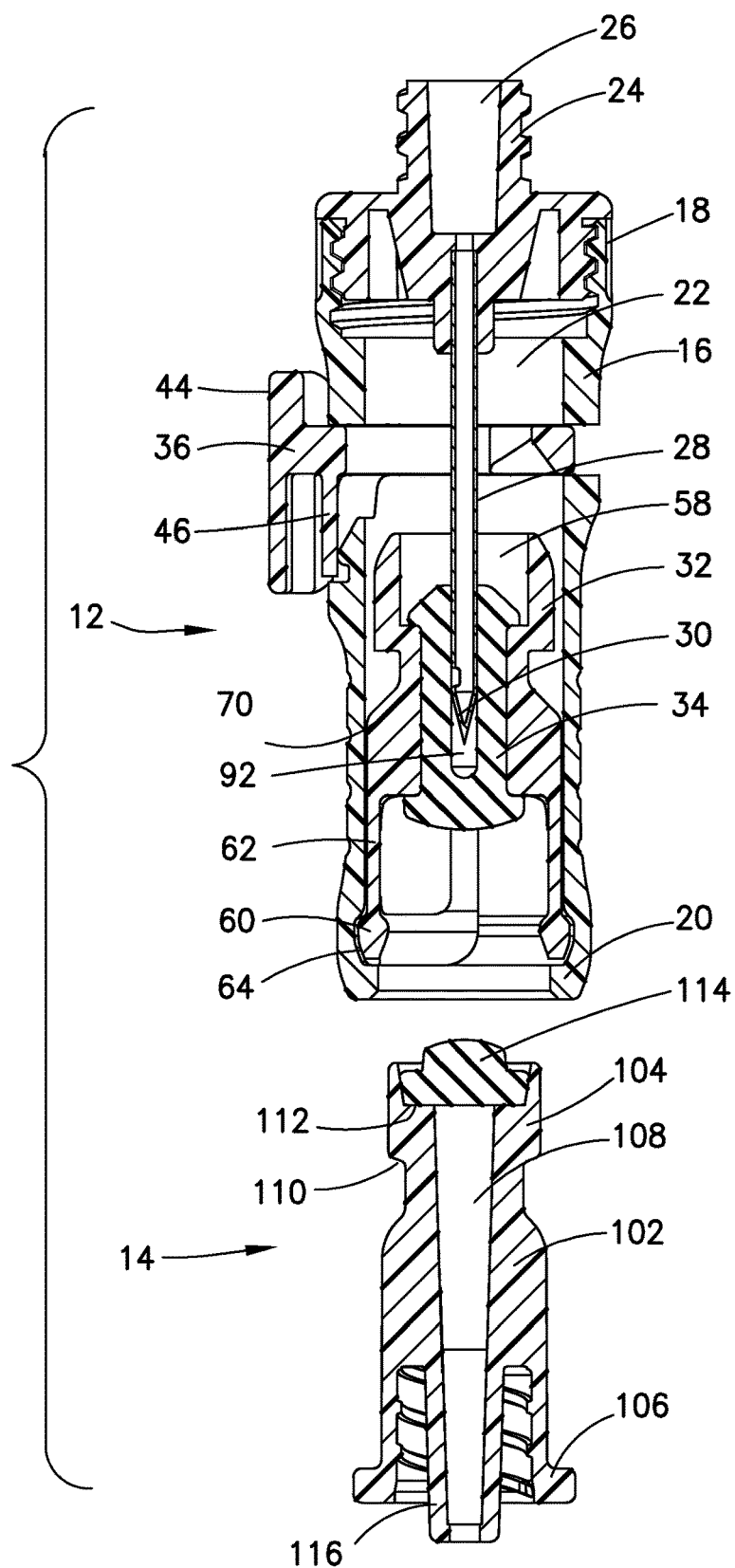
FIG. 18 is a cross-sectional view of the system along line 18-18 in FIG. 17 according to one aspect of the present invention.
Figure 19:
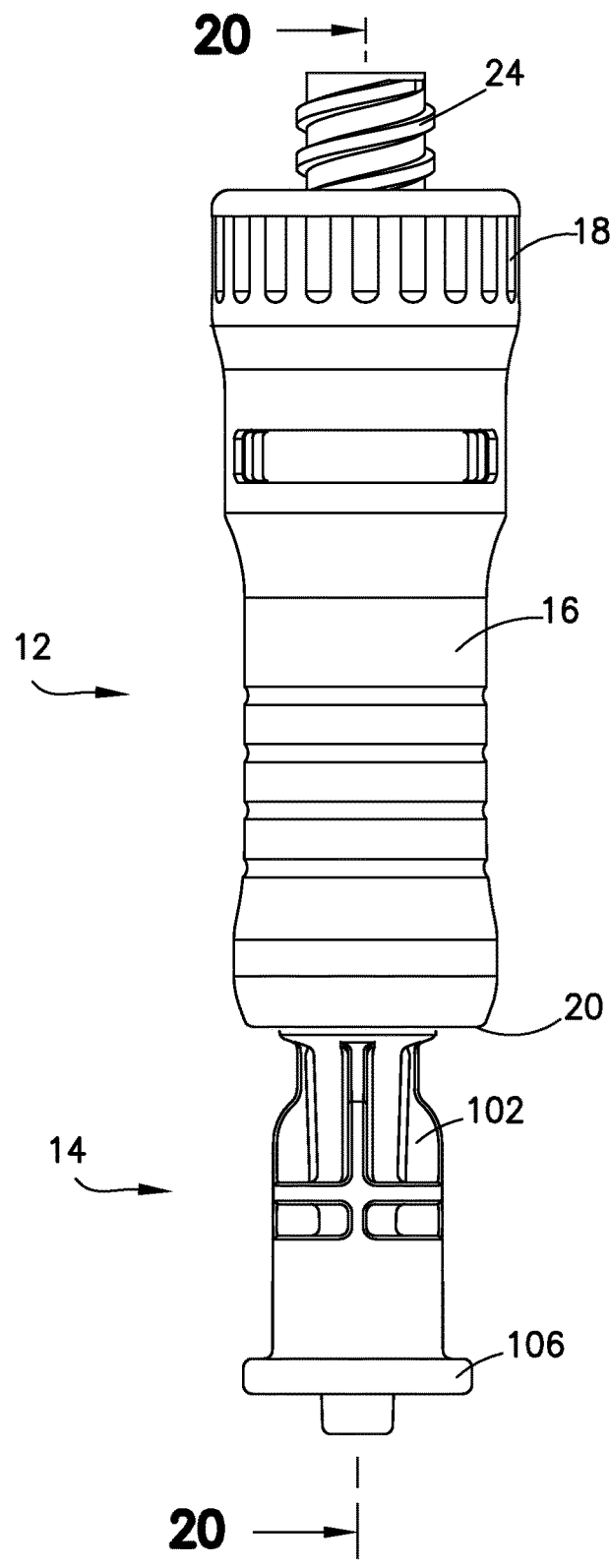
FIG. 19 is a rear view of the system of FIG. 1 showing a second stage of securing a syringe adapter to a patient connector according to one aspect of the present invention.
Figure 20:
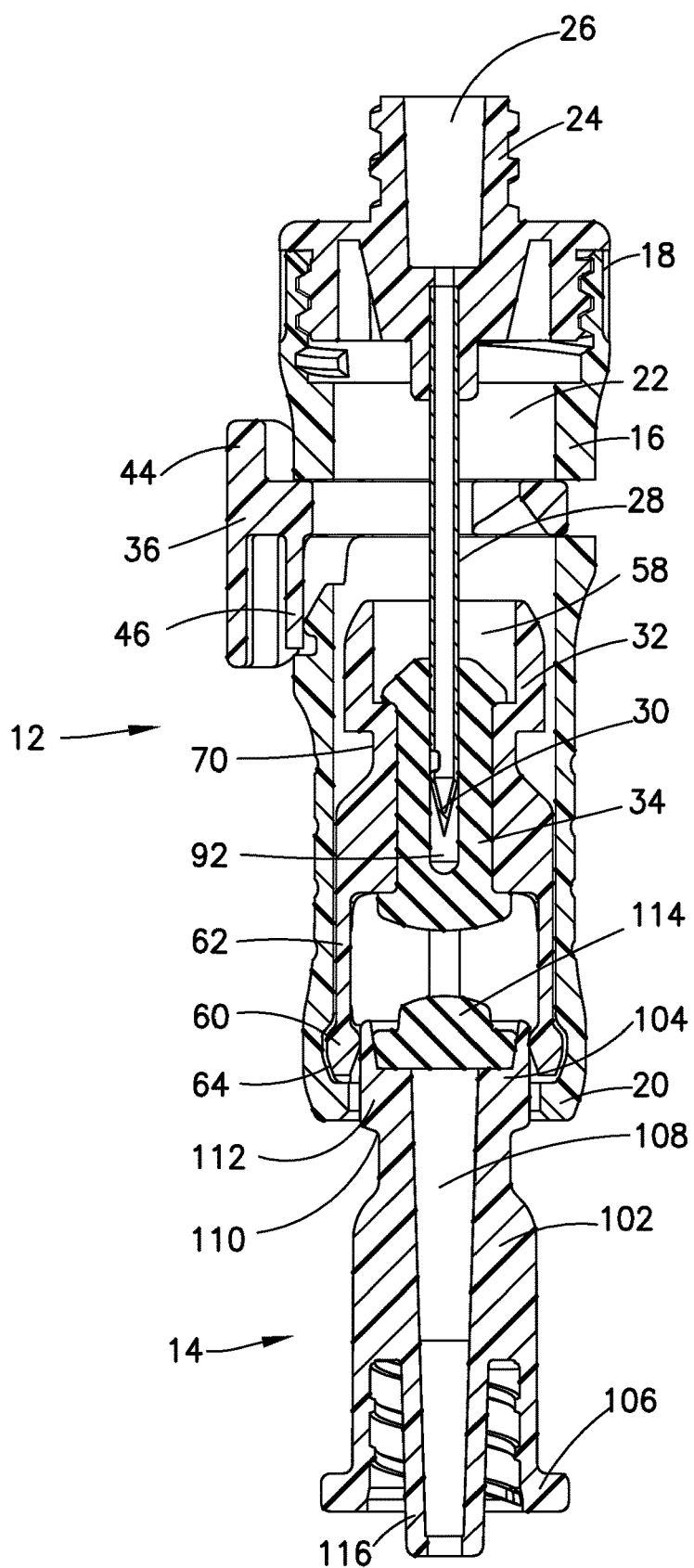
FIG. 20 is a cross-sectional view of the system along line 20-20 in FIG. 19 according to one aspect of the present invention.

Referring to FIGS. 17-26, the process of mating the syringe adapter 12 with the patient connector 14 is shown. Although the syringe adapter 12 is shown being connected to the patient connector 14, the syringe adapter 12 would similarly connect to other components having similar structure as the patient connector 14, including, but not limited to, vial adapters and IV bag adapters. As shown in FIGS. 17 and 18, the interior space 22 of the syringe adapter 12 is aligned with the patient connector 14. In particular, the longitudinal axis of the syringe adapter 12 is aligned with the longitudinal axis of the patient connector 14 with the lock member 38 of the first connection interface 36 in the closed position. As shown in FIGS. 19 and 20, the patient connector 14 is moved into the interior space 22 of the syringe adapter 12 towards the collet 32 with the collet 32 provided in the first position such that the locking member 60 is open to receive the patient connector 14.

Figure 21:
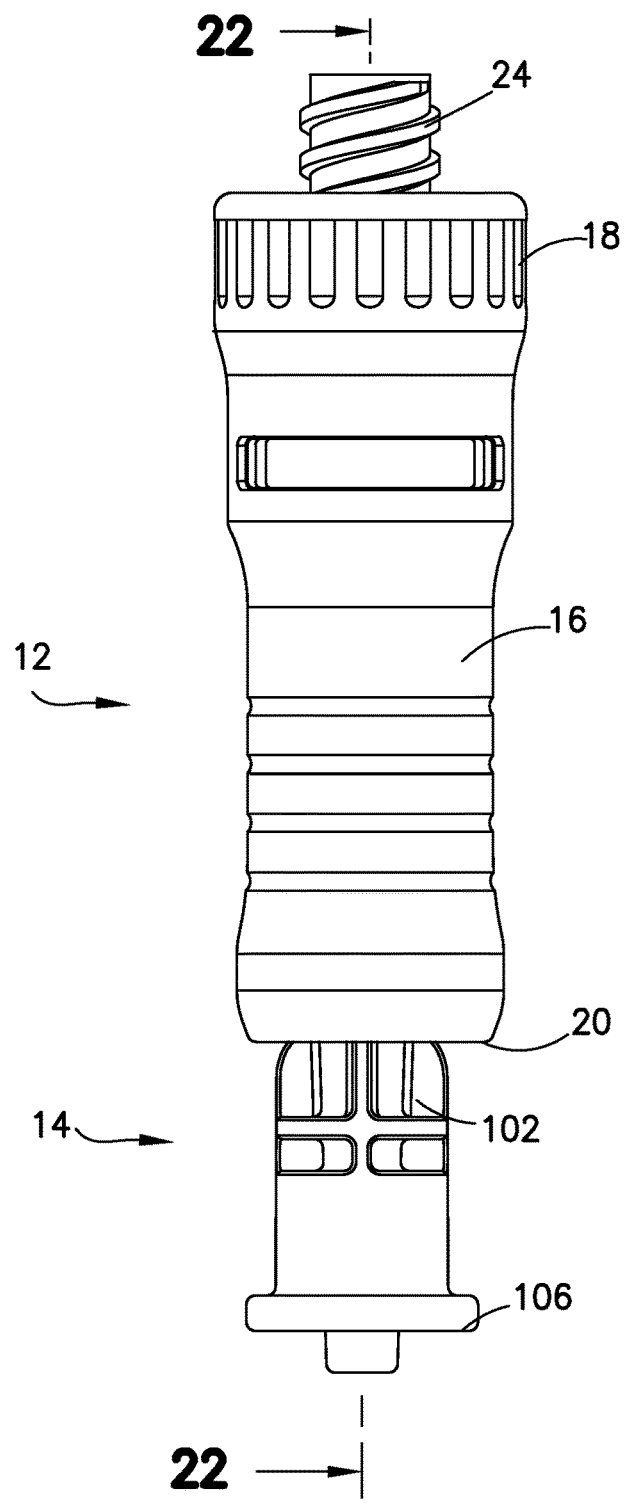
FIG. 21 is a rear view of the system of FIG. 1 showing a third stage of securing a syringe adapter to a patient connector according to one aspect of the present invention.
Figure 22:
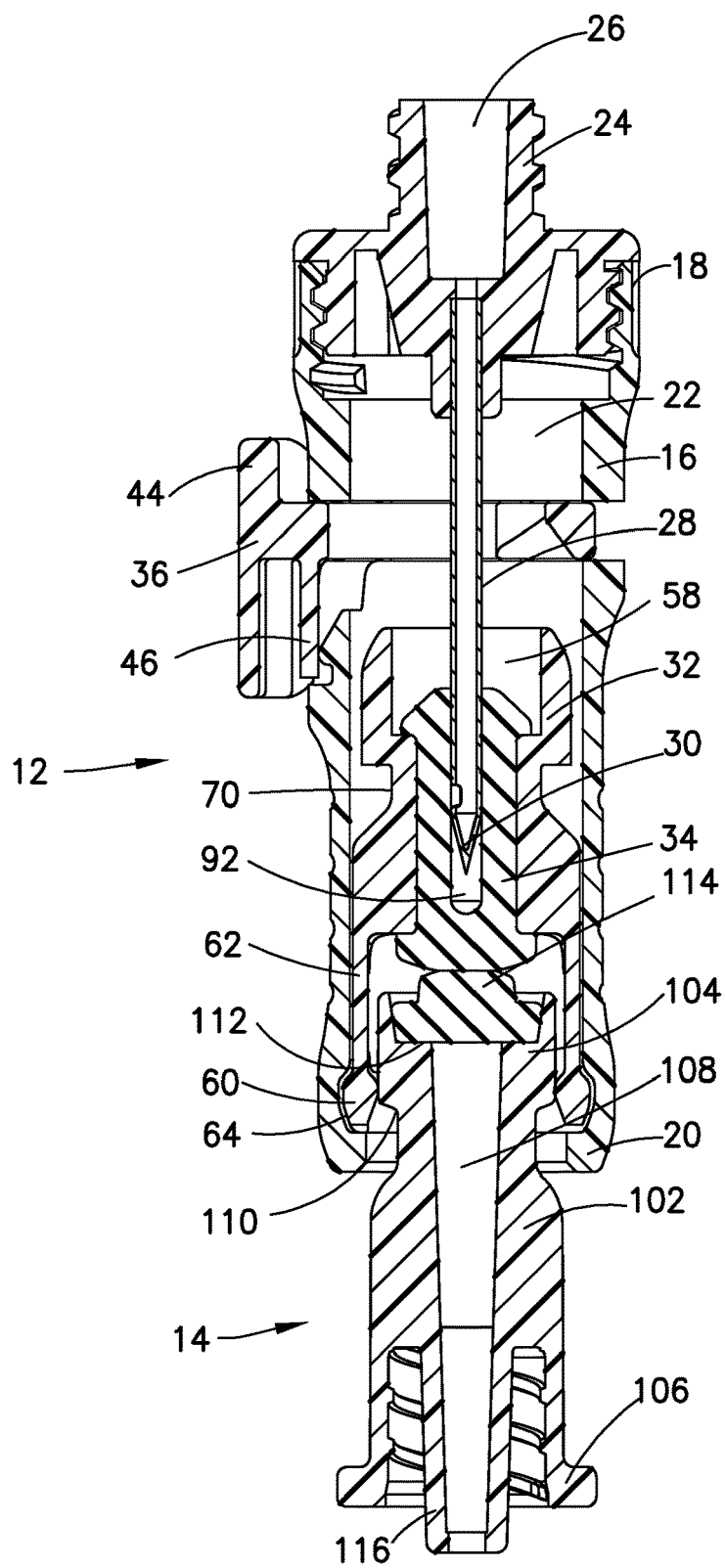
FIG. 22 is a cross-sectional view of the system along line 22-22 in FIG. 21 according to one aspect of the present invention.

Referring to FIGS. 21 and 22, further movement of the patient connector 14 towards the first end 18 of the syringe adapter 12 causes the first membrane 34 to engage the second membrane 114 and the first end 104 of the patient connector 14 to pass through the locking member 60 of the collet 32. As discussed above, movement of the patient connector 14 within the locking member 60 may bias the locking member 60 radially outward or, alternatively, may receive the first end 104 of the patient connector 14 without any radial movement of the locking member 60. Due to the interference between the locking member 60 and the housing 16 of the syringe adapter 12 as well as the contact of the first end 104 of the patient connector 14 and the locking member 60, the collet 32 will not move toward the first end 18 of the syringe adapter 12 until first and second membranes 34, 114 have been sufficiently compressed and the locking member 60 is received within the collet interface 110 of the patient connector 14. Once the first and second membranes 34, 114 have been sufficiently compressed, the locking member 60 will be forced into the collet interface 110 of the patient connector 14 due to the engagement of the locking member 60 with the housing 16 of the syringe adapter 12 and the continued axial movement of the collet 32 toward the first end 18 of the syringe adapter 12.

Figure 23:
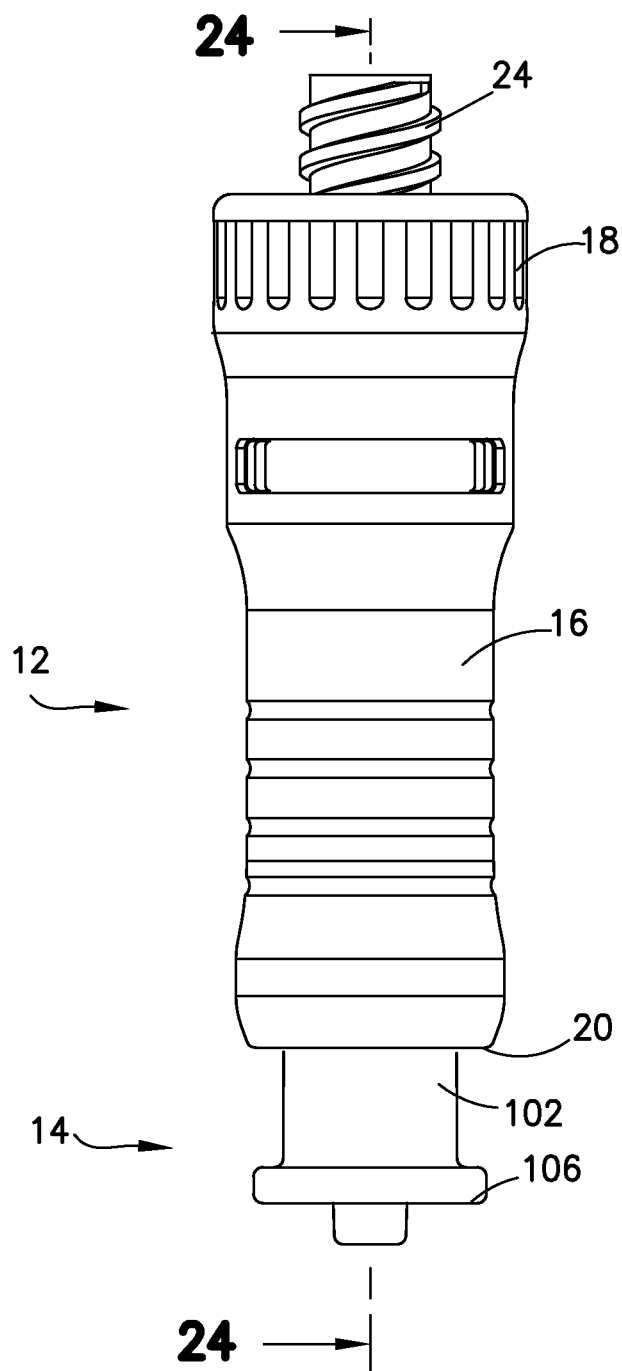
FIG. 23 is a rear view of the system of FIG. 1 showing a fourth stage of securing a syringe adapter to a patient connector according to one aspect of the present invention.
Figure 24:
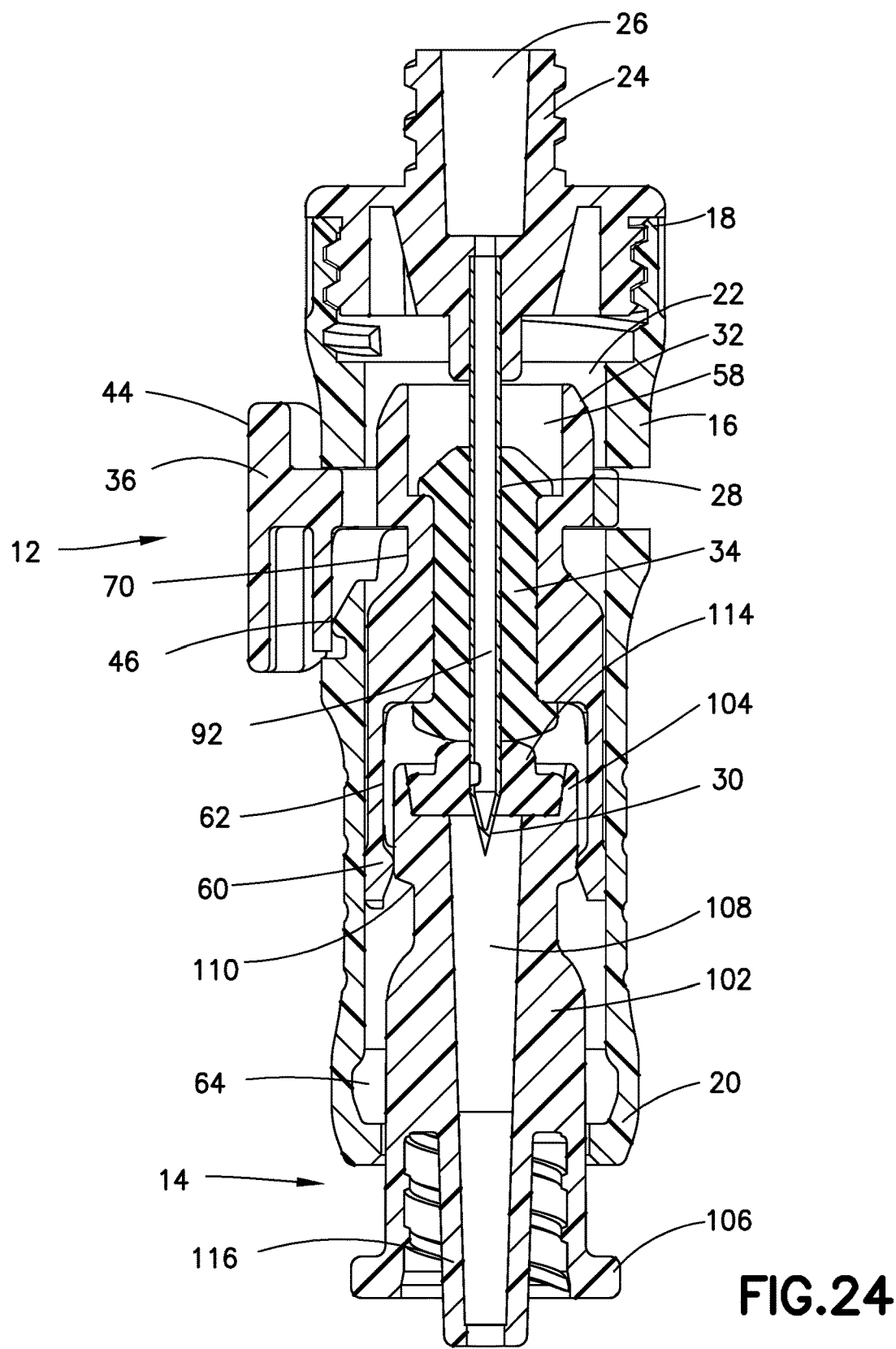
FIG. 24 is a cross-sectional view of the system along line 24-24 in FIG. 23 according to one aspect of the present invention.

Referring to FIGS. 23 and 24, further continued movement of the patient connector 14 towards the first end 18 of the syringe adapter 12 causes the collet 32 to also move towards the first end 18 of the syringe adapter 12 via the engagement between the first and second membranes 34, 114. At this stage, the collet 32 is in the second position and the first end 104 of the patient connector 14 will be locked and secured to the collet 32 due to the engagement of the locking member 60 of the collet 32 with the collet interface 110. The locking member 60 of the collet 32 cannot expand radially outward to release the patient connector 14 until the collet 32 is returned to the first position. Further, during continued movement at this stage, the lock member 38 of the first connection interface 36 engages the second connection interface 70 of the collet 32, which transitions the lock member 38 from the closed position (shown in FIG. 22) to the open position (shown in FIG. 24).

When the lock member 38 is moved from the closed position to the open position, the cantilever spring 46 will engage the cam surface of the housing 16 of the syringe adapter 12, which creates a biasing force that urges the lock member 38 back to the closed position. Such movement back to the closed position, however, is prevented by engagement of the lock member 38 with the body 52 of the collet 32. Although FIG. 24 shows an overlap between the collet 32 and the first connection interface 36, the collet 32 would move the first connection interface 36 as described herein. Similarly, the locking member 60 of the collet 32 would not overlap with the housing 16 of the syringe adapter 12, but would be forced inwardly as described herein. With the lock member 38 of the first connection interface 36 in the open position, the second connection interface 70 is allowed to continue its movement within the interior space 22 of the syringe adapter 12 to continue the process of mating the syringe adapter 12 to the patient connector 14. During this step, the distal end 30 of the cannula 28 pierces the first and second membranes 34, 114 and is placed in fluid communication with the passageway 108 of the patient connector 14.

Figure 25:
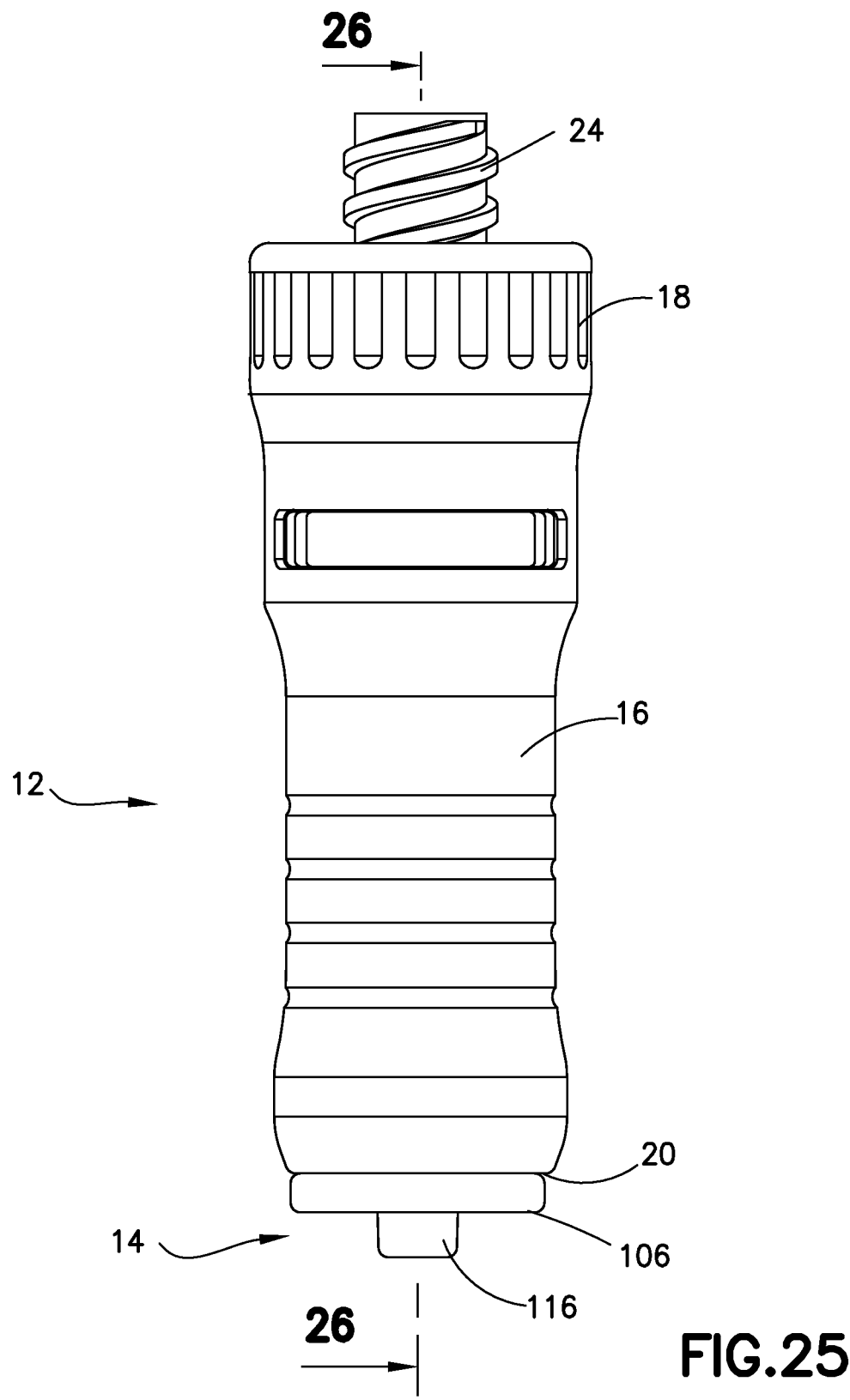
FIG. 25 is a rear view of the system of FIG. 1 showing a final stage of securing a syringe adapter to a patient connector according to one aspect of the present invention.
Figure 26:
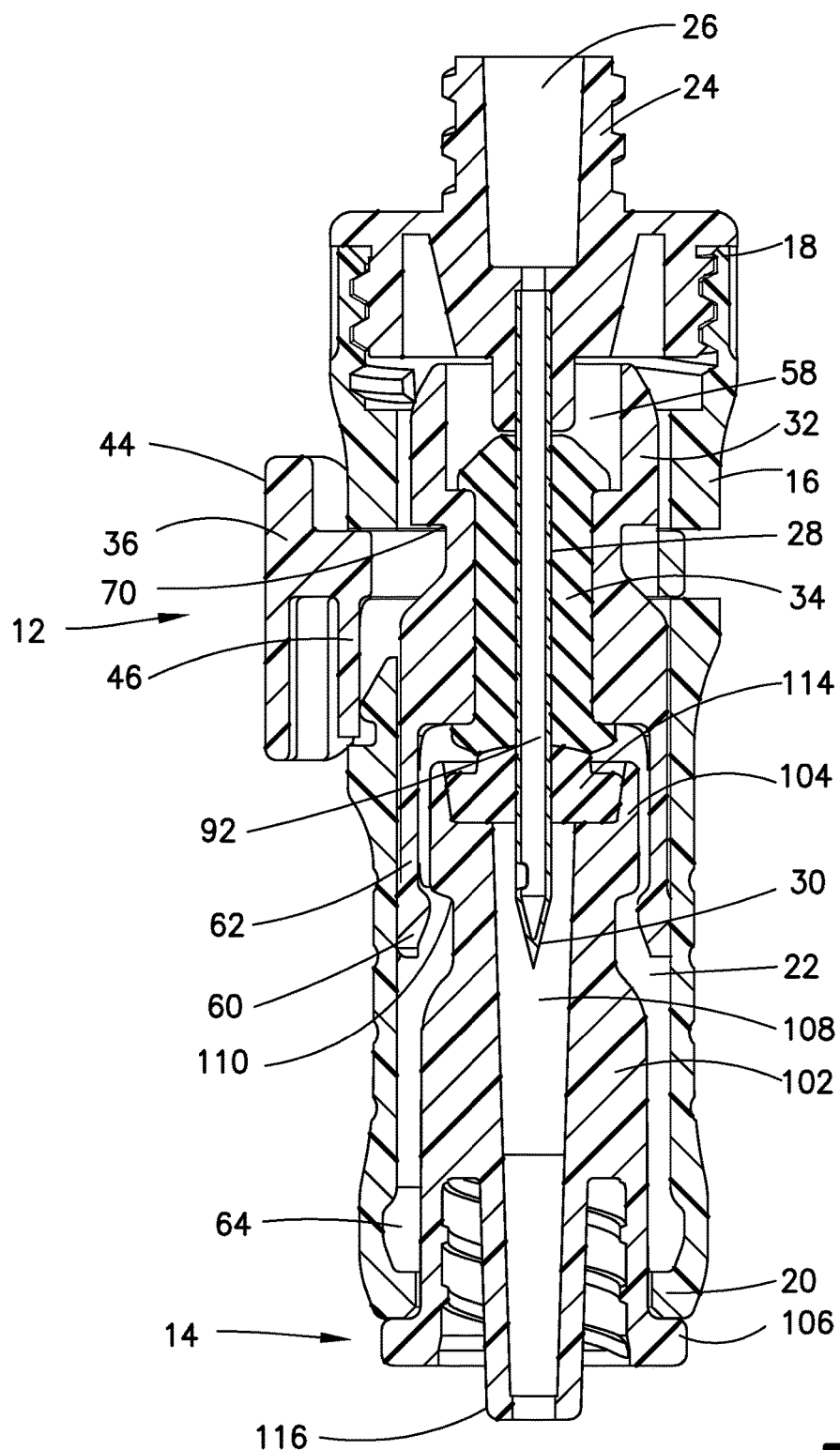
FIG. 26 is a cross-sectional view of the system along line 26-26 in FIG. 25 according to one aspect of the present invention.
Figure 27:
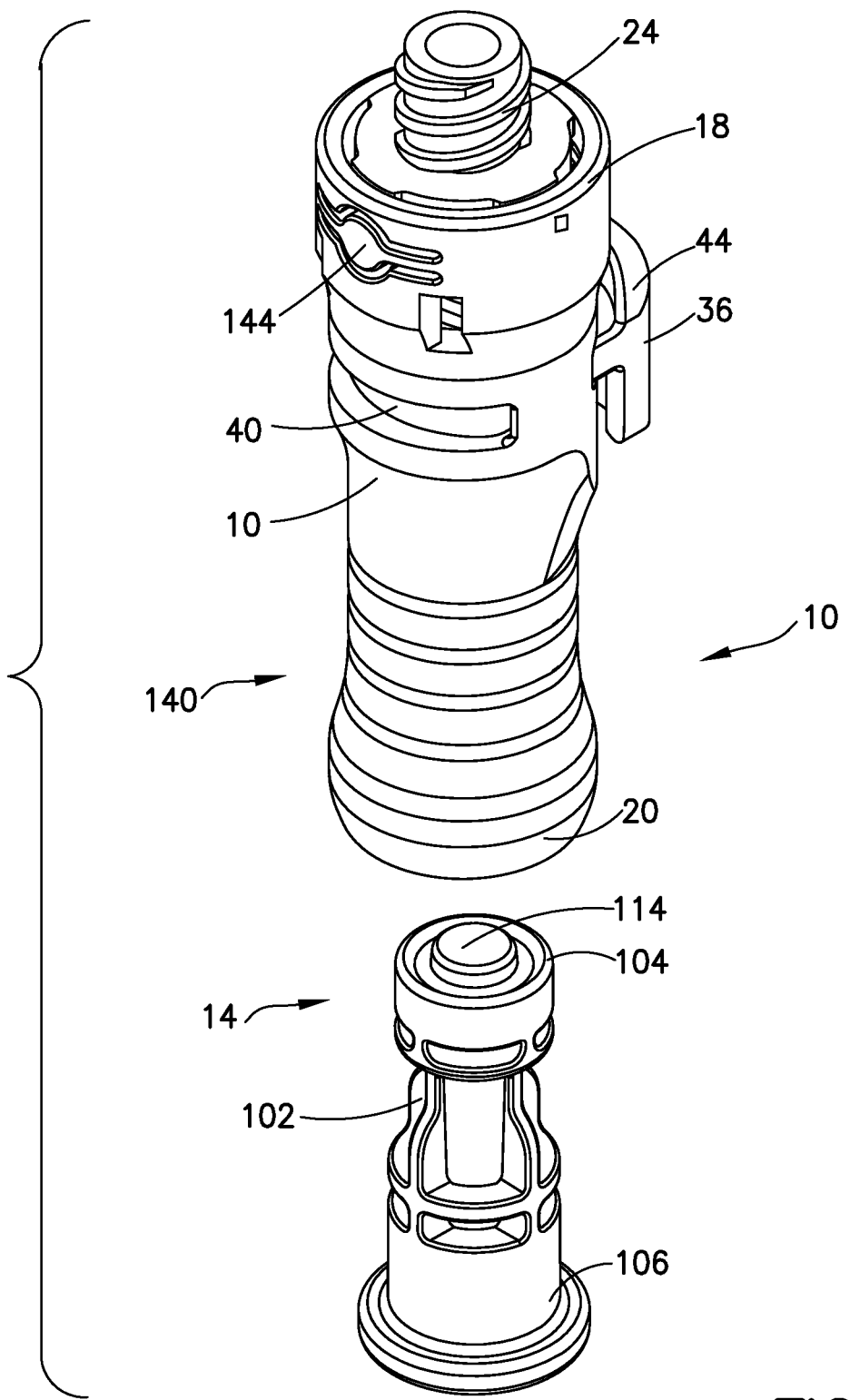
FIG. 27 is a perspective view of a system according to a second aspect of the present invention.
Figure 28:
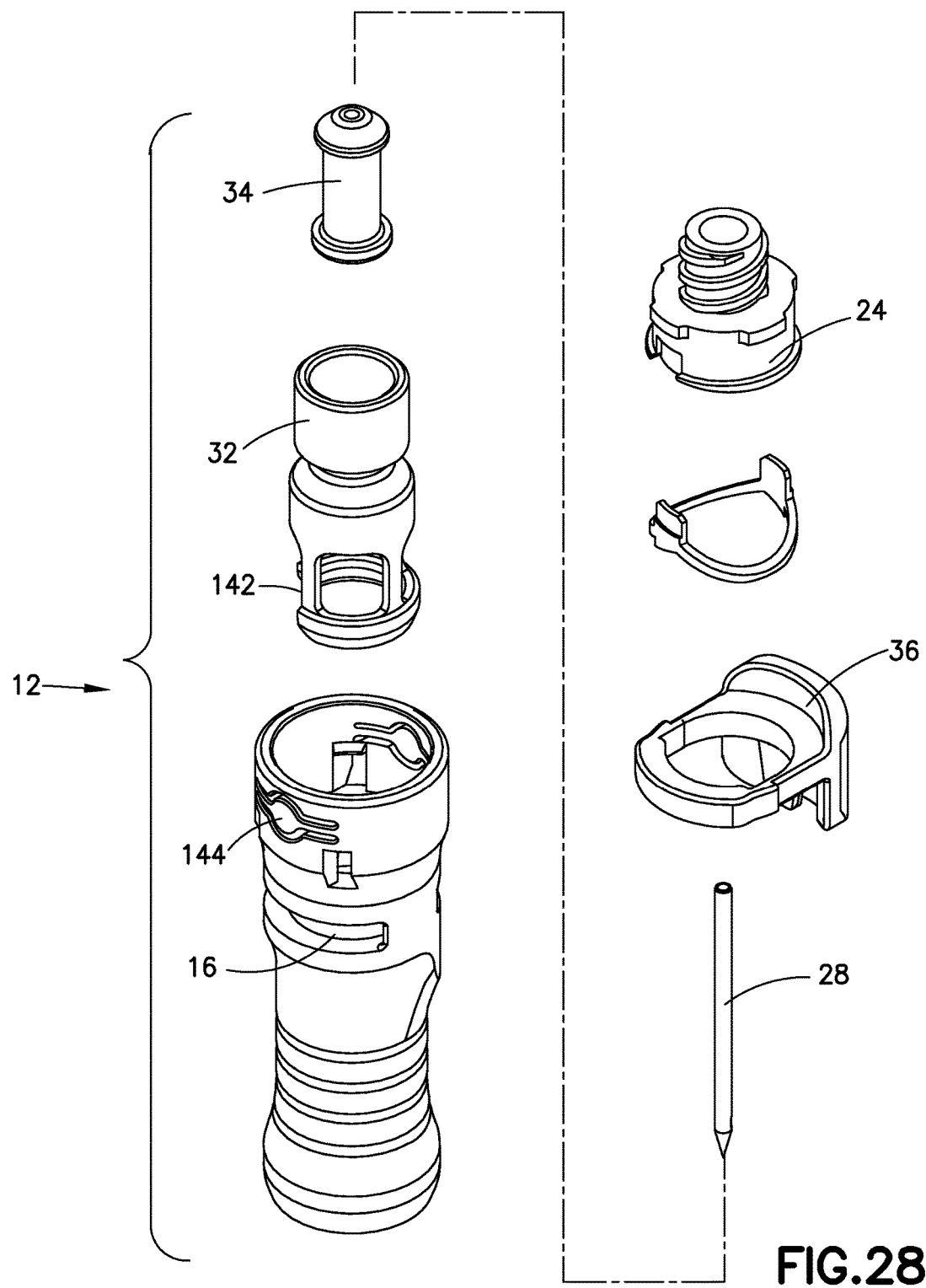
FIG. 28 is an exploded perspective view of the system of FIG. 27 according to one aspect of the present invention.
Figure 29:
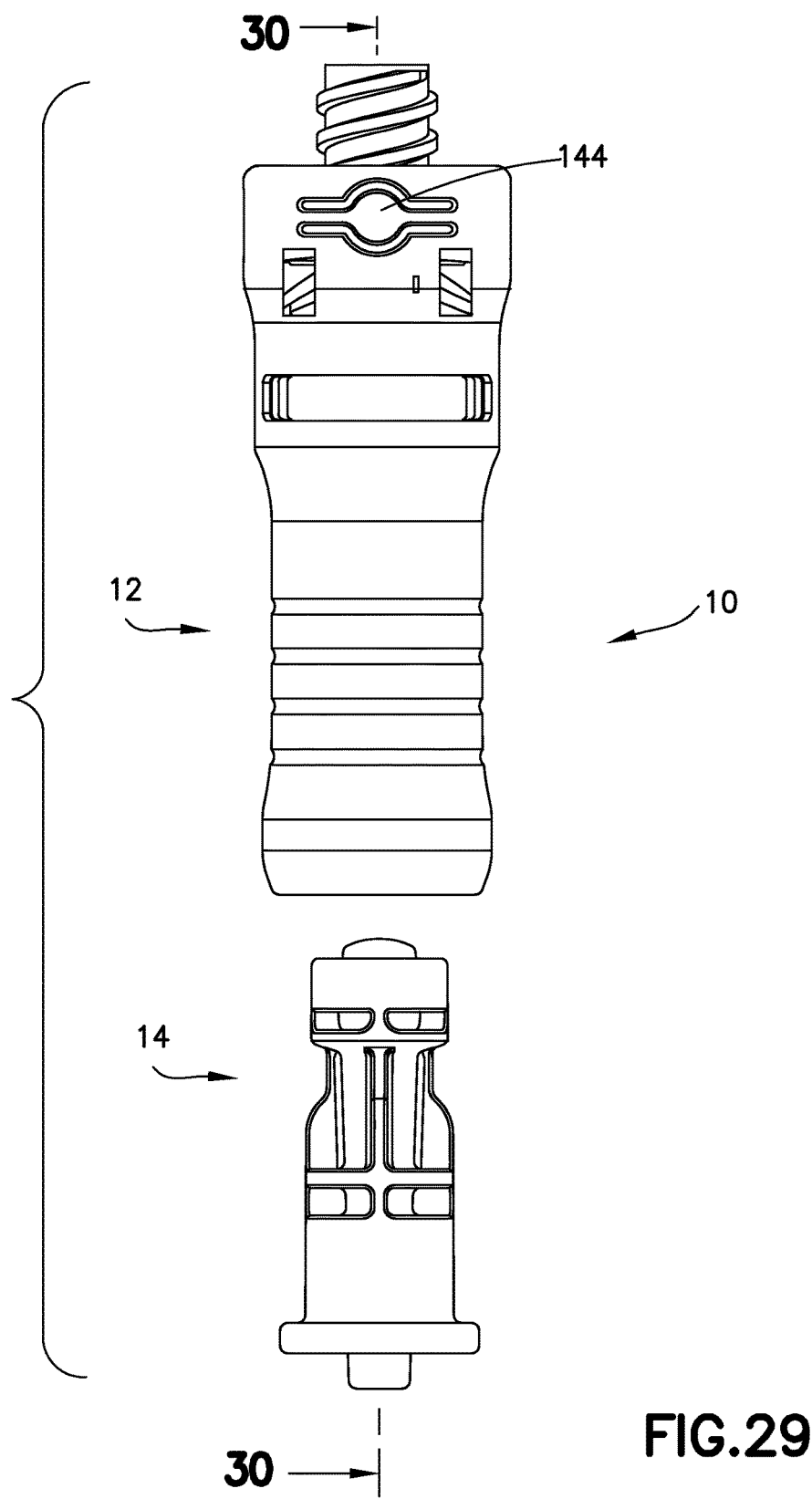
FIG. 29 is a rear view of the system of FIG. 27 according to one aspect of the present invention.
Figure 30:
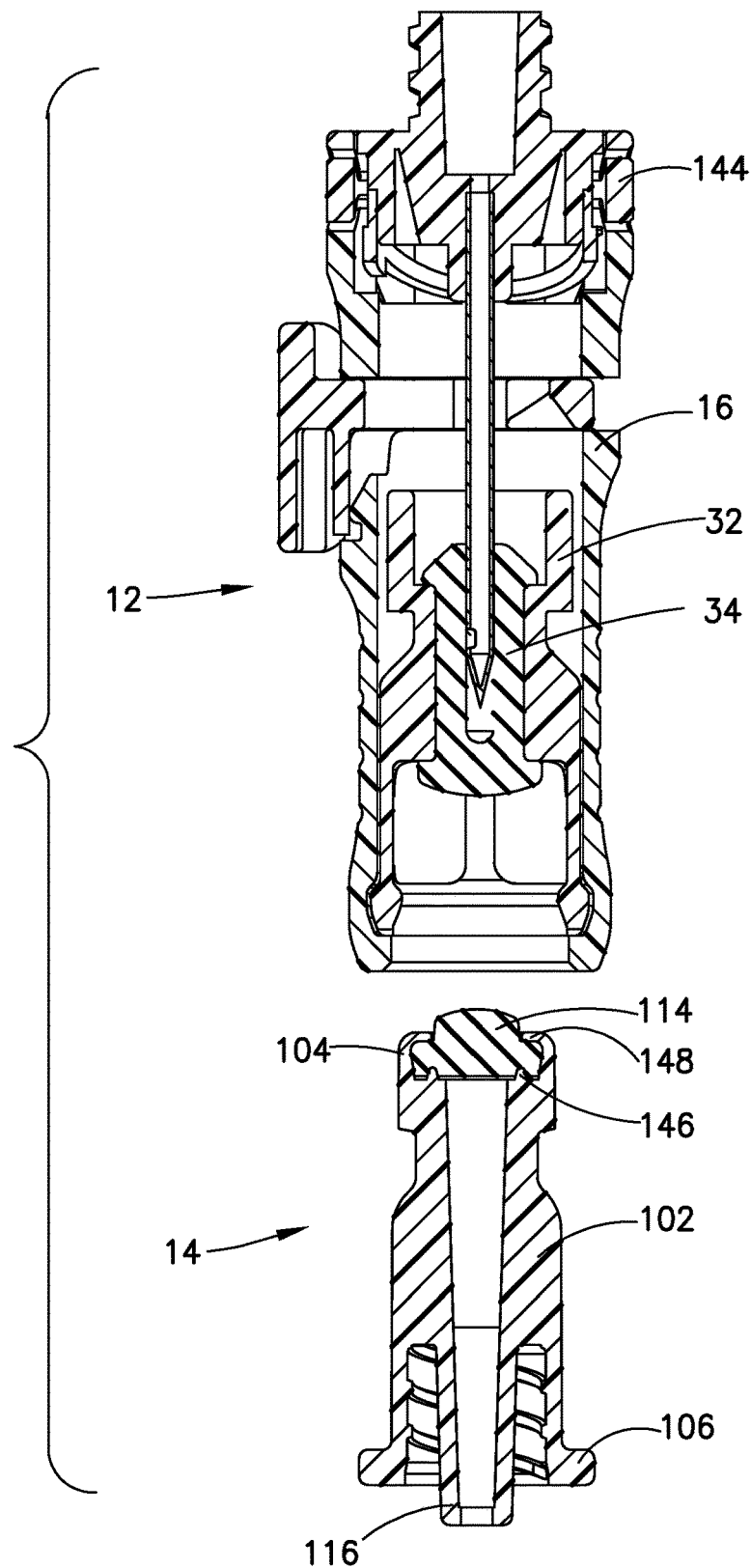
FIG. 30 is a cross-sectional view of the system along line 30-30 in FIG. 29 according to one aspect of the present invention.
Figure 31:
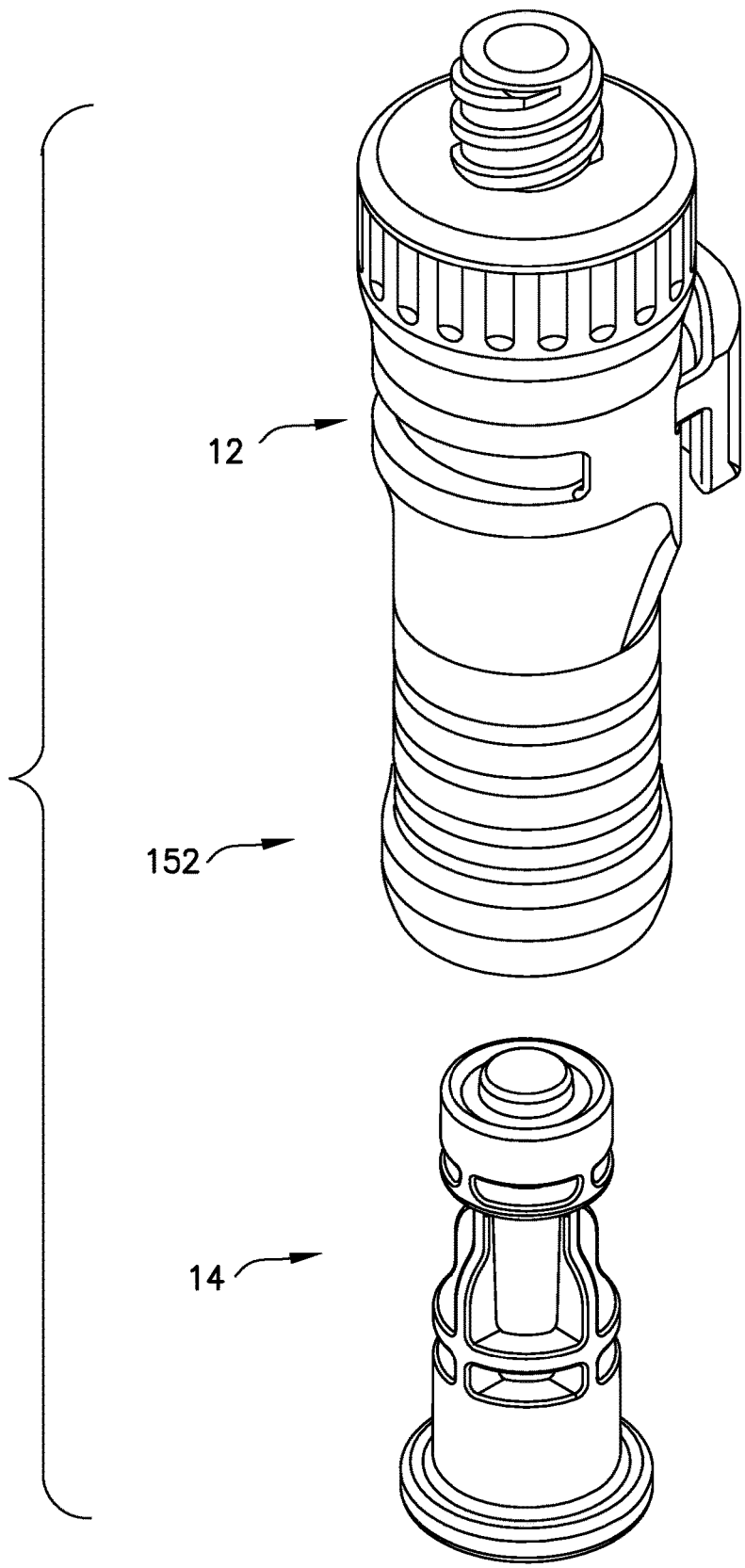
FIG. 31 is a perspective view of a system according to a third aspect of the present invention.
Figure 32:
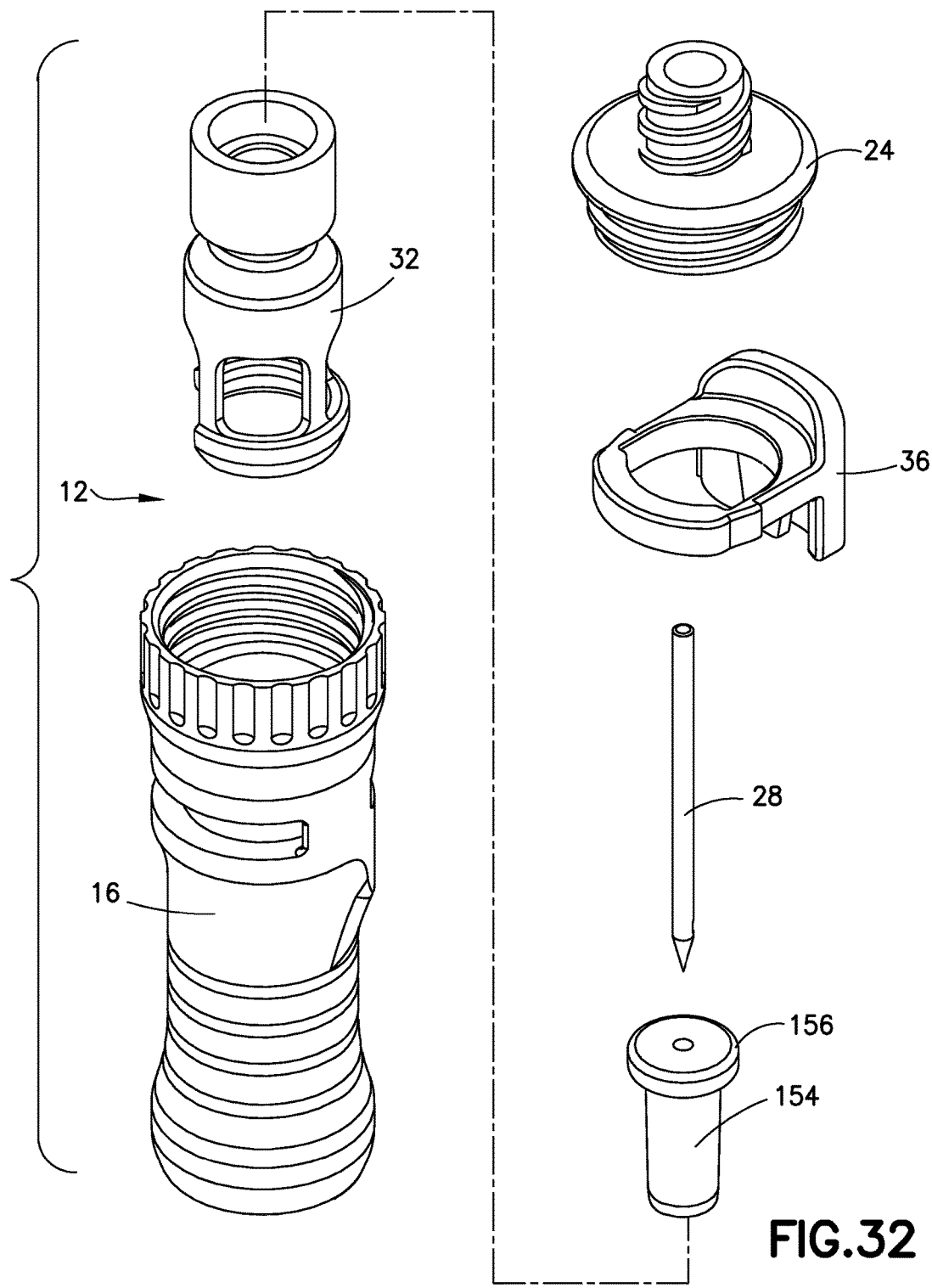
FIG. 32 is an exploded perspective view of the system of FIG. 31 according to one aspect of the present invention.
Figure 33:
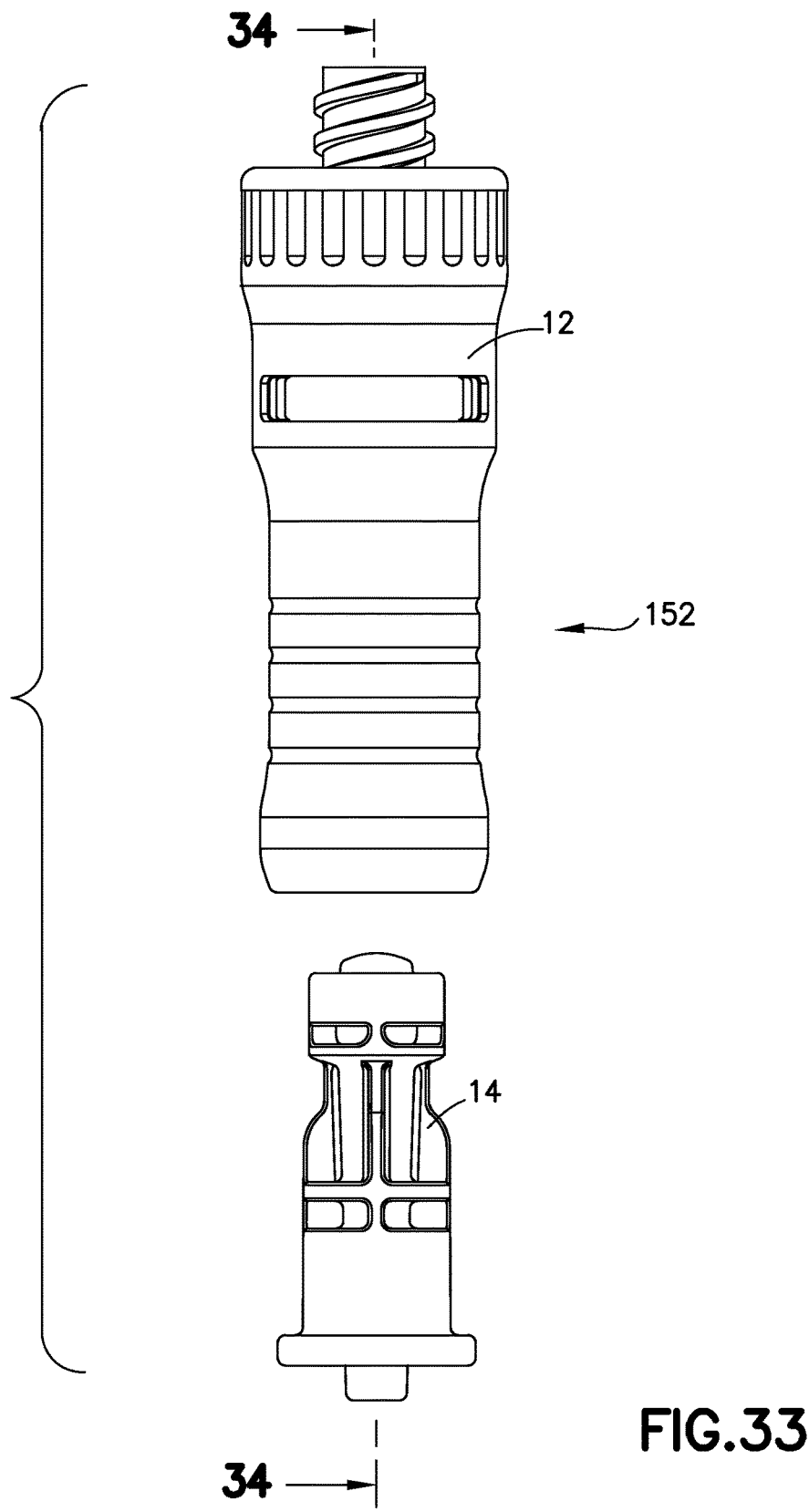
FIG. 33 is a rear view of the system of FIG. 31 according to one aspect of the present invention.
Figure 34:
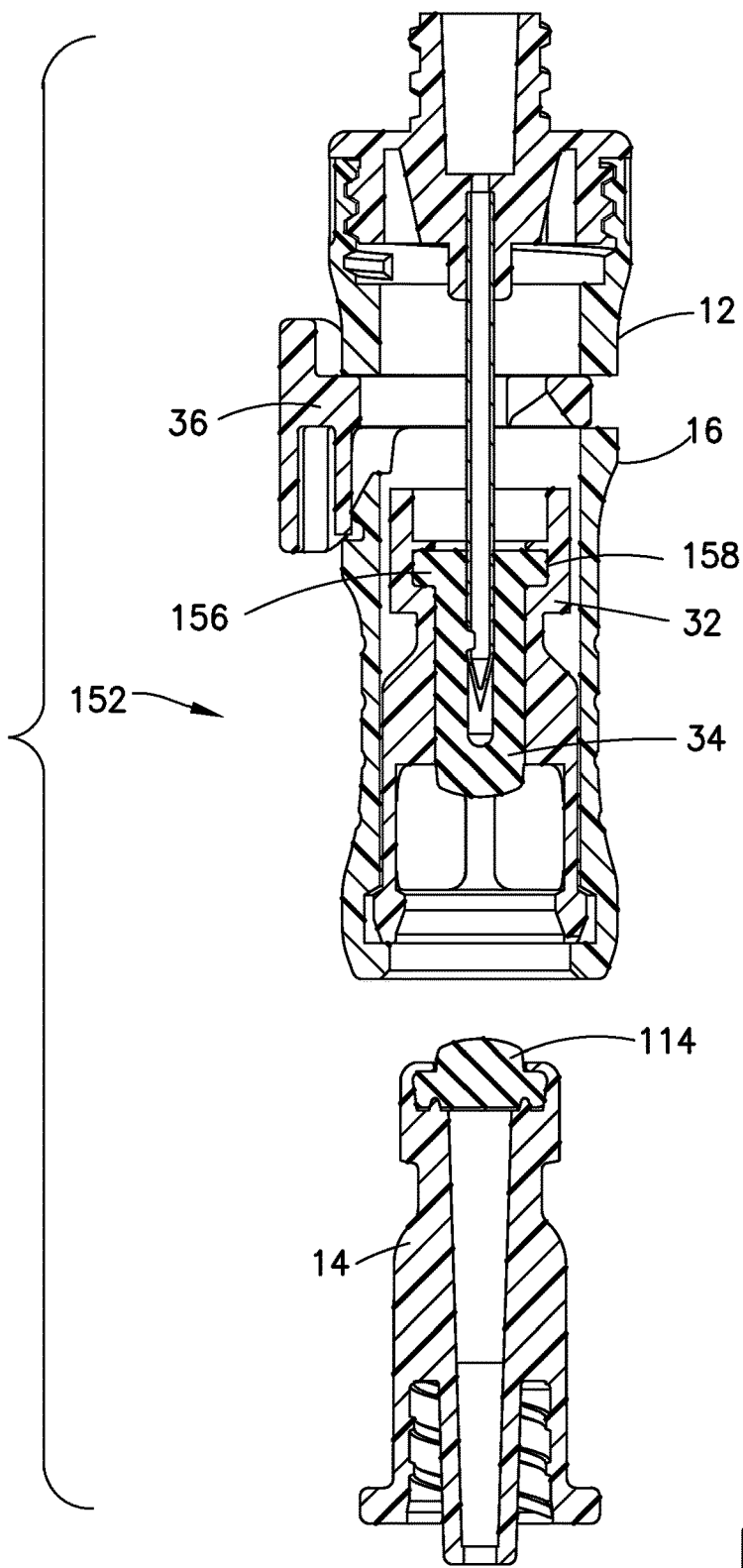
FIG. 34 is a cross-sectional view of the system along line 34-34 in FIG. 33 according to one aspect of the present invention.
Figure 35:
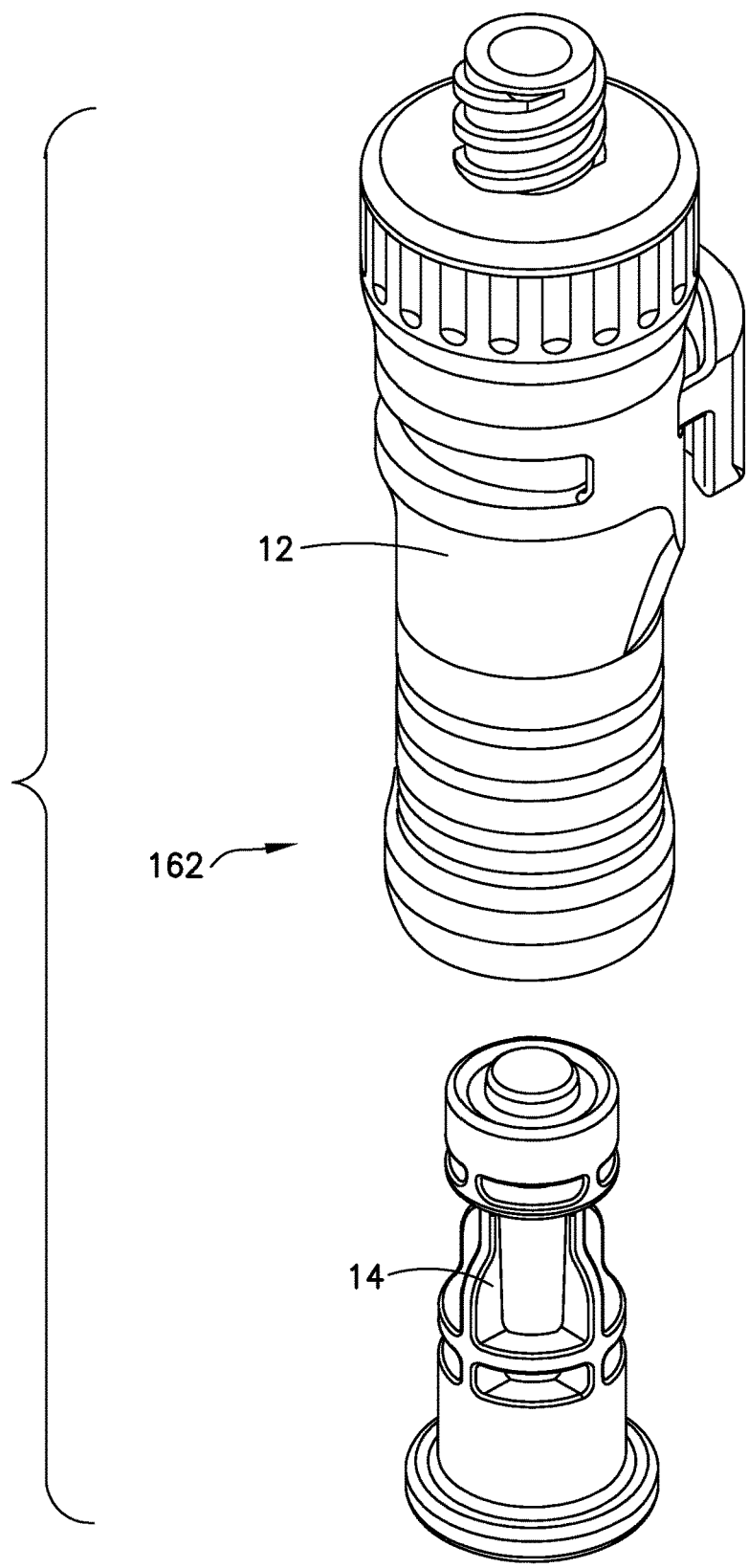
FIG. 35 is a perspective view of a system according to a fourth aspect of the present invention.
Figure 36:
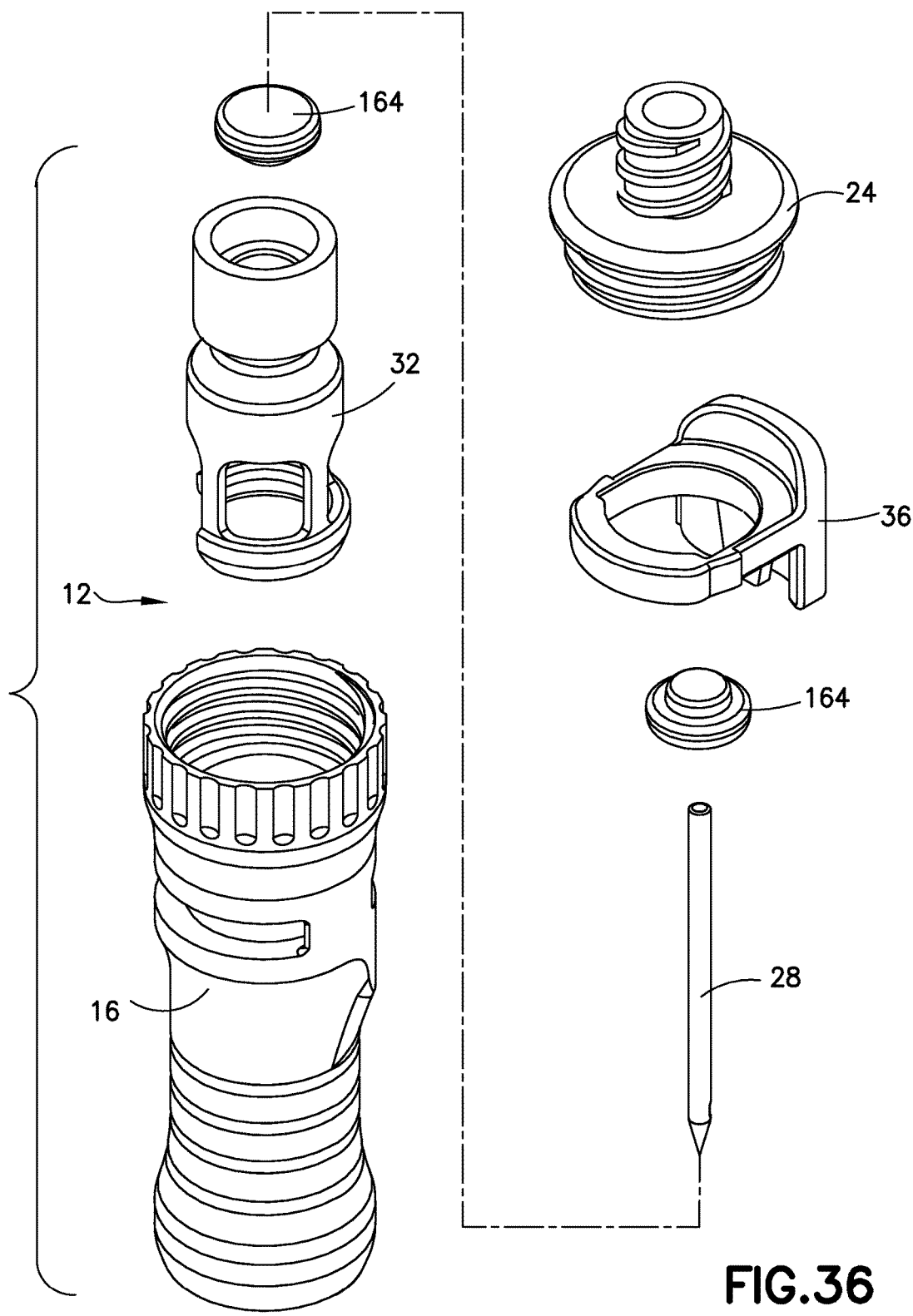
FIG. 36 is an exploded perspective view of the system of FIG. 35 according to one aspect of the present invention.
Figure 37:
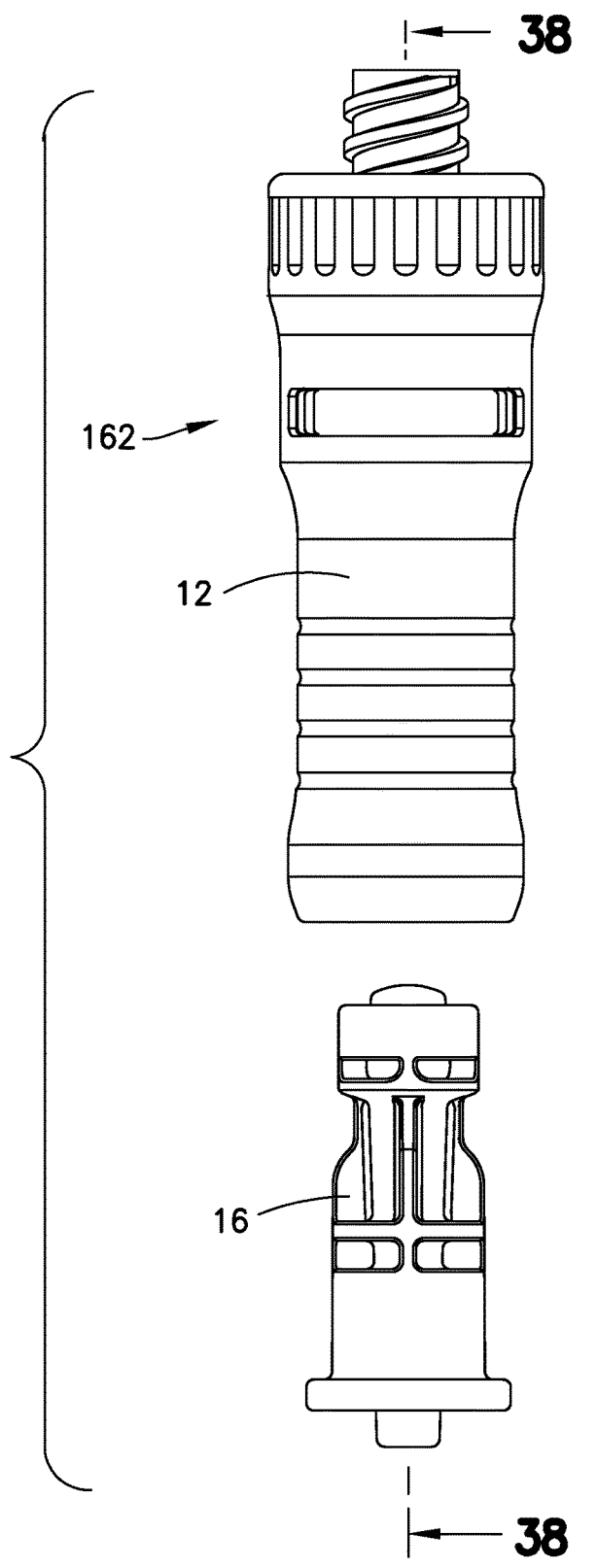
FIG. 37 is a rear view of the system of FIG. 35 according to one aspect of the present invention.
Figure 38:
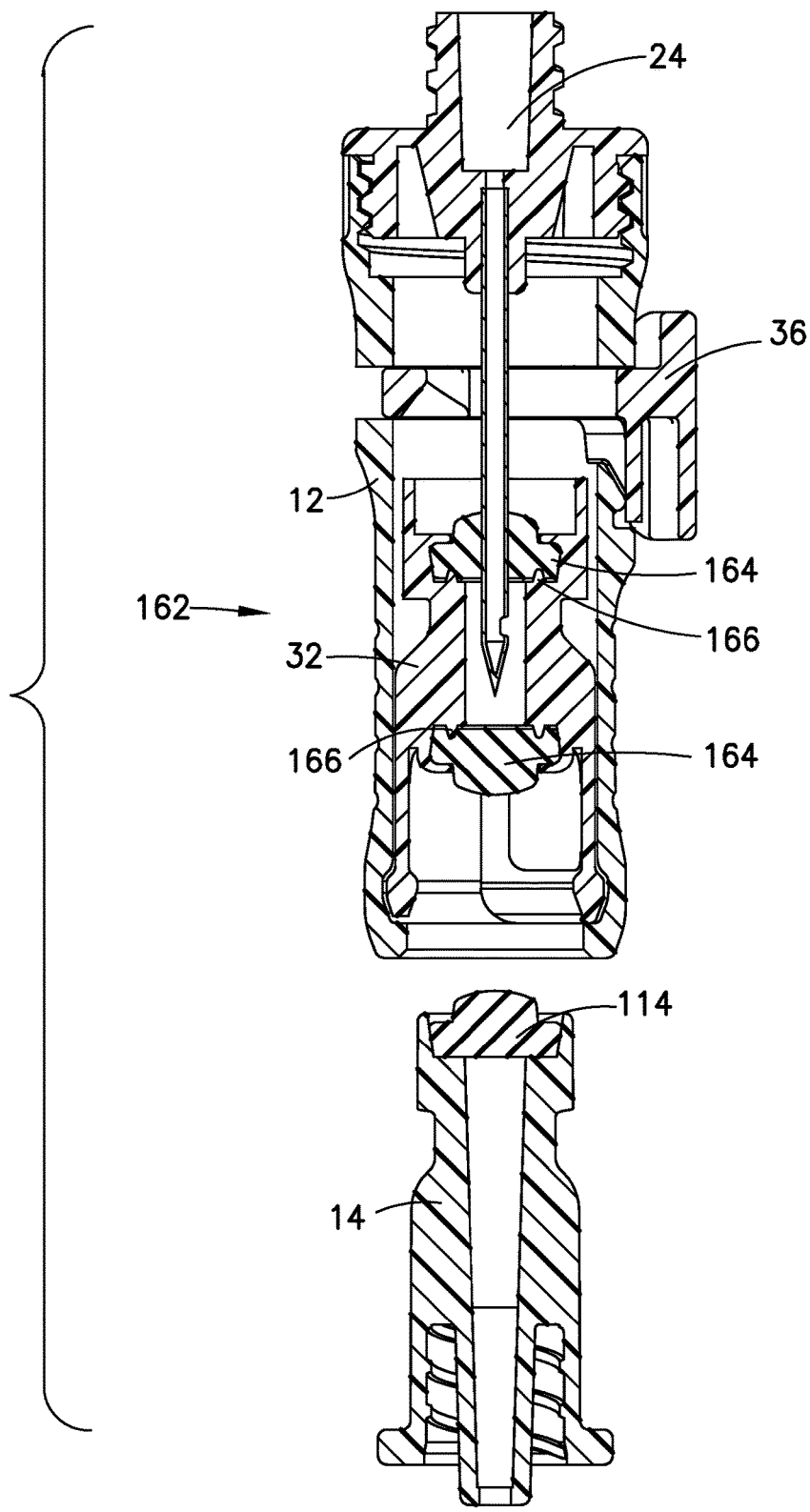
FIG. 38 is a cross-sectional view of the system along line 38-38 in FIG. 37 according to one aspect of the present invention.
Figure 39:
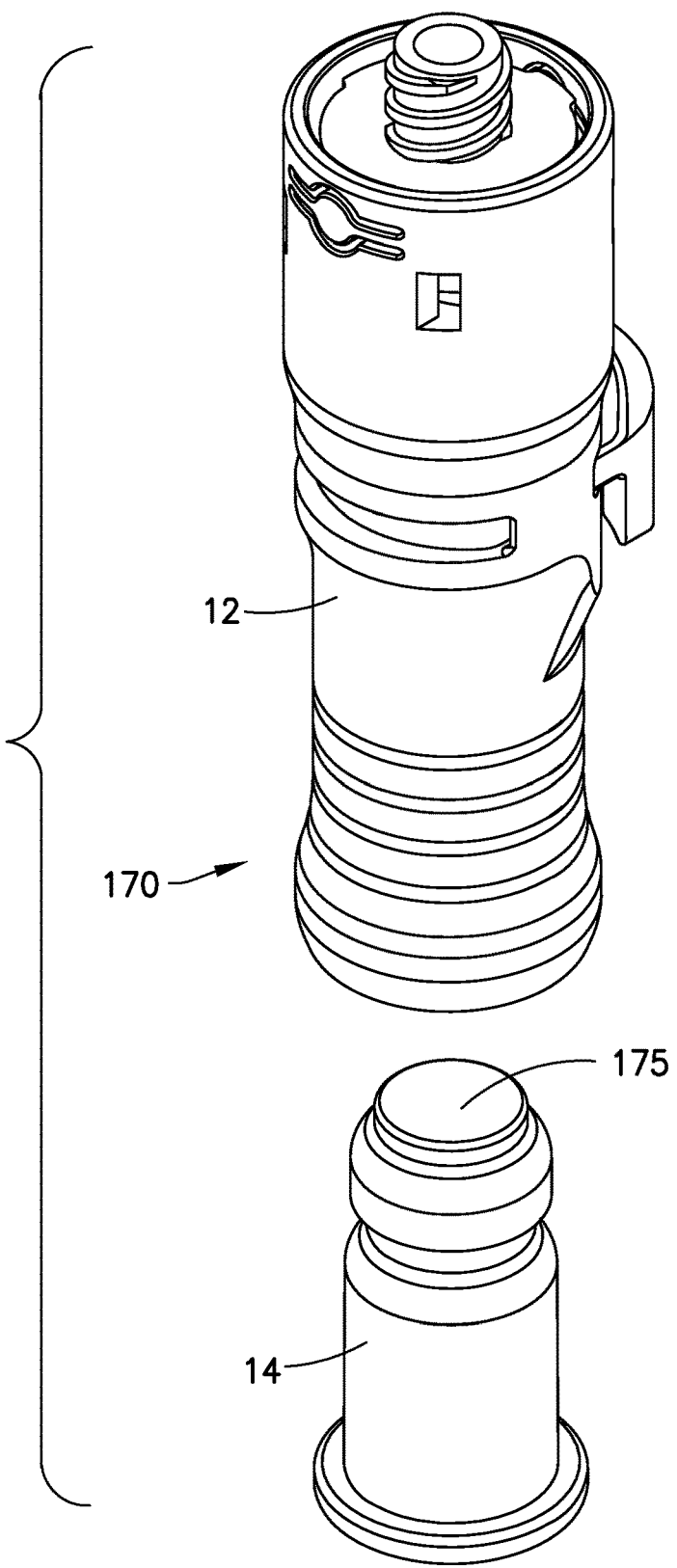
FIG. 39 is a perspective view of a system according to a fifth aspect of the present invention.
Figure 40:
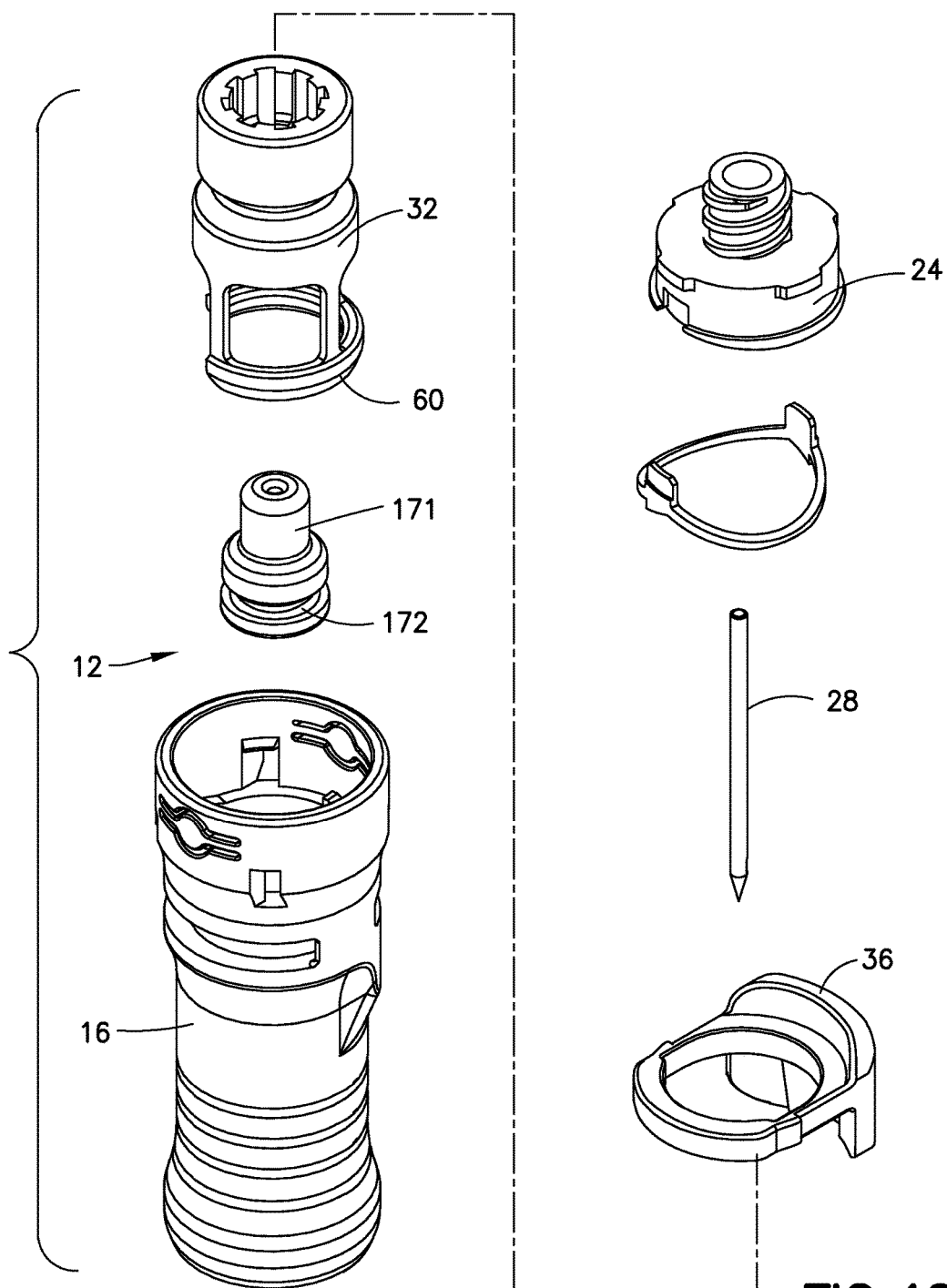
FIG. 40 is an exploded perspective view of the system of FIG. 39 according to one aspect of the present invention.
Figure 41:
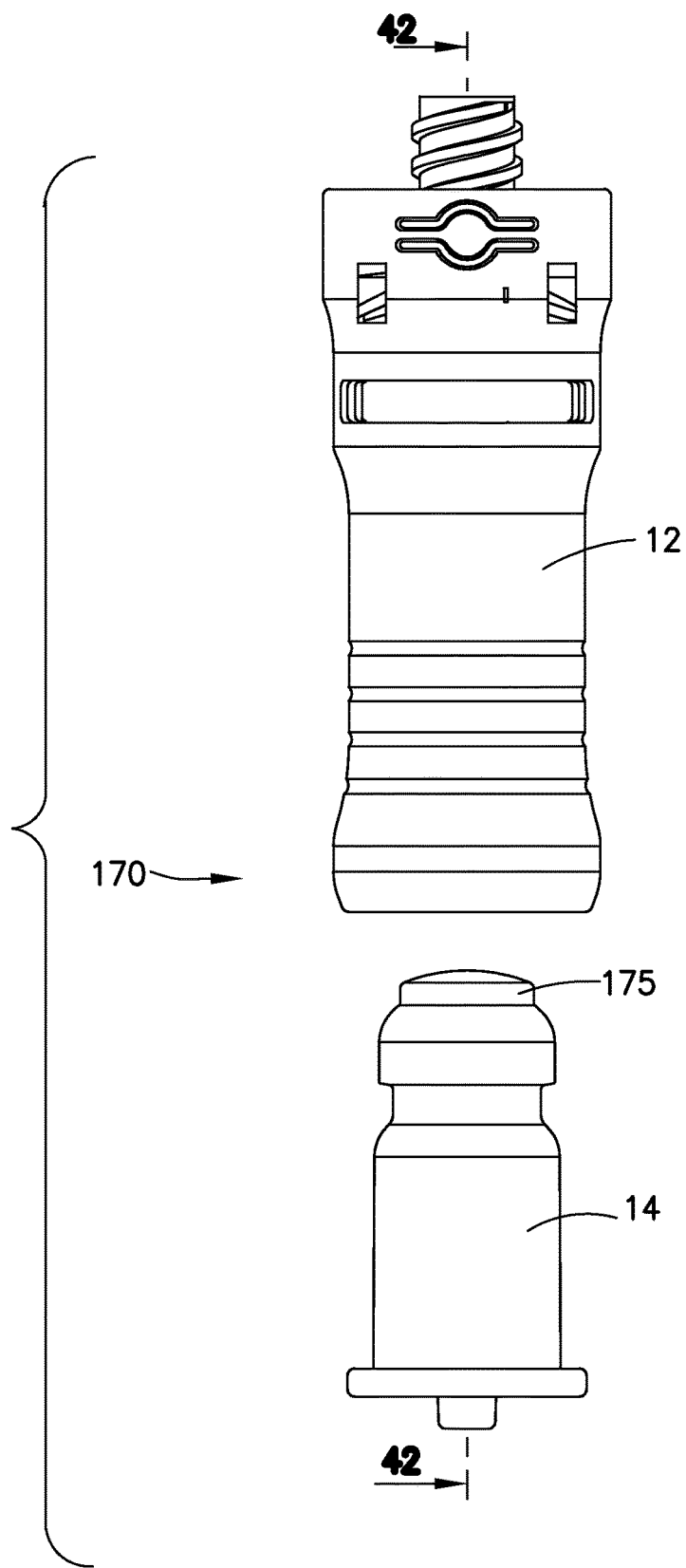
FIG. 41 is a front view of the system of FIG. 39 according to one aspect of the present invention.
Figure 42:
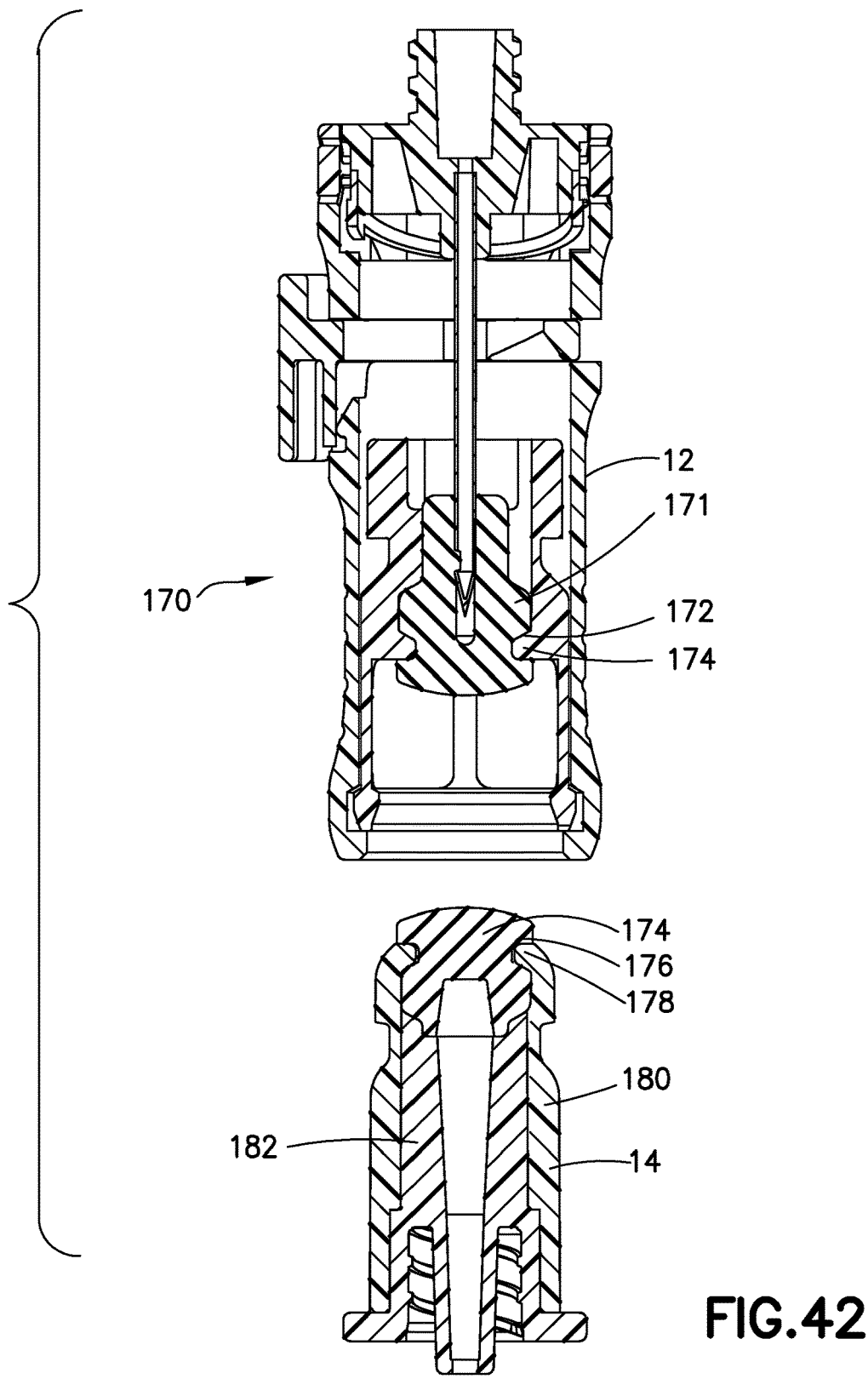
FIG. 42 is a cross-sectional view of the system along line 42-42 in FIG. 41 according to one aspect of the present invention.

Referring to FIGS. 25 and 26, the patient connector 14 and the collet 32 are moved towards the first end 18 of the syringe adapter 12 until the first membrane 34 abuts the syringe attachment 24 of the syringe adapter 12 and/or when the second end 106 of the patient connector 14 abuts the second end 20 of the syringe adapter 12. At this stage, the second connection interface 70 of the collet 32 will be aligned with the lock member 38 of the first connection interface 36 such that the lock member 38 is received within the second connection interface 70. The lock member 38 is biased towards the closed position by the cantilever spring 46 and when the lock member 38 reaches the second connection interface 70, the lock member 38 is free to move into the closed position where a portion of the lock member 38 is positioned within the interior space 22 of the syringe adapter 12.

In the position shown in FIG. 26, the first connection interface 36 is fully mated and locked with respect to the second connection interface 70. In such a position, the syringe adapter 12 is prevented from being disconnected from patient connector 14 due to the engagement between the lock member 38 of the first connection interface 36 and the second connection interface 70. Although the locked engagement between the first connection interface 36 and the second connection interface 70 prevents axial and transverse movement relative to each other, the first connection interface 36 and the second connection interface 70 are free to rotate relative to each other when locked to each other, which advantageously prevents IV line tangling and/or other accidental disengagement or device failure associated with lack of rotation between components. In particular, the patient connector 14 is typically attached to a patient IV line and the rotation of the first connection interface 36 relative to the second connection interface 70 assists in preventing twisting of a patient IV line connected to the patient connector 14. However, the first connection interface 36 and the second connection interface 70 may be provided with a keyed surface arrangement to prevent such relative rotation if desired.

Referring again to FIGS. 17-26, in order to disconnect the first connection interface 36 from the second connection interface 70, the button 44 of the lock member 38 of the first connection interface 36 is engaged by a user and pushed radially inward to transition the lock member 38 from the closed position to the open position. The patient connector 14 can then be removed from the interior space 22 of the syringe adapter 12 in the reverse order of the steps to connect the syringe adapter 12 to the patient connector 14. When the second connection interface 70 is separated from the first connection interface 36, the lock member 38 is moved to the closed position. The patient connector 14 cannot be separated from the syringe adapter 12 until the collet 32 is returned to the first position shown in FIG. 22 where the locking member 60 of the collet 32 can expand radially outward into the annular recess 64 of the housing 16 thereby allowing separation of the patient connector 14 from the collet 32. Although not shown, the syringe adapter 12 may be provided with one or more indication arrangements to provide a visual, tactile, or auditory indication to a user during connection of the syringe adapter to a mating component.

The system 10 described above as well as further aspects of the system 10 described below may include one or more arrangements to reduce the friction between the first membrane 34 and the cannula 28. Such arrangements may be a lubricant provided on or within the first membrane 34 and/or on the cannula 28. The lubricant may be a silicone-based lubricant, although any other suitable lubricant, coating, layer, material, etc. may be utilized. The first membrane 34 and/or needle 28 may be made from a lubricious or friction-reducing material, coated with a lubricant, and/or impregnated with a lubricant. The arrangement to reduce the friction between the first membrane 34 and the needle 28 may be a wet and/or dry lubrication system.

Referring to FIGS. 27-30, a further aspect of a system 140 for the closed transfer of fluids is shown. The system 140 shown in FIGS. 27-30 is similar to the system 10 shown in FIGS. 1-26 and discussed above. In the system 140 shown in FIGS. 27-30, however, the locking member 60 of the collet 32 is ring-shaped and defines only one opening 142 extending transversely to a longitudinal axis of the collet 32. Further, the system 140 includes a disconnection prevention mechanism 144 that prevents the accidental disconnection of a syringe from the syringe adapter 12. When the collet 32 is fully displaced toward the first end 18 of the syringe adapter 12, the collet 32 may engage the disconnection prevention mechanism 144 to substantially prevent disconnection of a syringe from the syringe adapter 12 by allowing the syringe attachment 24 to rotate freely. The patient connector 14 may also include a membrane seat 146 having at least one protrusion and an upper rim 148 that receives and engages a corresponding shaped portion of the second membrane 114. The second membrane 114 may be secured to the membrane seat 146 via ultrasonic welding, by swaging the seat 146, or by adhesive, although other suitable attachment arrangements may be utilized.

Referring to FIGS. 31-34, a further aspect of a system 152 for the closed transfer of fluids is shown. The system 152 shown in FIGS. 31-34 is similar to the system 10 shown in FIGS. 1-26 and discussed above. In the system 152 shown in FIGS. 31-34, however, a first membrane 154 is generally T-shaped with a flange portion 156 that is received within a corresponding seat 158 defined by the collet 32.

Referring to FIGS. 35-38, a further aspect of a system 162 for the closed transfer of fluids is shown. The system 162 shown in FIGS. 35-38 is similar to the system shown in FIGS. 1-26 and discussed above. In the system 162 shown in FIGS. 35-38, however, the collet 32 receives a pair of spaced apart membranes 164 defining a space therebetween within the collet 32. The pair of membranes 164 is received by first and second membrane seats 166, respectively.

Referring to FIGS. 39-42, a further aspect of a system 170 for the closed transfer of fluids is shown. The system 170 shown in FIGS. 39-42 is similar to the system 10 shown in FIGS. 1-26 and discussed above. In the system 170 shown in FIGS. 39-42, however, a first membrane 171 defines an annular recess 172 that is received by a corresponding projection 174 of the collet 32. Further, the first membrane 171 is contoured and received by a correspondingly contoured portion of the collet 32. A second membrane 175 also defines an annular recess 176 that is received by a corresponding projection 178 of the patient connector 14. The body 104 of the patient connector 14 is defined by an outer portion 180 and an inner portion 182 that are secured to each other via any suitable securing arrangement, such as ultrasonic welding, spin welding, or laser welding.

Figures 43A, 43B:
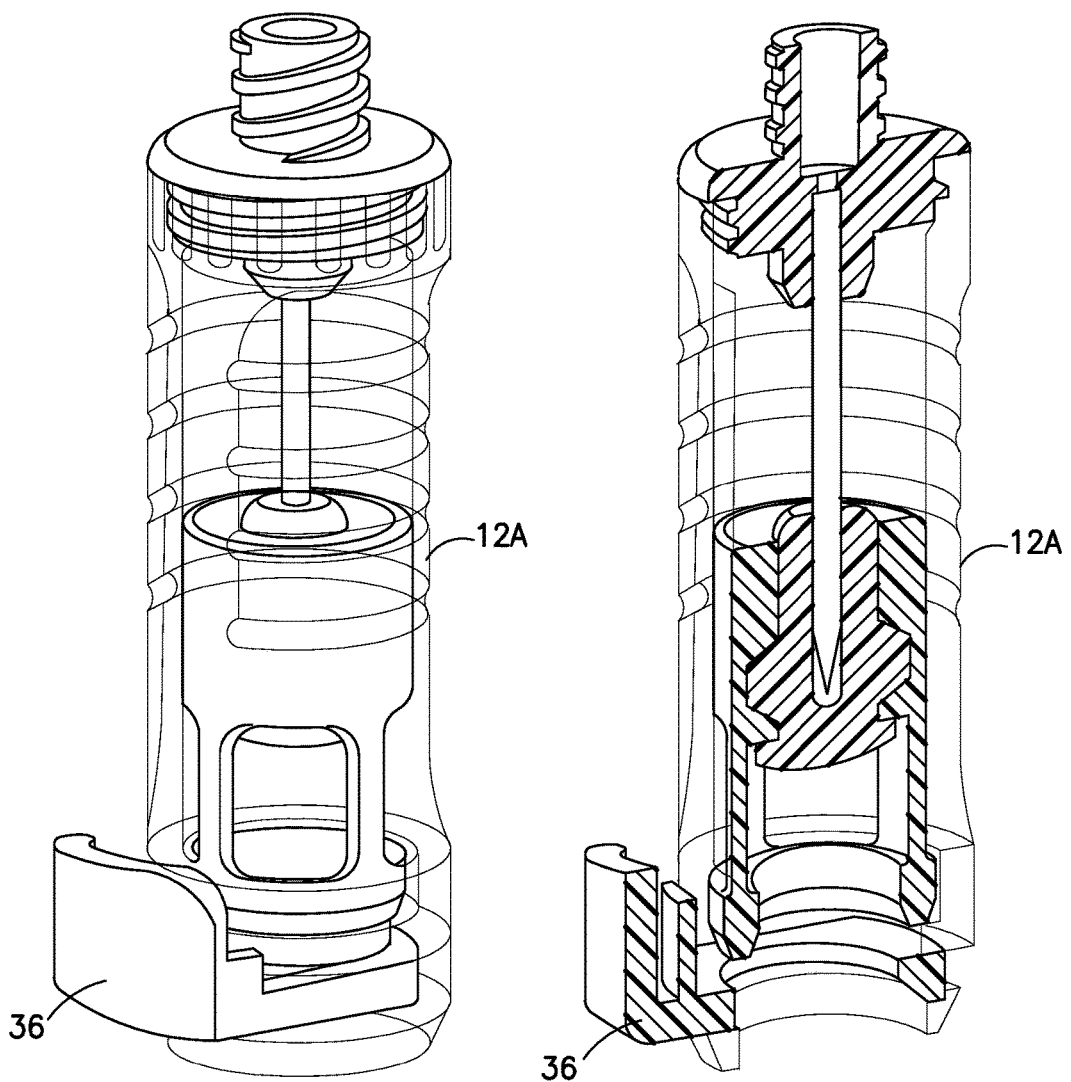
FIG. 43A is a perspective view of a syringe adapter according to yet another aspect of the present invention.
FIG. 43B is a cross-sectional view of the syringe adapter of FIG. 43A according to one aspect of present invention.
Figure 44:
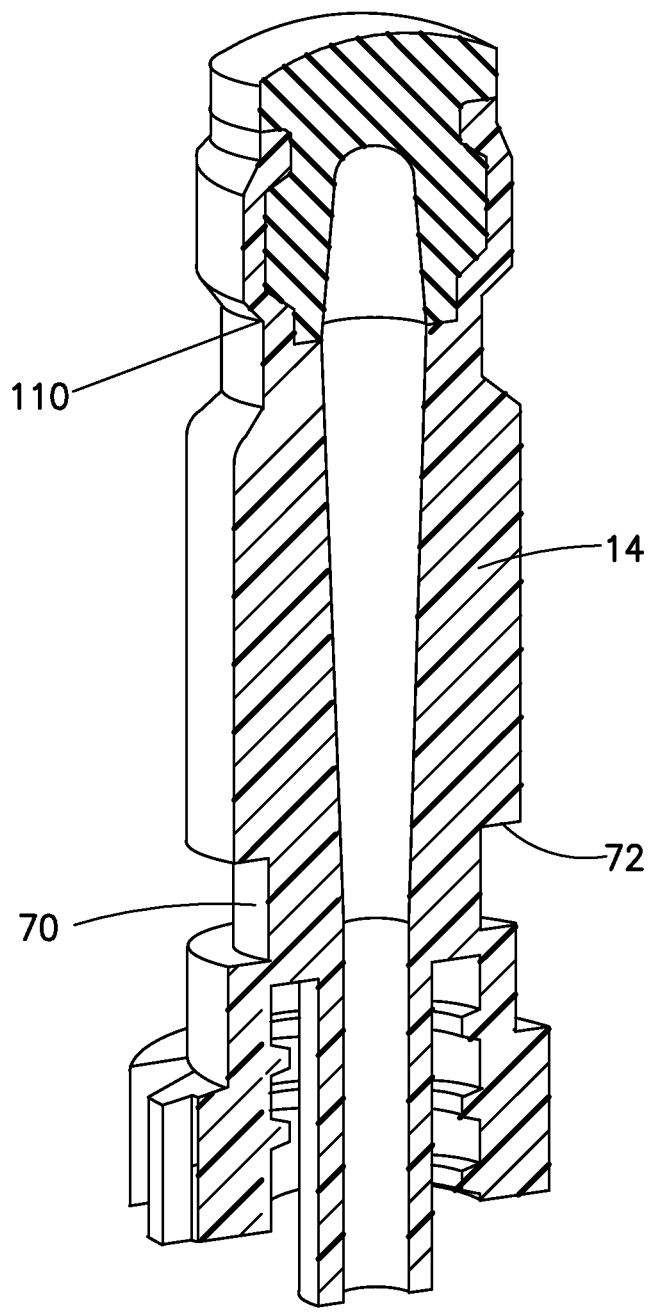
FIG. 44 is a cross-sectional view of a patient connector for use in connection with the syringe adapter of FIG. 43A according to one aspect of present invention.

Referring to FIGS. 43A, 43B, and 44, another aspect of a syringe adapter 12A is shown. The syringe adapter 12A shown in FIGS. 43A, 43B, and 44 is similar to the syringe adapter 12 shown in FIGS. 1-11 and discussed above. The syringe adapter 12A shown in FIGS. 43A, 43B, and 44, however, provides the first connection interface 36 at or near the second end 20 of the syringe adapter 12A. Further, rather than providing the second connection interface 70 on the collet 32, the patient connector 14 includes both the collet interface 110 as well as the second connection interface 70. The syringe adapter 12A operates in the same manner as described above in connection with FIGS. 1-26.

Figure 10:
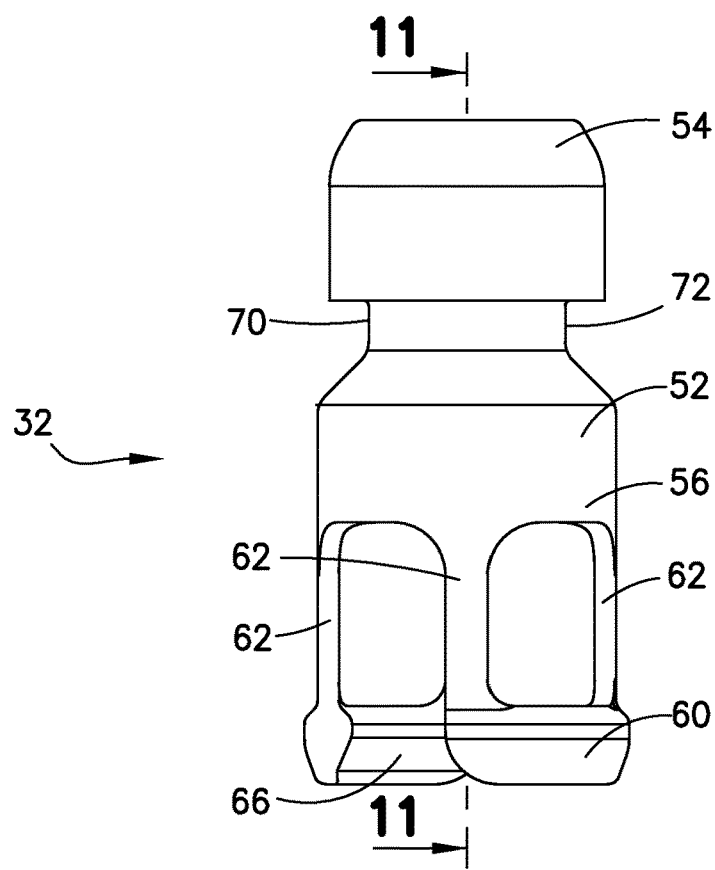
FIG. 10 is a front view of the collet of FIG. 2 according to one aspect of the present invention.
Figure 11:
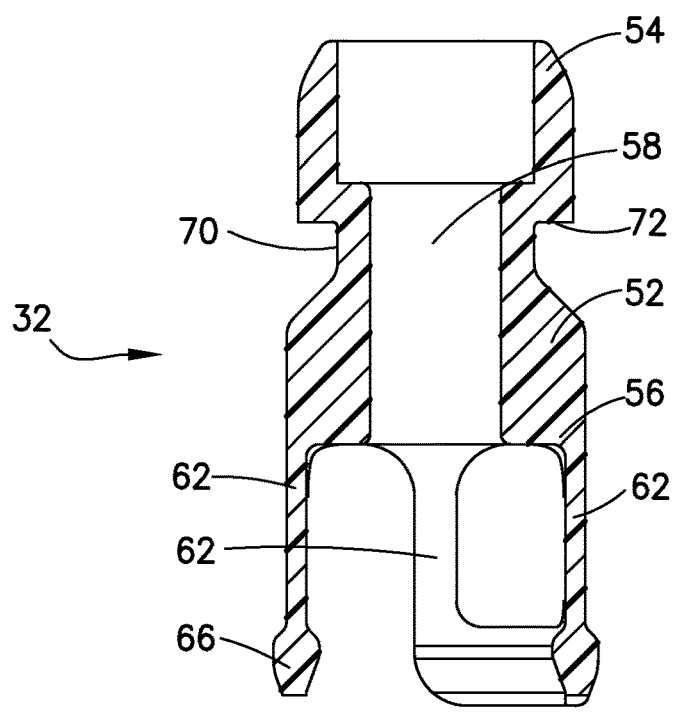
FIG. 11 is a cross-sectional view of the collet along line 11-11 in FIG. 10 according to one aspect of the present invention.
Figure 12:
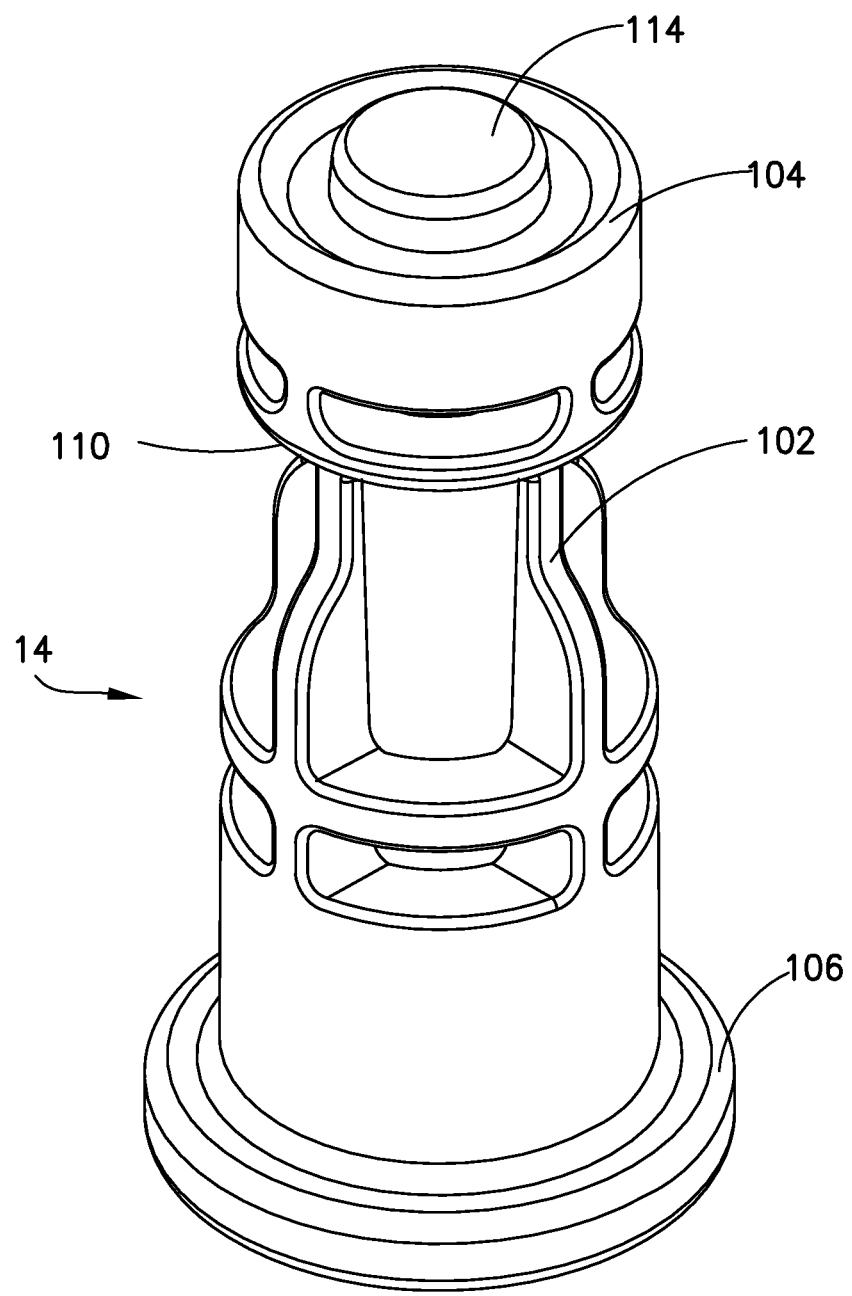
FIG. 12 is a perspective view of a patient connector of the system shown in FIG. 1 according to one aspect of the present invention.
Figure 13:
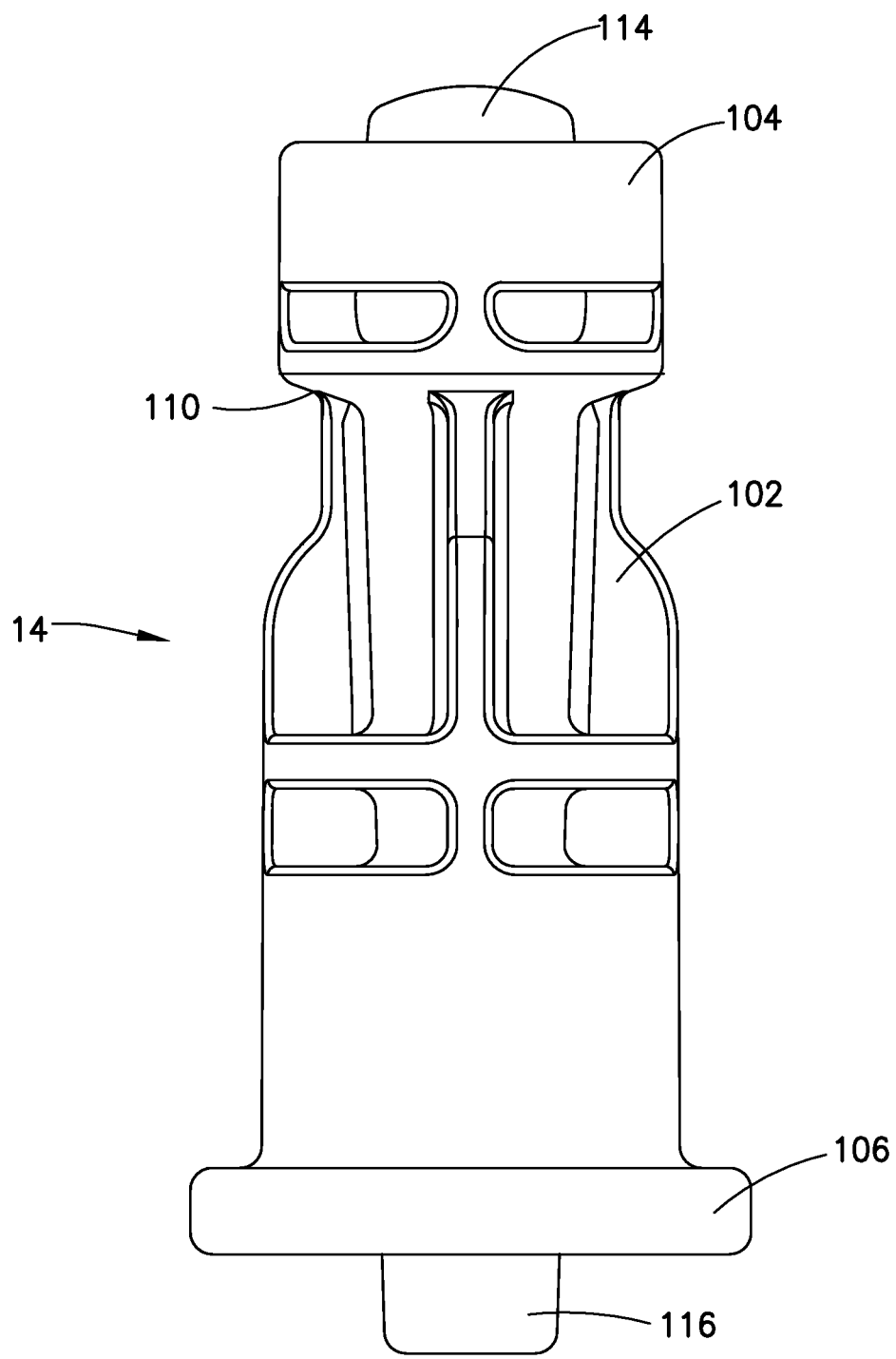
FIG. 13 is a front view of the patient connector of FIG. 12 according to one aspect of the present invention.
Figure 14:
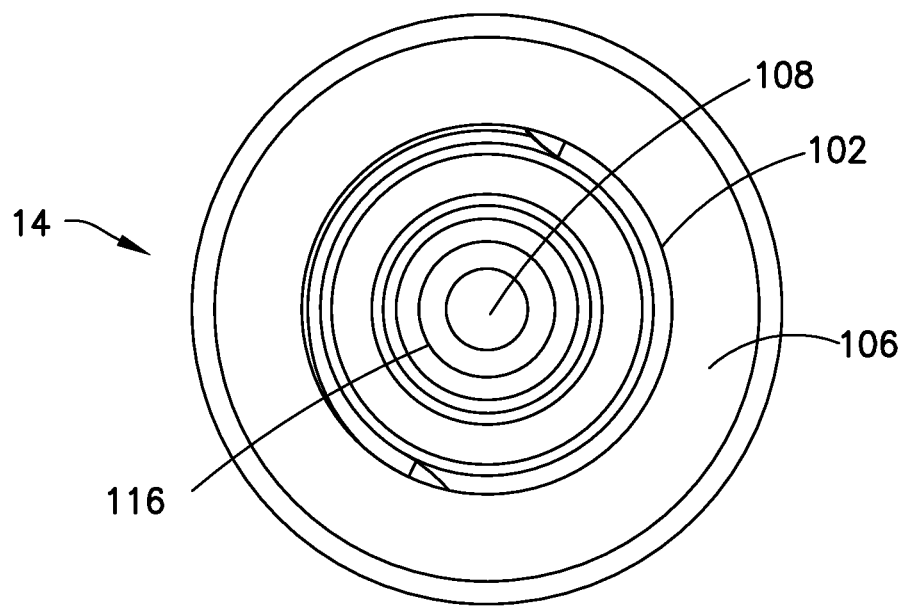
FIG. 14 is bottom view of the patient connector of FIG. 12 according to one aspect of the present invention.
Figure 15:
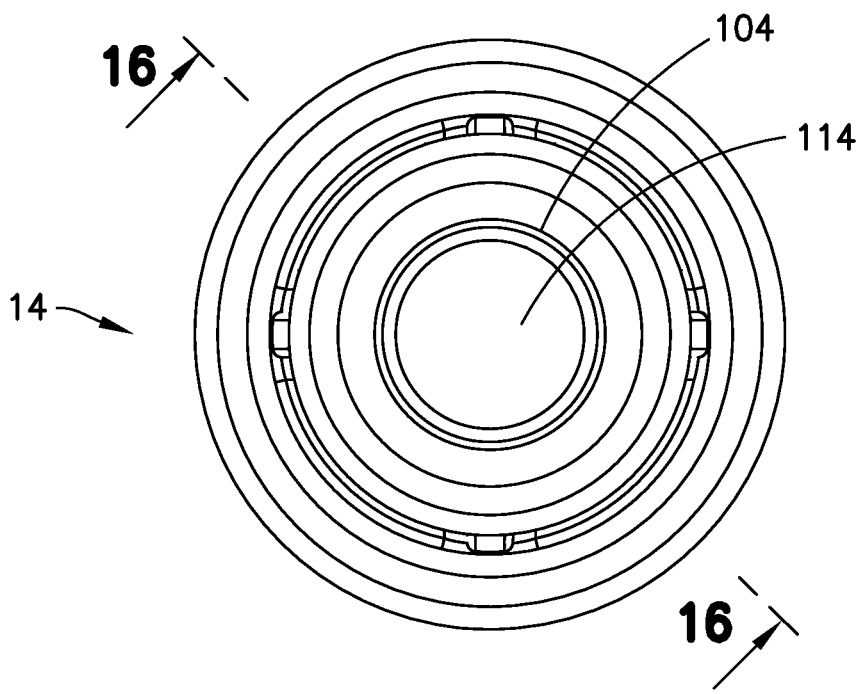
FIG. 15 is a top view of the patient connector of FIG. 12 according to one aspect of the present invention.
Figure 16:
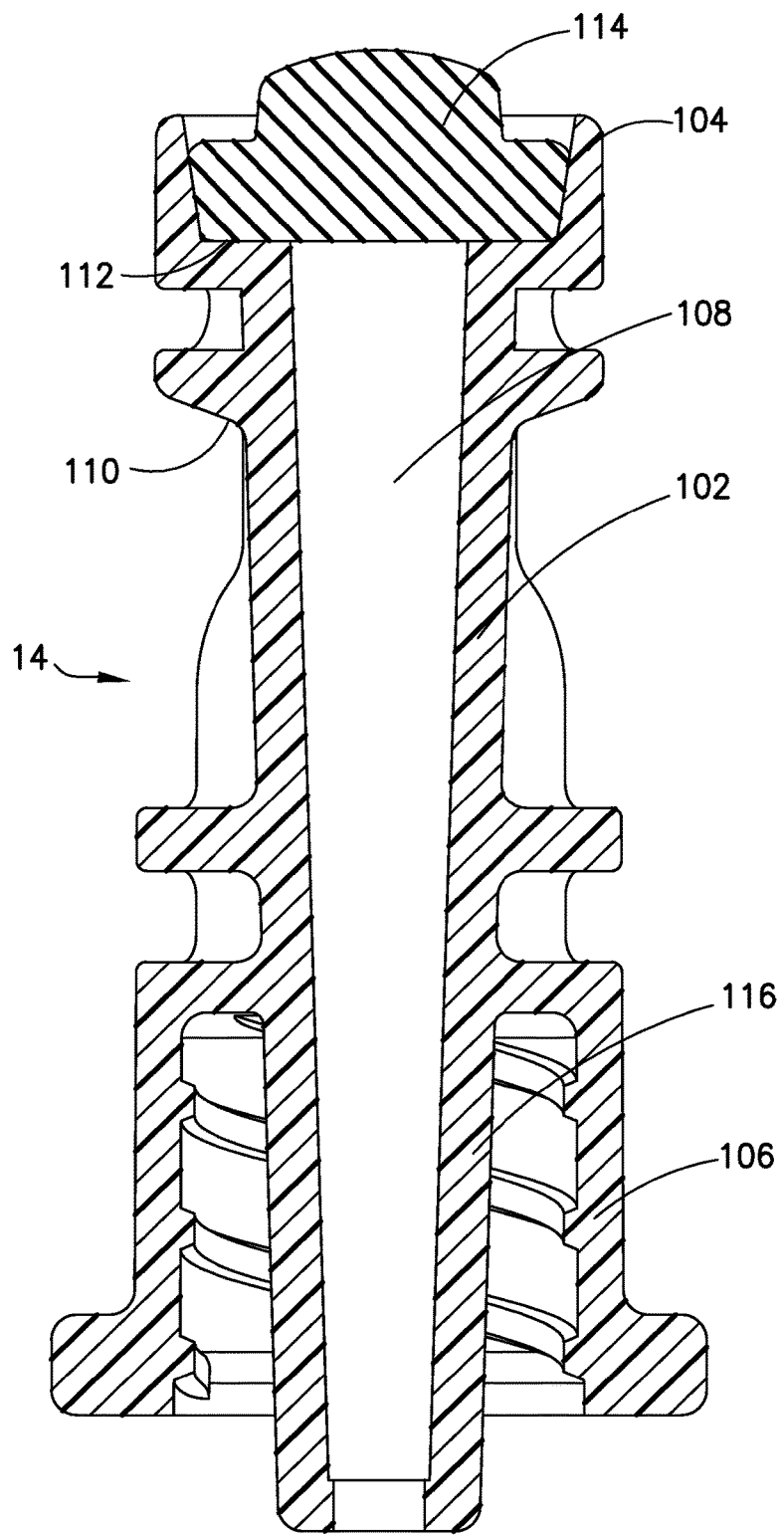
FIG. 16 is a cross-sectional view of the patient connector along line 16-16 in FIG. 15 according to one aspect of the present invention.
Figure 45A:
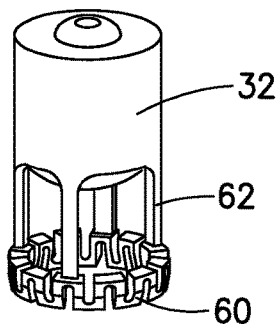
FIGS. 45A-45F are perspective views of a collet according to further aspects of the present invention.
Figure 45B:
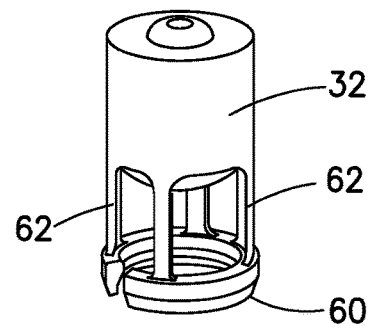
Figure 45C:
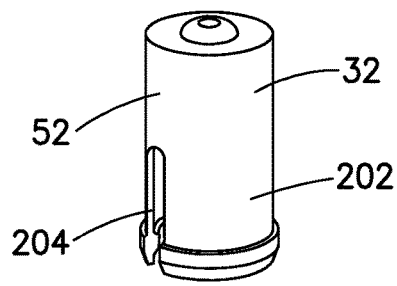
Figure 45D:
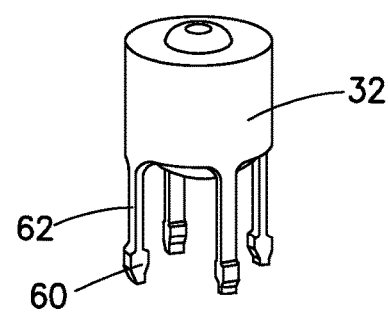
Figure 45E:
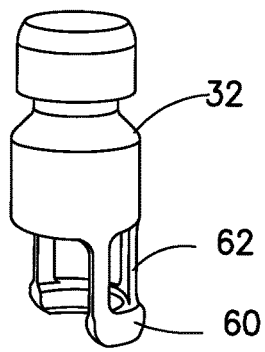
Figure 45F:
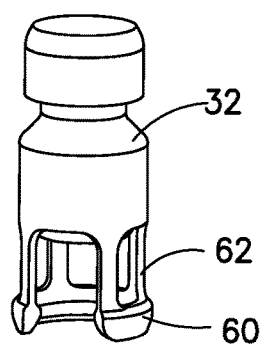

Referring to FIGS. 45A-45F, further aspects of the collet 32 of FIGS. 9-11 are shown. In FIG. 45A, the locking member 60 of the collet 32 is continuous and ring-shaped and defines a plurality of notches that are configured to permit the locking member 60 to expand radially outward. In FIG. 45B, the locking member 60 is ring-shaped and defines a small slit extending transversely to a longitudinal axis of the collet. In FIG. 45C, the body 52 of the collet 32 is secured to the locking member 60 via an extension portion 202 of the body 52 and the locking member 60 is ring-shaped and defines a slit 204 configured to permit the locking member 60 to expand radially outward. In FIG. 45D, the plurality of arms 62 each includes a respective locking member 60 that is formed by an enlarged head portion at the end of each arm 62. In FIG. 45E, the locking member 60 is half ring-shaped. In FIG. 45F, the locking member 60 is arcuate and defines a single opening.

Figure 46:
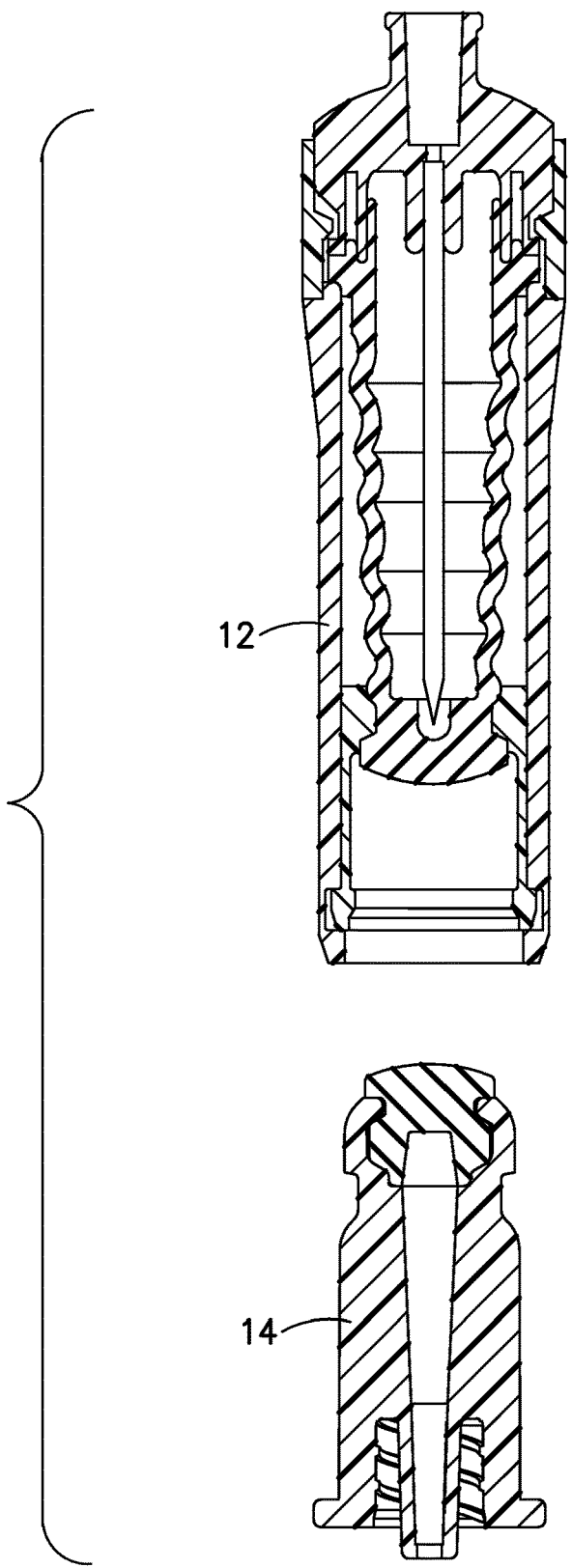
FIG. 46 is a cross-sectional view of a system according to another aspect of the present invention.

Referring to FIG. 46, a further aspect of the syringe adapter 12 of FIGS. 1-11 is shown. In particular, the first membrane 34 is generally sleeve-like and is configured to retract upon engagement with the patient connector 14.

Figure 47:
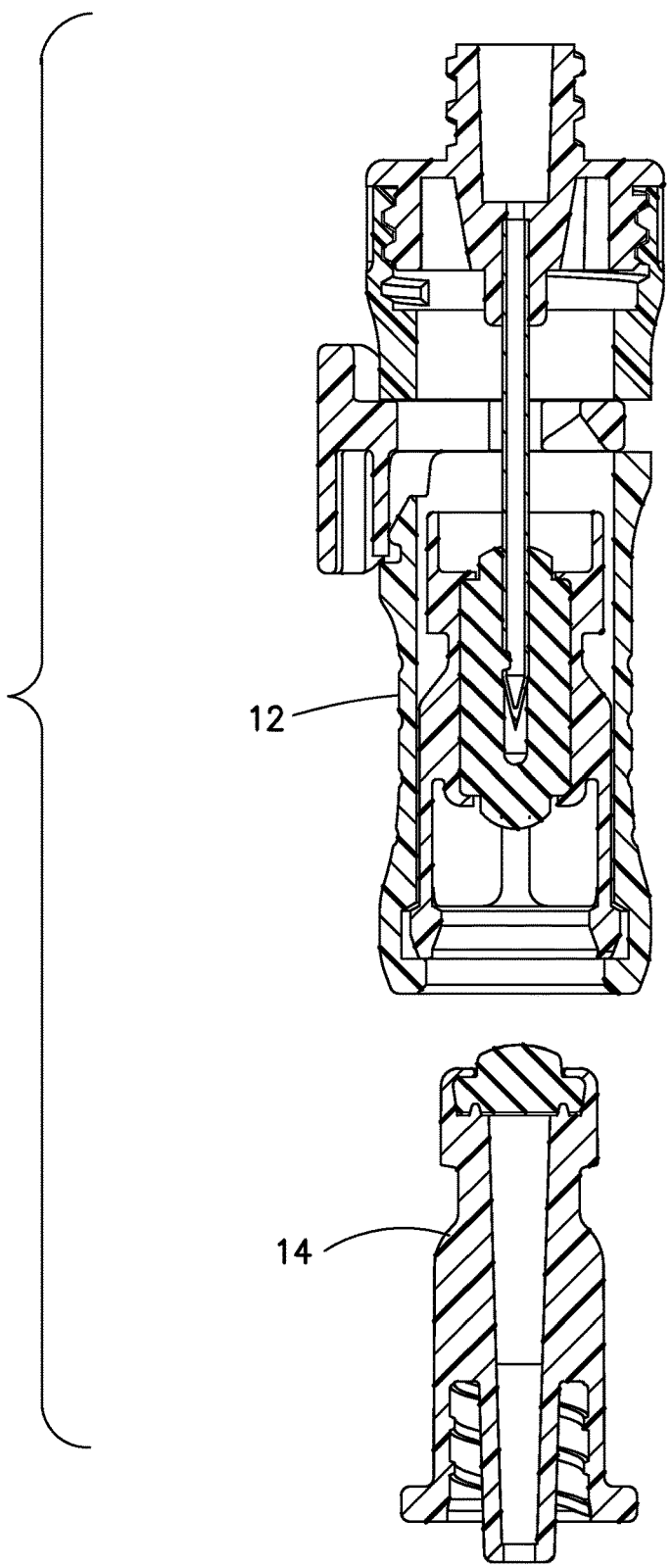
FIG. 47 is a cross-sectional view of a system according to yet another aspect of the present invention.
Figure 48A:
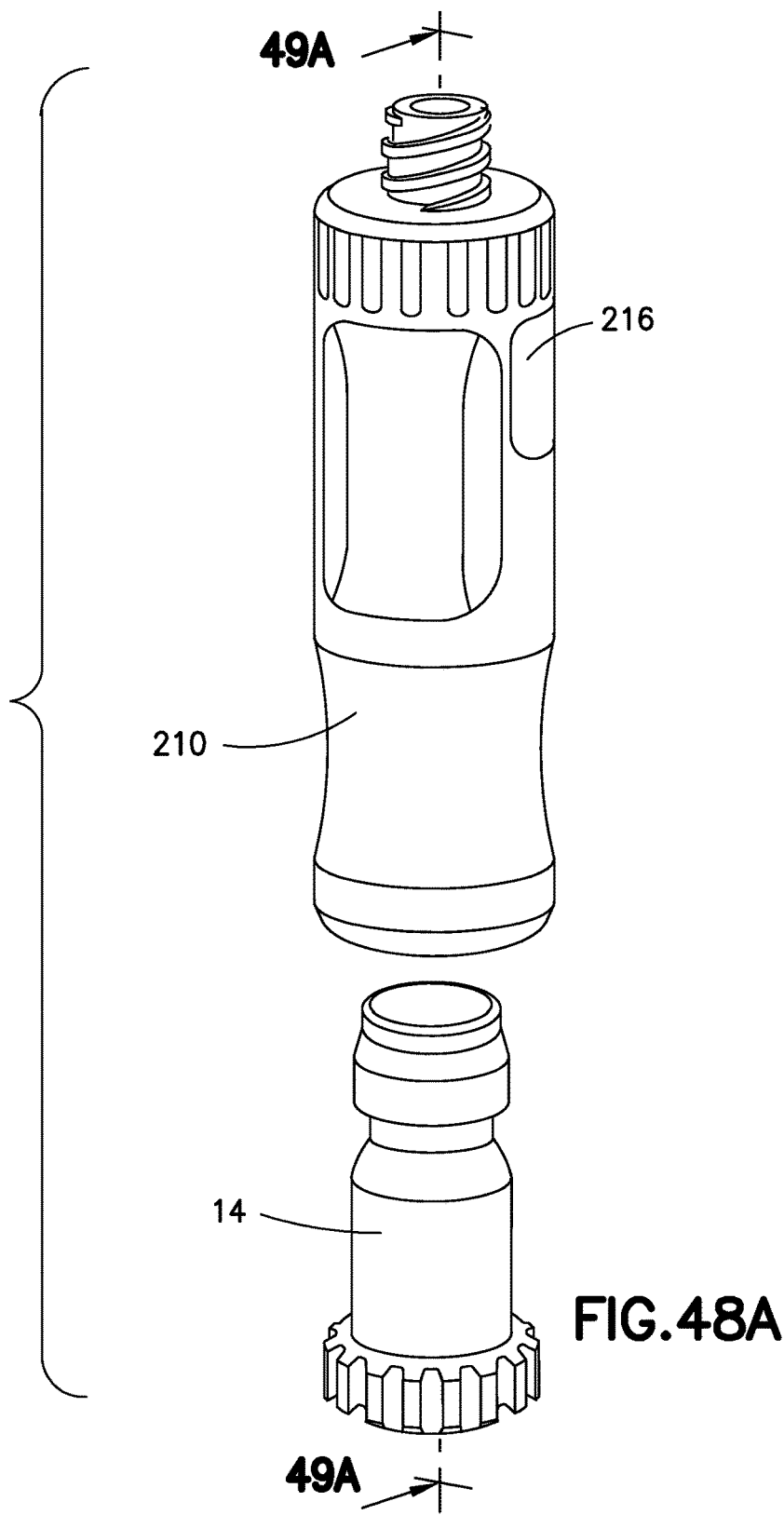
FIG. 48A is a perspective view of a system according to yet a further aspect of the present invention, showing a syringe adapter disconnected from a patient connector.
Figure 48B:
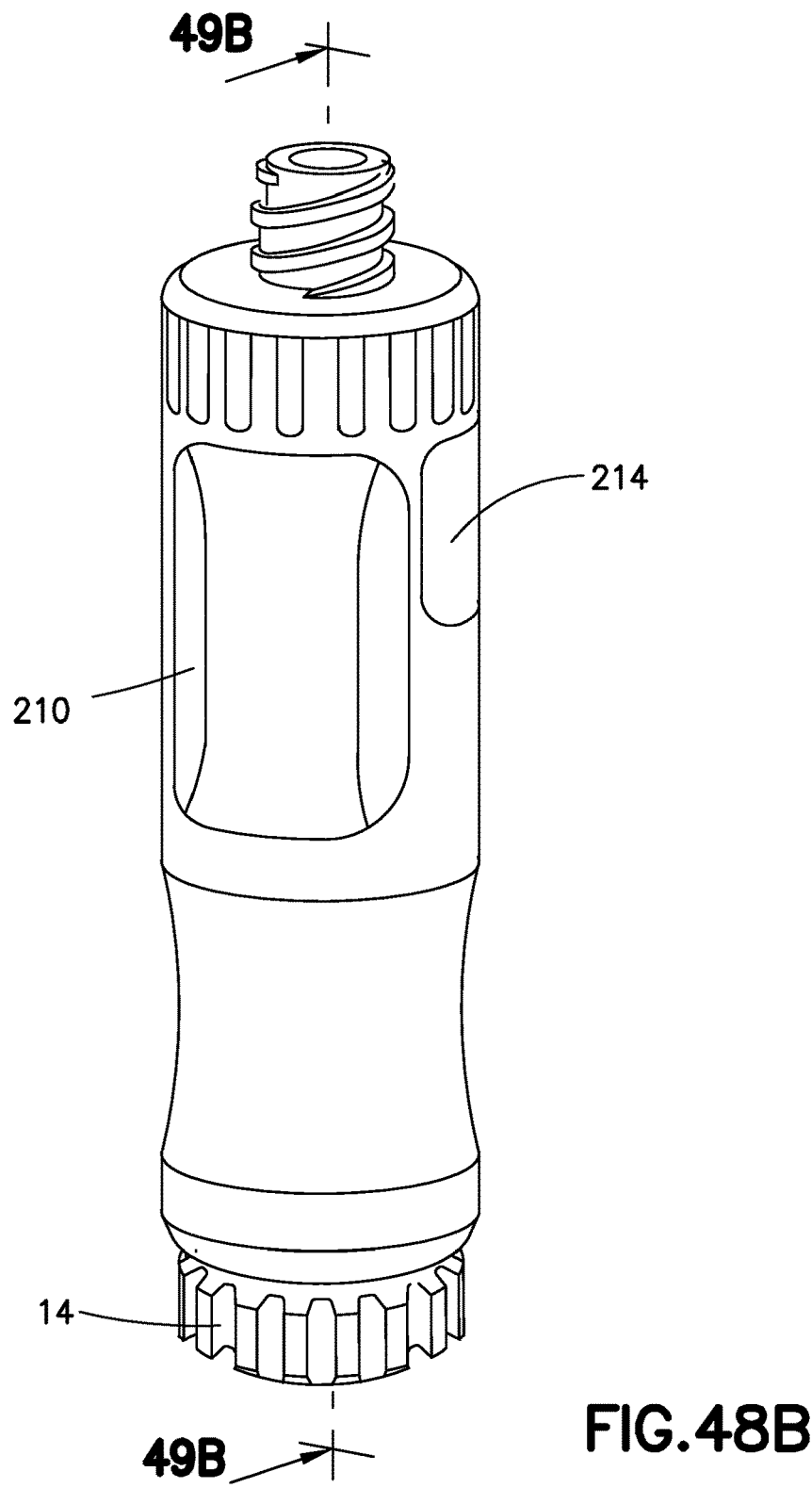
FIG. 48B is a perspective view of the system of FIG. 48A showing a syringe adapter connected to a patient connector according to another aspect of the present invention.
Figure 49A:
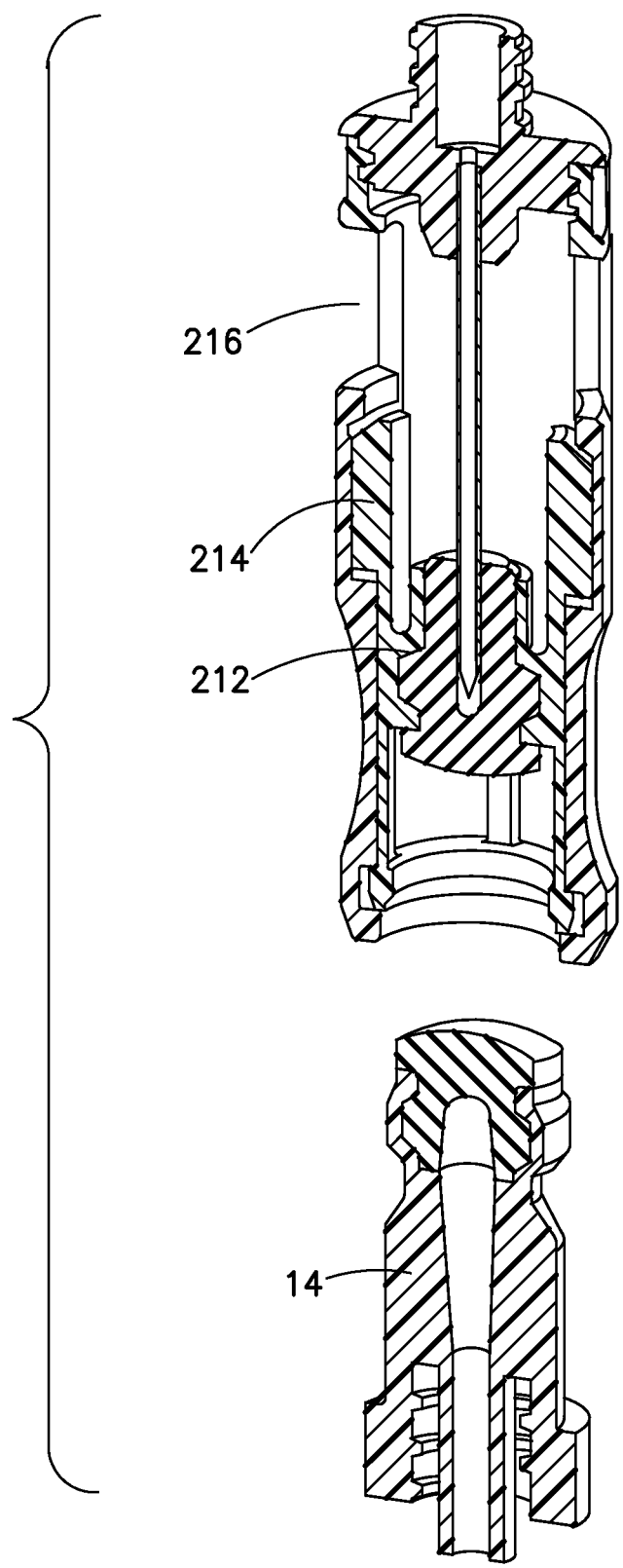
FIG. 49A is a cross-sectional view along line 49A-49A in FIG. 48A according to one aspect of the present invention.
Figure 49B:
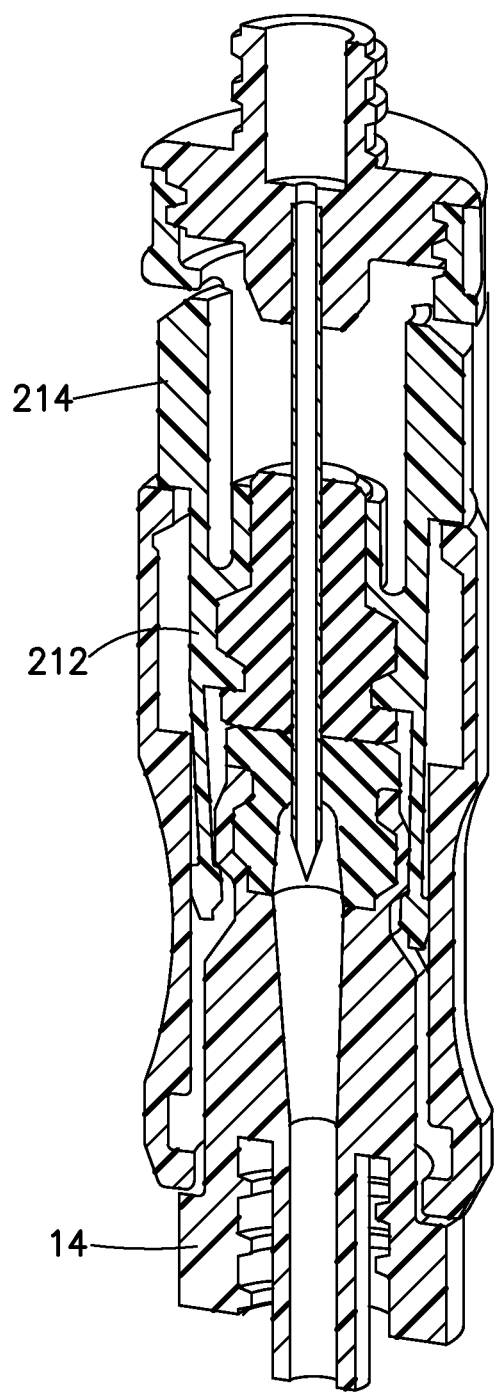
FIG. 49B is a cross-sectional view along line 49B-49B in FIG. 48B according to one aspect of the present invention.
Figure 50A:
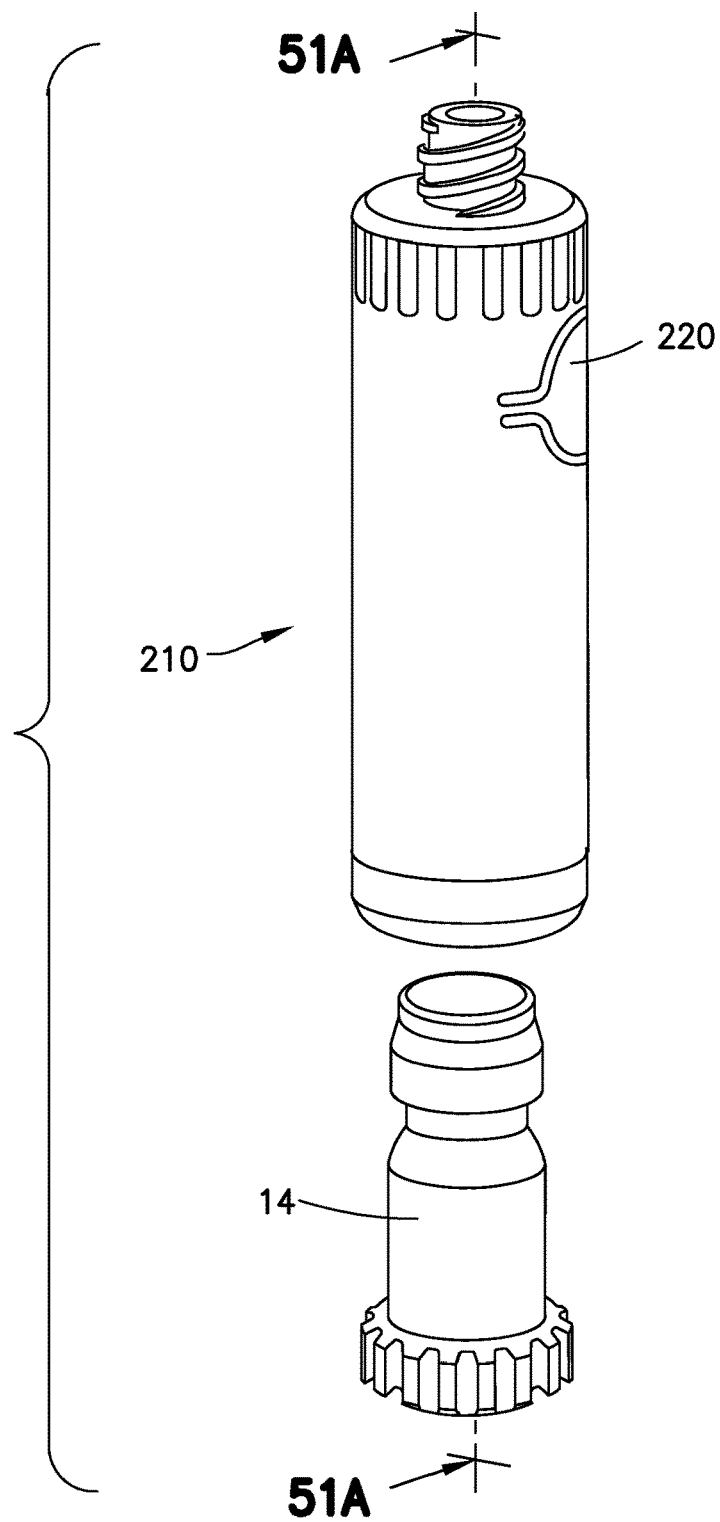
FIG. 50A is a perspective view of a system according to a further aspect of the present invention, showing a syringe adapter disconnected from a patient connector.
Figure 50B:
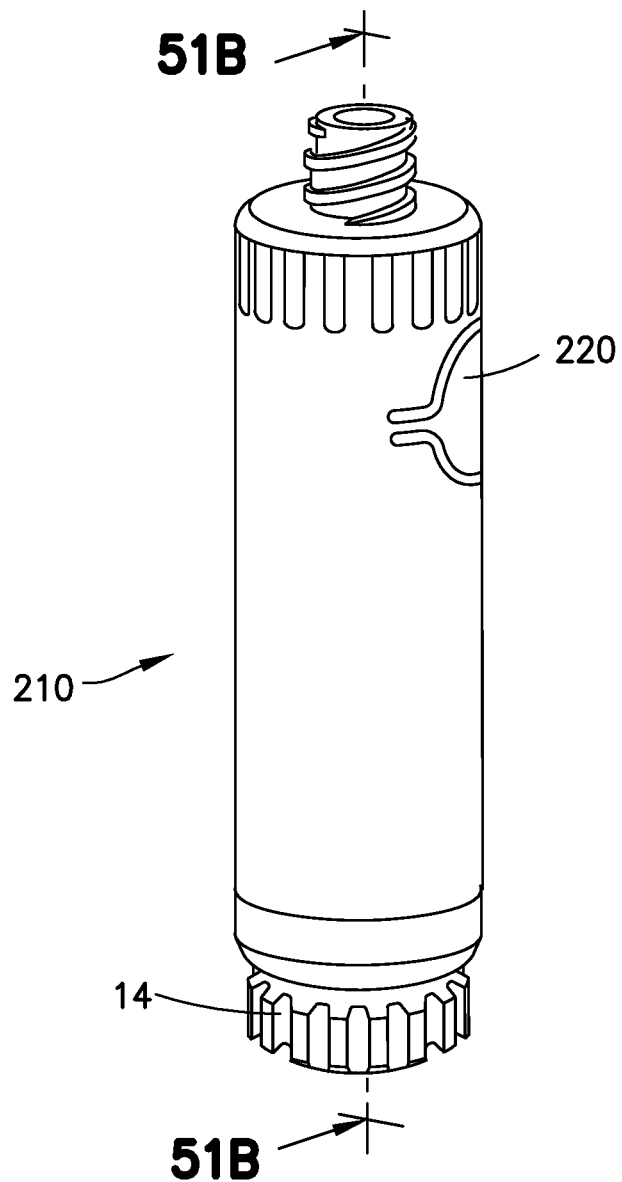
FIG. 50B is a perspective view of the system of FIG. 50A showing a syringe adapter connected to a patient connector according to another aspect of the present invention.
Figure 51A:
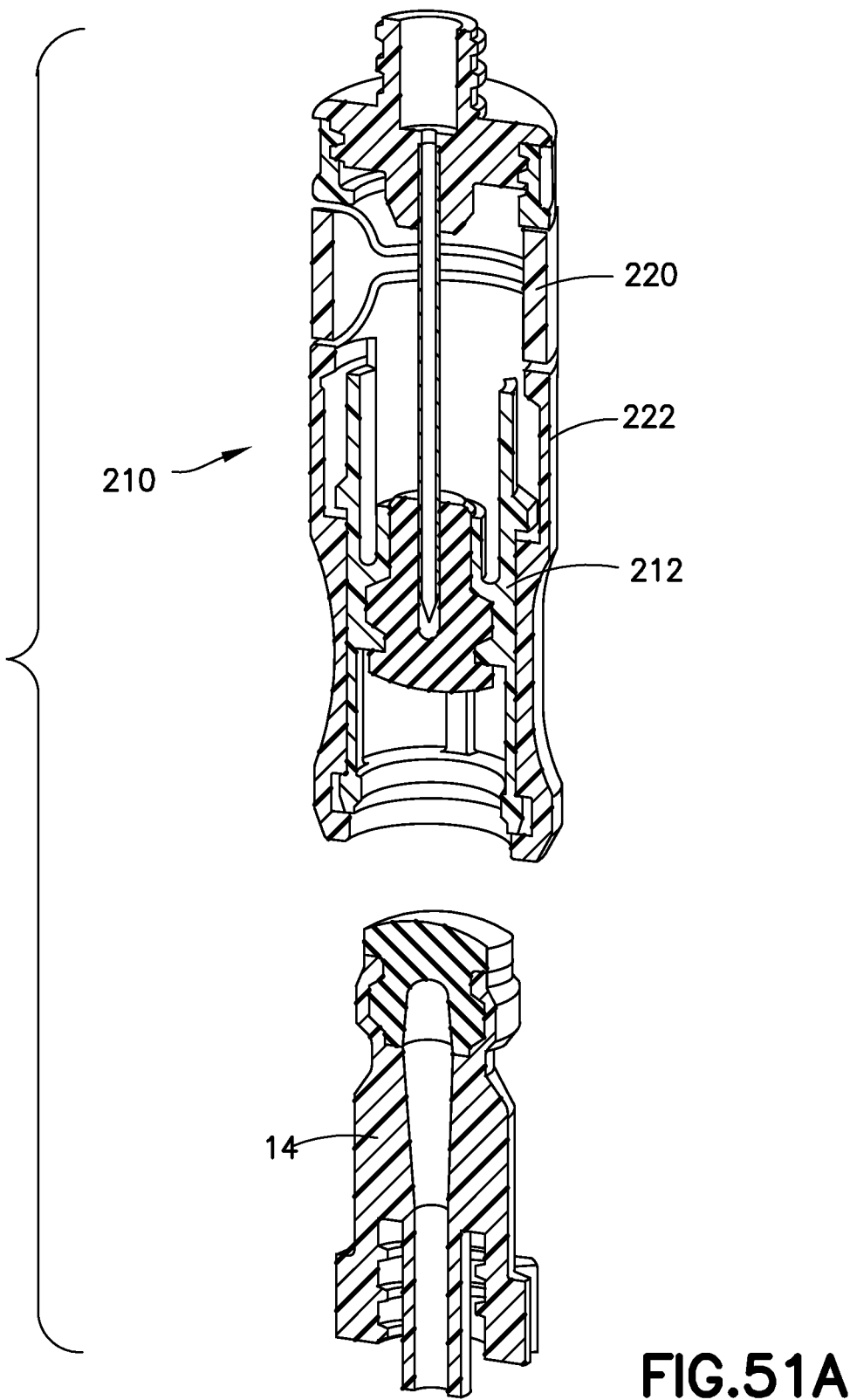
FIG. 51A is a cross-sectional view along line 51A-51A in FIG. 50A according to one aspect of the present invention.
Figure 51B:
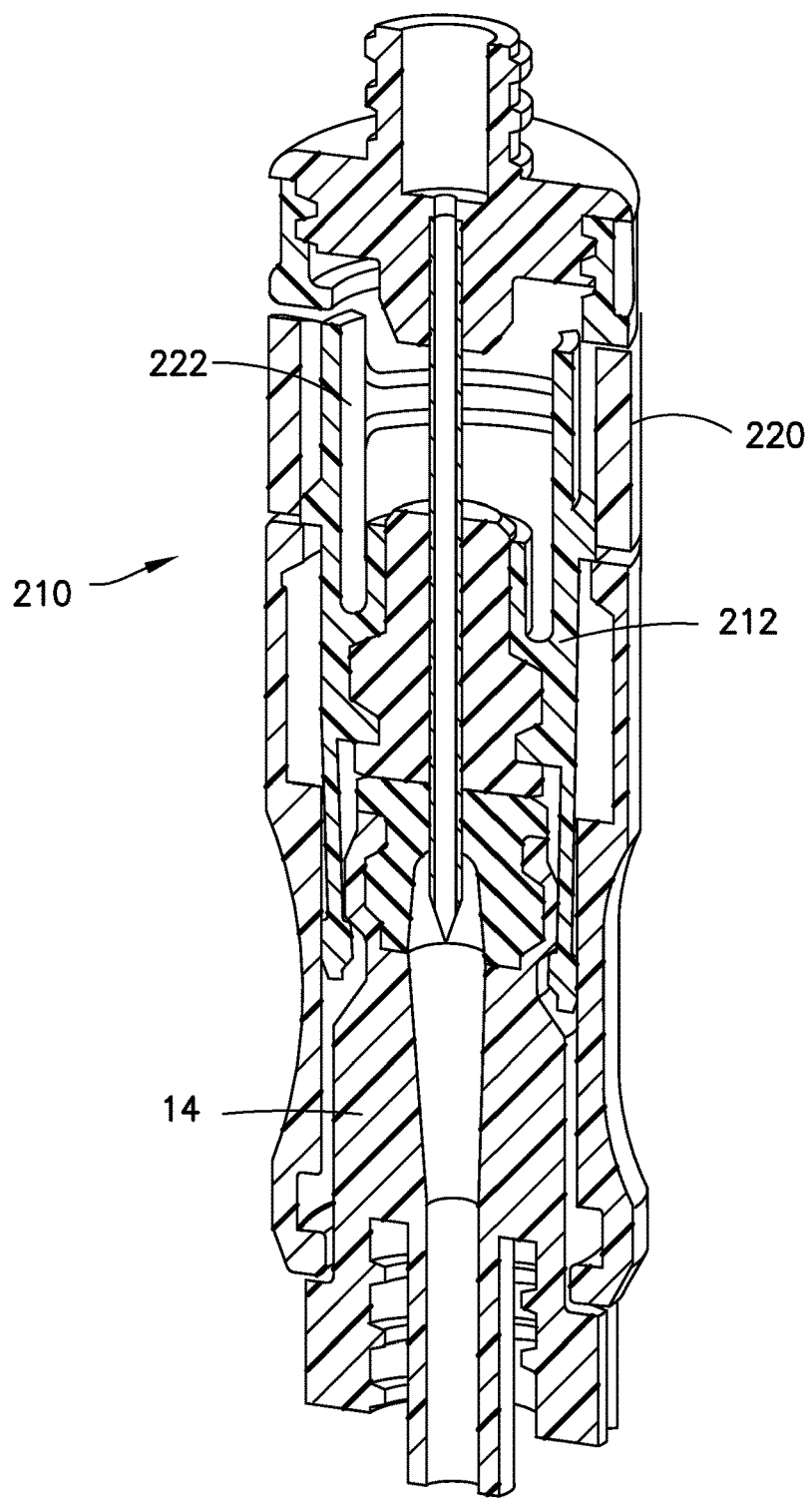
FIG. 51B is a cross-sectional view along line 51B-51B in FIG. 50B according to one aspect of the present invention.

Referring to FIG. 47, a further aspect of the syringe adapter 12 of FIGS. 1-11 is shown. In particular, the first membrane 34 is generally cylindrical with convex portions at the first and second ends of the first membrane 34.

Referring to FIGS. 48A-49B, a further aspect of the syringe adapter 12 of FIGS. 1-11 is shown. A syringe adapter 210 shown in FIGS. 48A-49B includes a collet 212 having a pair of resilient buttons 214 that is provided integrally with the collet 212. The buttons 214 are received by a pair of openings 216 in the housing 16 of the syringe adapter 210 to lock the collet 212 once the syringe adapter 210 is fully connected and in fluid communication with a mating connector, such as a patient connector 14. Pressing the buttons 214 will allow the mating connector to be disengaged and removed from the syringe adapter 210.

Referring to FIGS. 50A-51B, rather than providing the buttons 214 on the collet 212 as shown in FIGS. 48A-49B, an indirect button arrangement may be provided. In particular, the housing 16 of the syringe adapter 210 is provided with a pair of buttons 220 that are configured to be depressed inwardly into the interior space 22 of the syringe adapter 210. The collet 212 includes resilient button interface portions 222 that are configured to lock the collet 212 once the syringe adapter 210 is fully connected and in fluid communication with a mating connector, such as a patient connector 14. Pressing the buttons 220 will disengage the button interface portions 222 of the collet 212 and allow the mating connector to be disengaged and removed from the syringe adapter 210.

Figure 52:
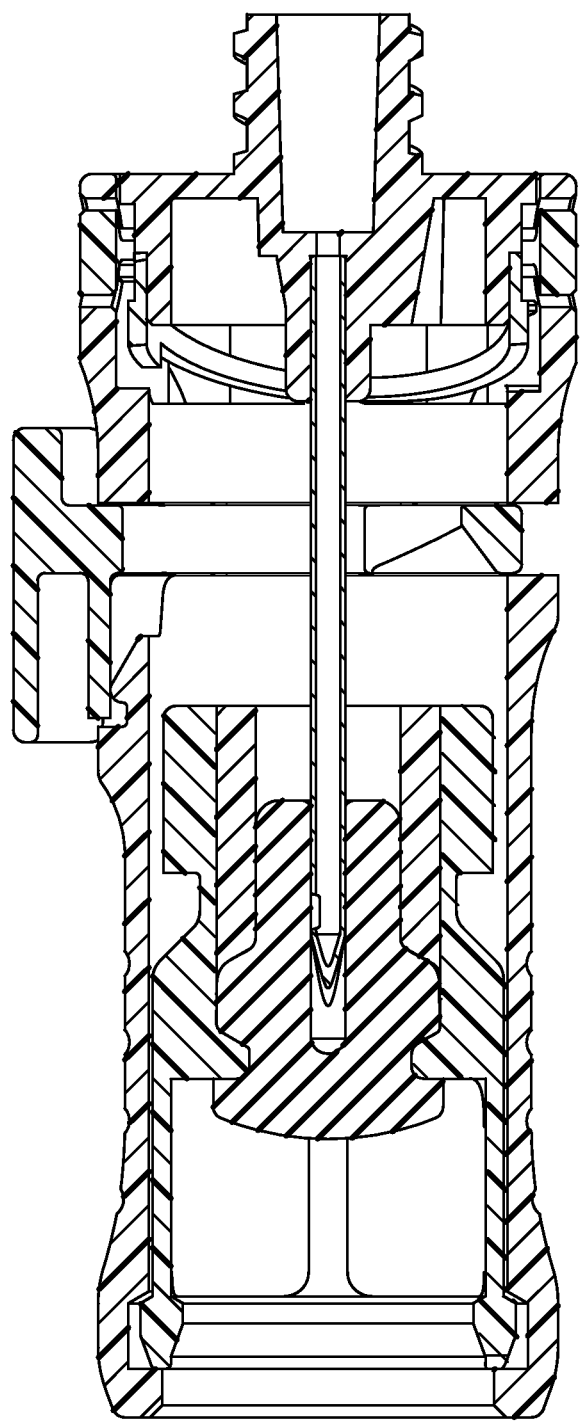
FIG. 52 is a cross-sectional view of a syringe adapter according to another aspect of the present invention.
Figure 53:
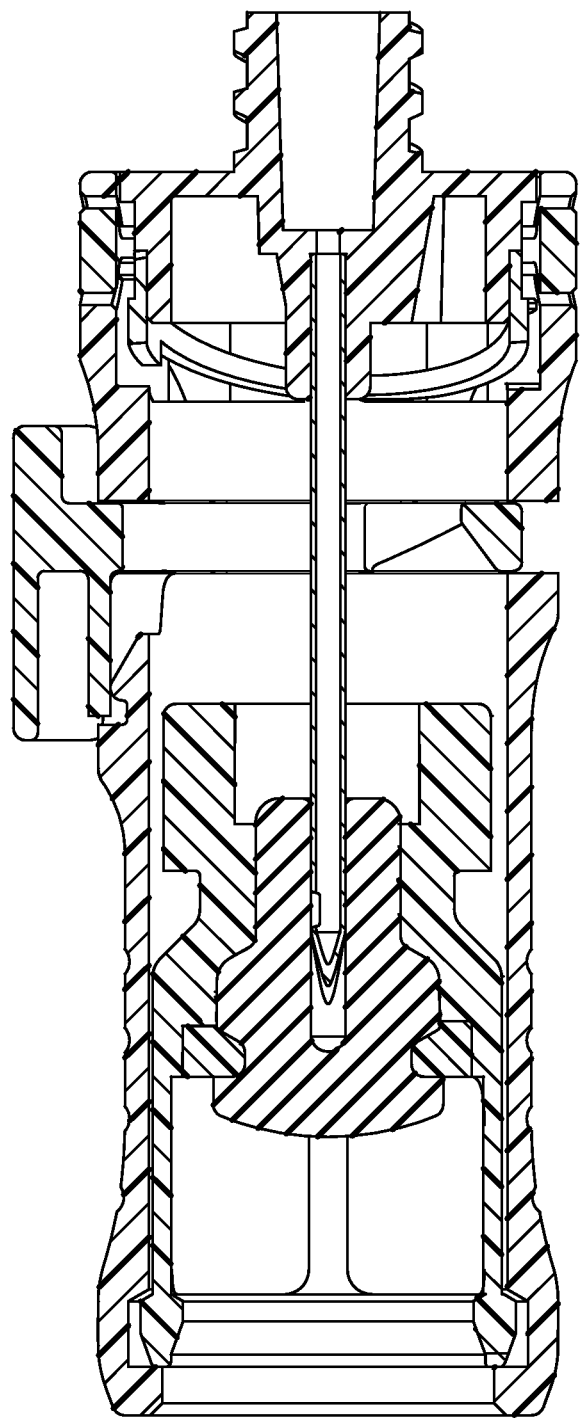
FIG. 53 is a cross-sectional view of a syringe adapter according to a further aspect of the present invention.
Figure 54:
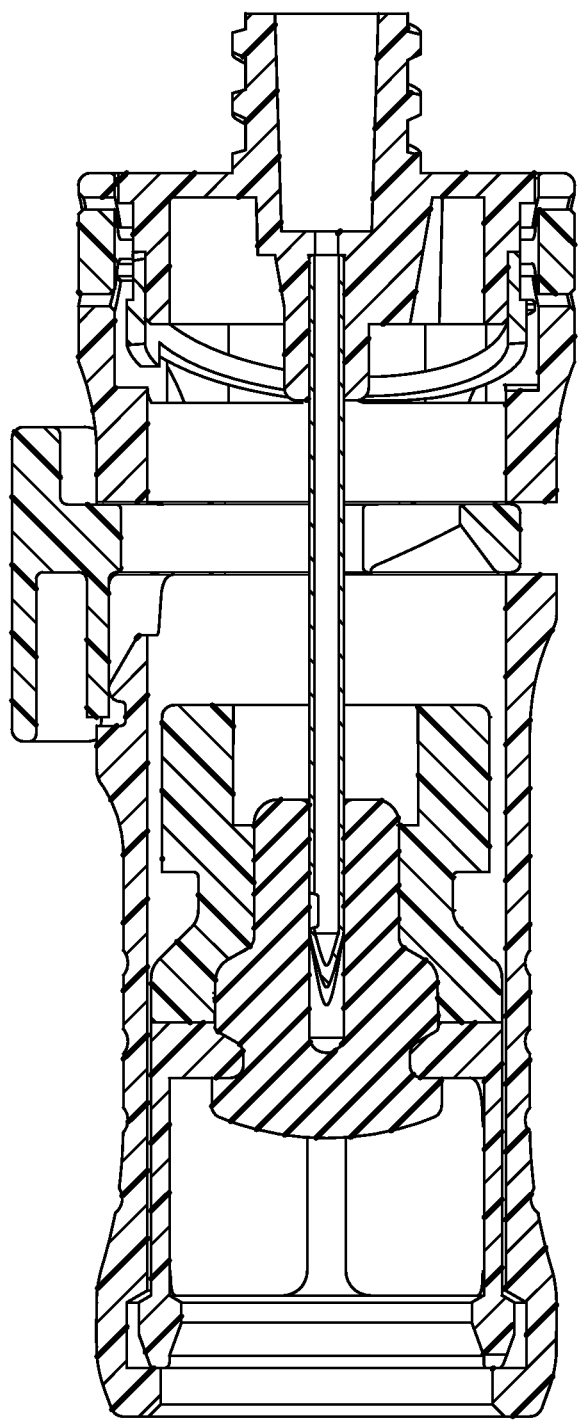
FIG. 54 is a cross-sectional view of a syringe adapter according to yet another aspect of the present invention.

Referring to FIGS. 52-54, further aspects of the collet 32 of FIGS. 9-11 are shown. In particular, rather than providing a collet that is formed as a unitary or single molded part, the collet 32 may be formed from one or more pieces that are secured to each other to form the collet 32. The multi-piece collet 32 aspects allow various membrane arrangements where the membrane can be installed prior to final assembly of the collet 32. The multiple pieces forming the collet 32 may be secured to each other via any suitable joining method, such ultrasonic welding, spin welding, or laser welding.

Figure 55A:
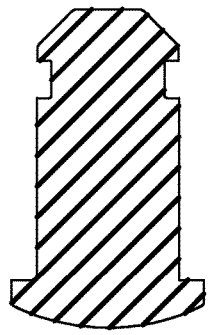
FIGS. 55A-55G are cross-sectional views of a first membrane according to various aspects of the present invention.
Figure 55B:
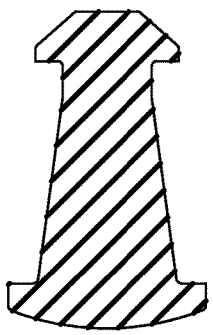
Figure 55C:
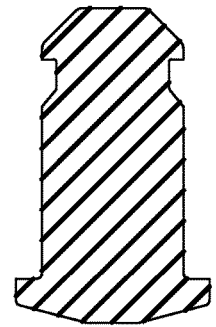
Figure 55D:
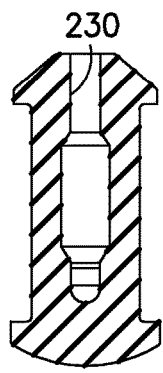
Figure 55E:
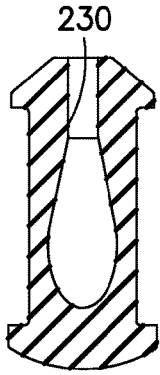
Figure 55F:
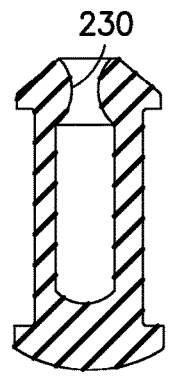
Figure 55G:
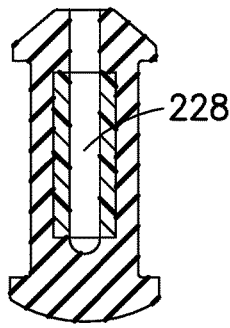
Figure 56A:
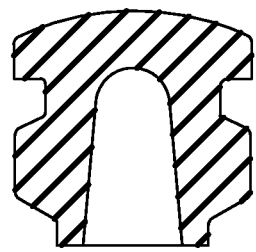
FIGS. 56A-56F are cross-sectional views of a second membrane according to various aspects of the present invention.
Figure 56B:
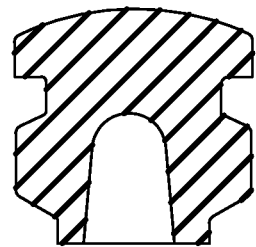
Figure 56C:
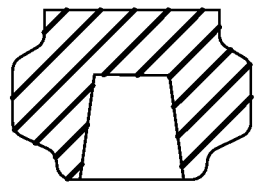
Figure 56D:
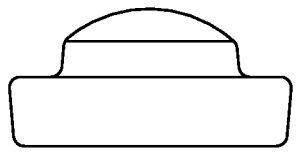
Figure 56E:
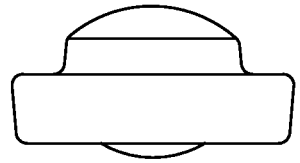
Figure 56F:
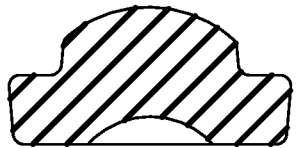
Figure 57:
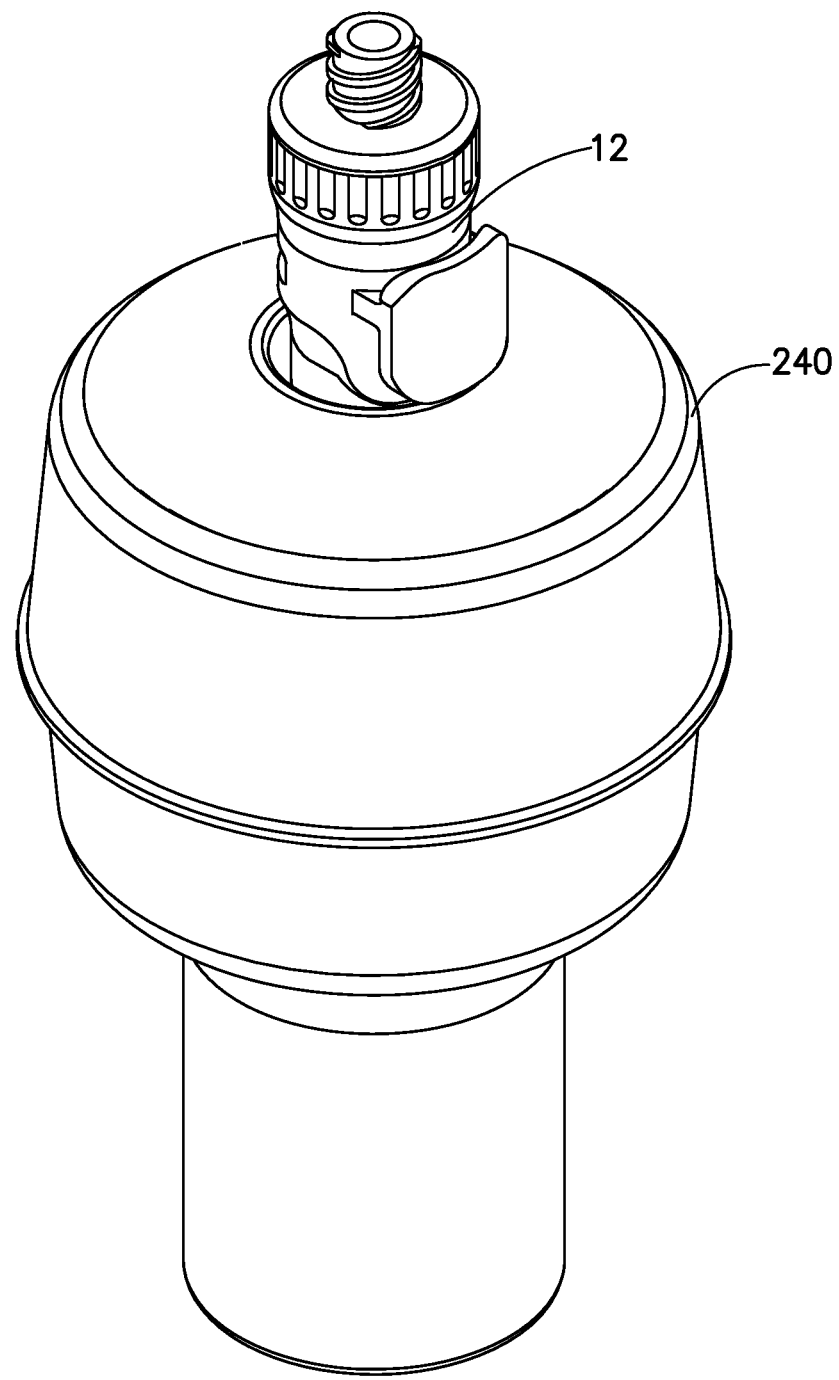
FIG. 57 is a perspective view of the syringe adapter of FIG. 2 showing the syringe adapter connected to a vial and a vial adapter in accordance with an aspect of the present invention.
Figure 58:
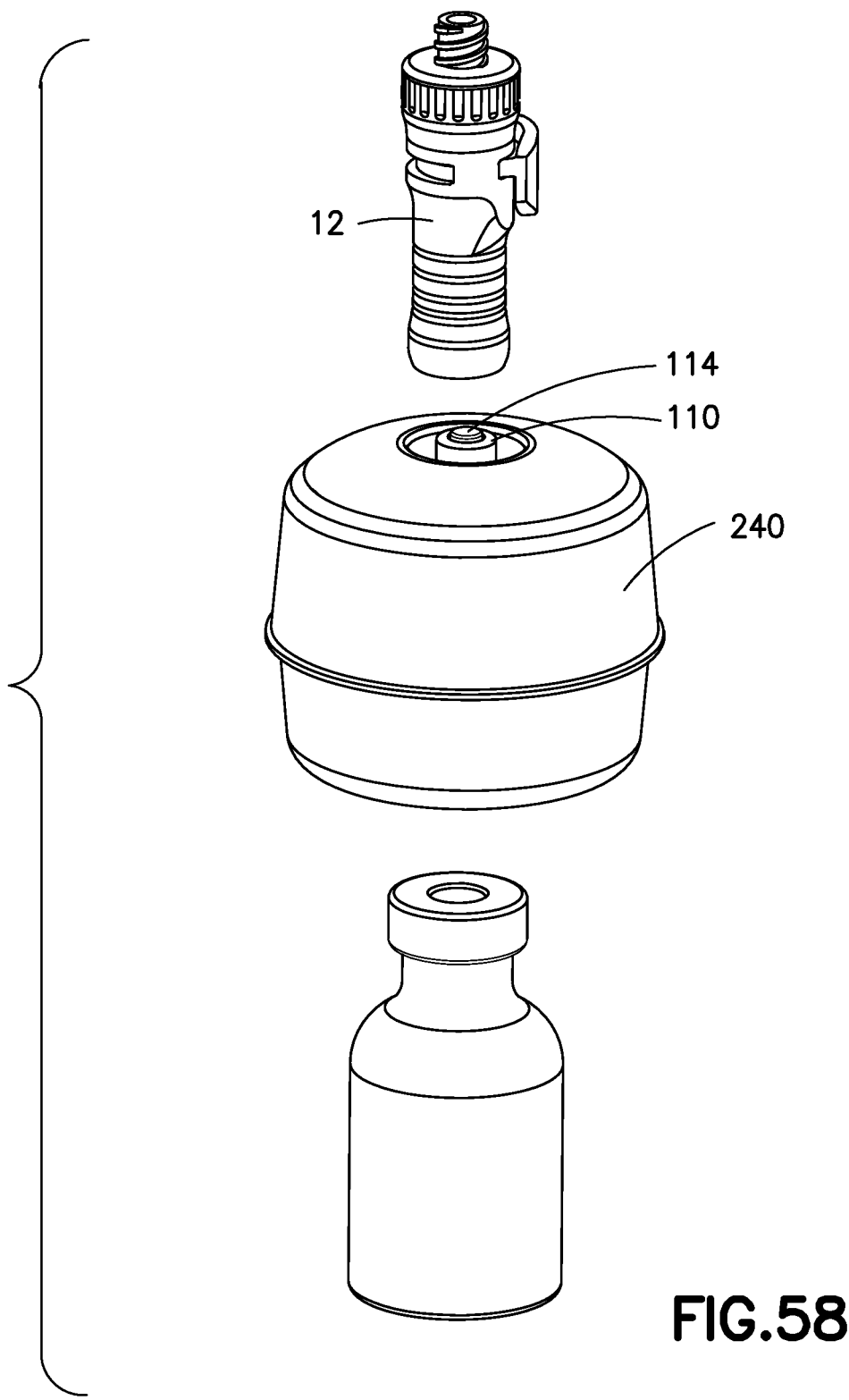
FIG. 58 is an exploded perspective view of the syringe adapter of FIG. 2 showing the syringe adapter along with a vial and a vial adapter according to one aspect of the present invention.
Figure 59:
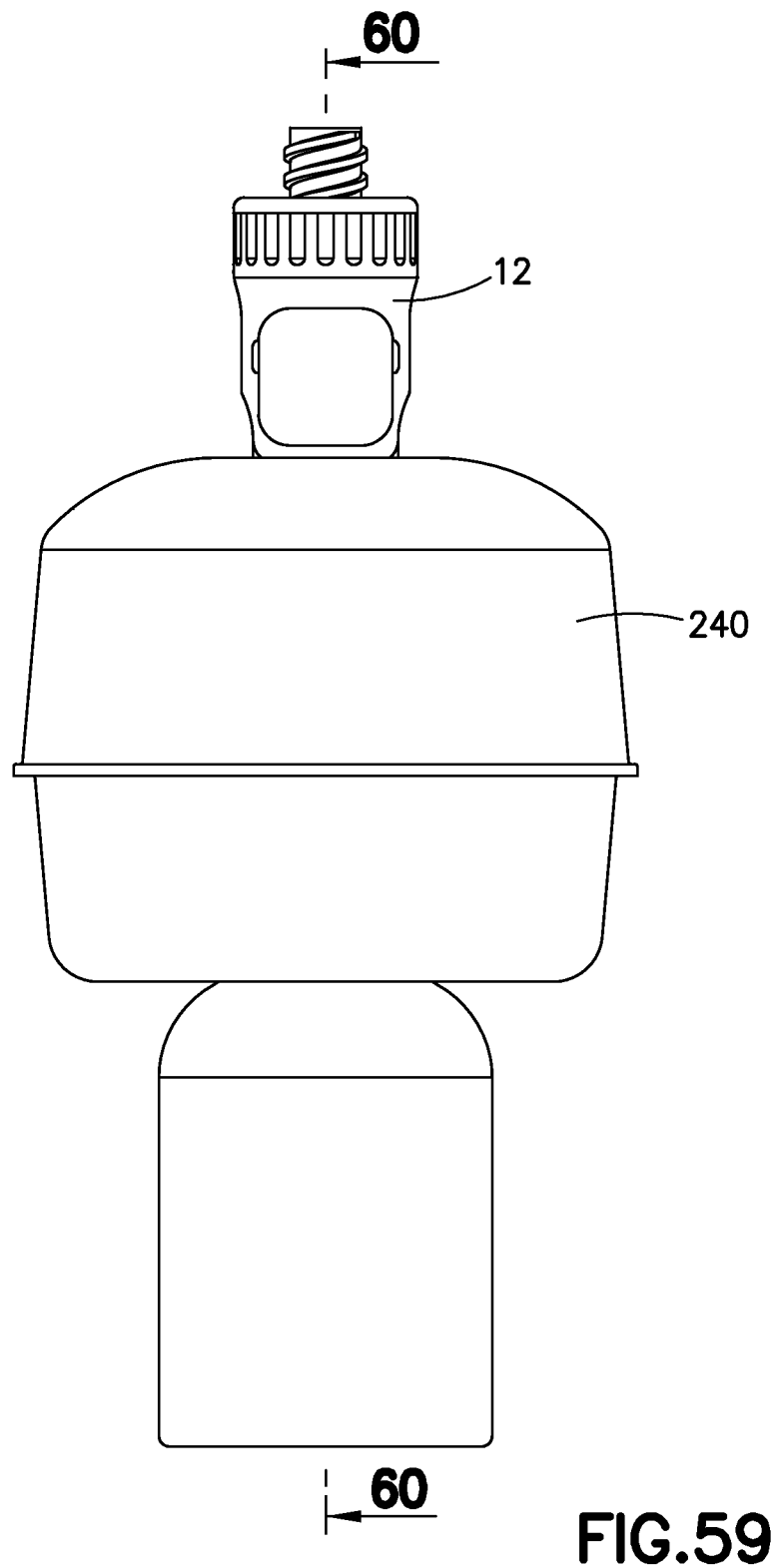
FIG. 59 is a front view of the syringe adapter of FIG. 2 showing the syringe adapter connected to a vial and a vial adapter according to one aspect of the present invention.

Referring to FIGS. 55A-55G, further aspects of the first membrane 34 are shown. In particular, various shapes, configuration, and cavities may be utilized for the first membrane. Further, as shown in FIG. 55G, the first membrane may include an insert 228 positioned within the first membrane 34. The geometries shown in FIGS. 55A-55G may be pushed or pulled into a mating component and retained without the need for secondary assembly processes or multi-piece housings. The aspects of the first membrane 34 shown in FIGS. 55D, 55E, and 55F include a sealing portion 230 at the top of the first membrane 34 to engage and seal an intermediate portion of the cannula 28 during use.

Referring to FIGS. 56A-56F, further aspects of the second membrane are shown. In particular, various shapes, configurations, and cavities may be utilized for the second membrane.

Figure 60:
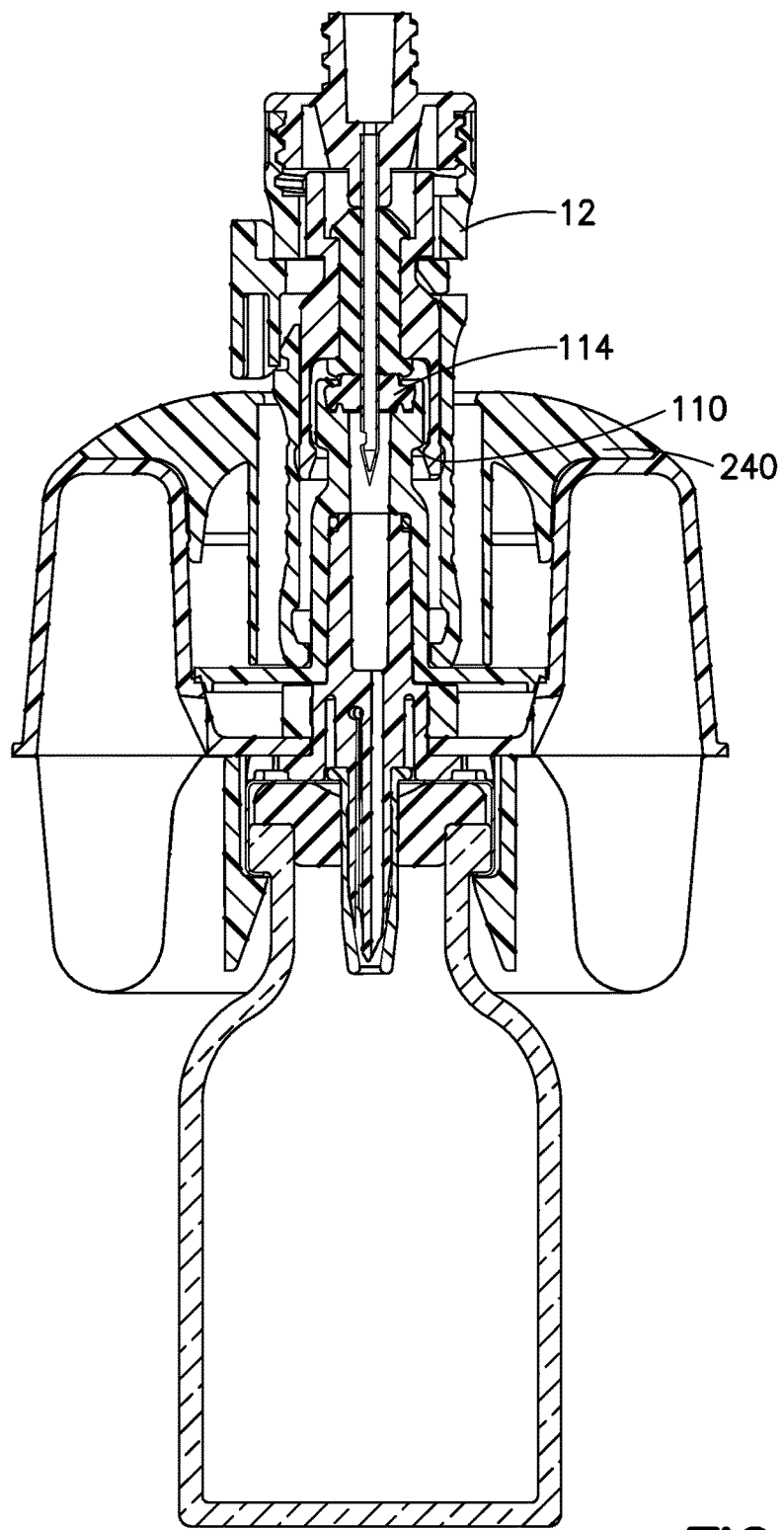
FIG. 60 is a cross-sectional view taken along line 60-60 in FIG. 59 showing the syringe adapter connected to a vial and a vial adapter according to one aspect of the present invention.

Referring to FIGS. 57-60, the syringe adapter 12 is shown engaged and in use with a vial adapter 240. As shown in FIG. 60, the vial adapter 240 includes the collet interface 110 and the second membrane 114, which is also provided on the patient connector 14. The syringe adapter 12 is connected to the vial adapter 240 in the same manner as the syringe adapter 12 is connected to the patient connector 14 as described above. The vial adapter 240 is secured to a vial and provides the collet interface 110 so that the syringe adapter 12 can be placed in fluid communication with the vial and also provides a pressure equalization arrangement to prevent fluids from escaping to the outside environment.

Figure 61:
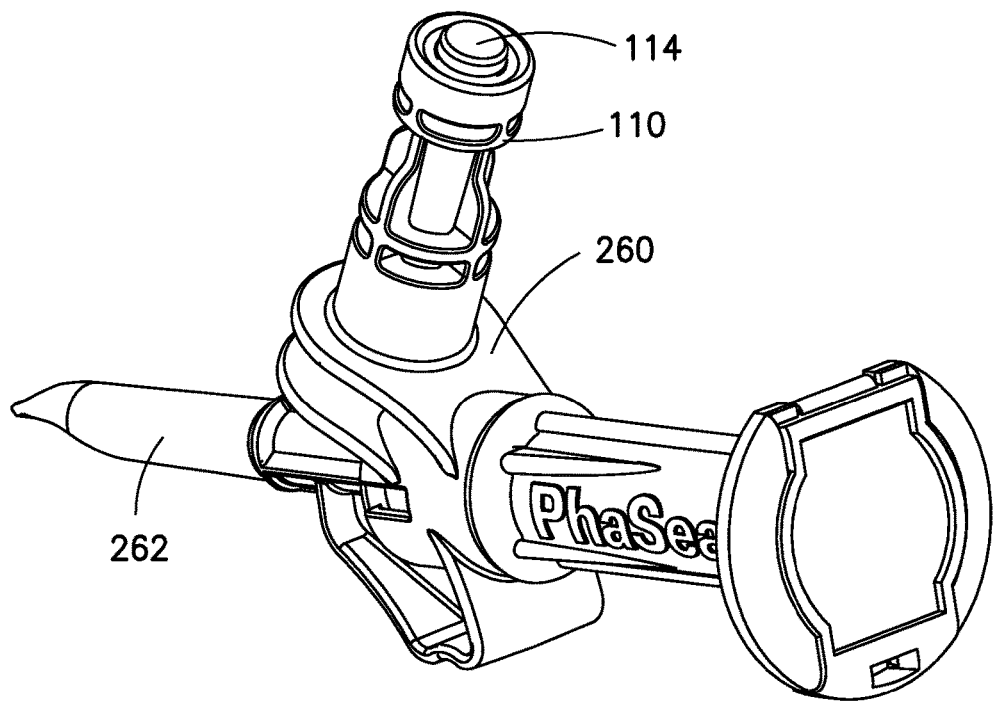
FIG. 61 is a perspective view of an IV bag adapter according to one aspect of the present invention.
Figure 62:
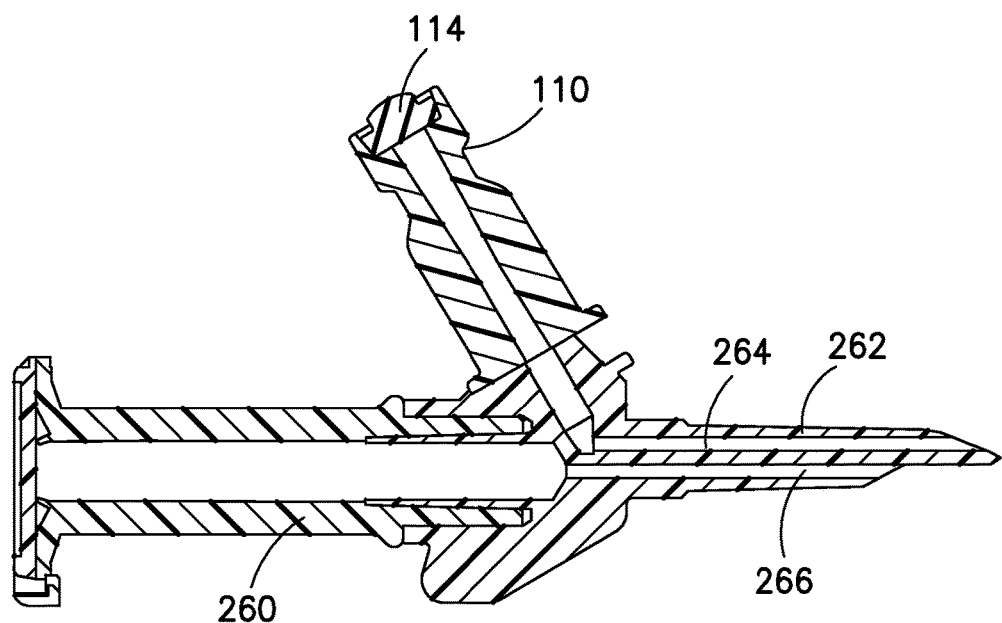
FIG. 62 is a cross-sectional view of the IV bag adapter of FIG. 61 according to one aspect of the present invention.

Referring to FIGS. 61 and 62, one aspect of an IV bag adapter 260 is shown. As noted above, the syringe adapter 12 can be connected to a variety of components typically utilized in closed system transfer device systems. The IV bag adapter 260 also includes the collet interface 110 and second membrane 114, which is also provided on the patient connector 14 and the vial adapter 240. The IV bag adapter 260 allows the syringe adapter 12 to be placed in fluid communication with an infusion or IV set and includes a spike member 262 having first and second channels 264, 266.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A syringe adapter comprising:
   a housing having a first end and a second end, the first end configured to be secured to a first container;
   a cannula having a first end and a second end, the second end of the cannula positioned within the housing; and
   a collet having a first end and a second end, at least a portion of the collet received within the housing, the collet comprising a body defining a passageway, a membrane received by the passageway, and a locking member connected to the body of the collet, the membrane comprising a body having a first end and a second end, at least a portion of the body of the membrane engaging the body of the collet, the body of the membrane defining a passageway extending from the first end of the membrane body towards the second end of the membrane body and terminating intermediate the first and second ends of the membrane body, the collet movable from a first position where the locking member is open to receive a mating connector to a second position where radially outward movement of the locking member is restricted,
   wherein when the collet is in the first position the second end of the cannula is positioned within the membrane passageway,
   wherein, during movement of the collet from the first position to the second position, the membrane is axially fixed to the collet relative to the locking member and the membrane slides relative to the cannula, and
   wherein, in the second position of the collet, the second end of the membrane body is pierced by the cannula and the collet is rotatable relative to the housing about a longitudinal axis of the housing.

2. The syringe adapter of claim 1, wherein the membrane includes a first head portion and a second head portion.

3. The syringe adapter of claim 2, wherein the first head portion of the membrane is positioned within the passageway of the collet, and wherein the second head portion is engaged with an end of the body of the collet.

4. The syringe adapter of claim 2, wherein the first head portion includes a frusto-conical surface.

5. The syringe adapter of claim 4, wherein the second head portion includes a convex surface.

6. The syringe adapter of claim 2, wherein the first end of the collet defines a counterbore, the first head portion of the membrane engaging the collet and positioned within the counterbore.

7. A system for closed transfer of fluids comprising:
a syringe adapter comprising; a housing having a first end and a second end, the first end configured to be secured to a first container; a cannula having a first end and a second end, the second end positioned within the housing; and a collet having a first end and a second end, at least a portion of the collet received within the housing, the collet comprising a body defining a passageway, a first membrane received by the passageway of the collet, and a locking member connected to the body of the collet, the first membrane comprising a body having a first end and a second end, at least a portion of the body of the first membrane engaging the body of the collet, the body of the first membrane defining a passageway extending from the first end of the first membrane body towards the second end of the first membrane body and terminating intermediate the first and second ends of the first membrane body, the collet movable from a first position where the locking member is open to receive a mating connector to a second position where radially outward movement of the locking member is restricted,
wherein, during movement of the collet from the first position to the second position, the first membrane is axially fixed to the collet relative to the locking member and the first membrane slides relative to the cannula, and
wherein, in the second position of the collet, the second end first membrane body is pierced by the cannula and the collet is rotatable relative to the housing about a longitudinal axis of the housing; and
the mating connector comprising a second membrane and a collet interface surface configured to receive and engage the locking member of the collet.

8. The system of claim 7, wherein the second membrane comprises a body having a first end and a second end, the first end of the body of the second membrane having a convex surface configured to engage the second end of the body of the first membrane.

9. The system of claim 7, wherein the second component includes a membrane seat that receives the second membrane.

10. The system of claim 7, wherein the passageway of the first membrane extends from the first end of the body of the first membrane towards the second end of the body of the first membrane.

11. The system of claim 10, wherein the passageway of the first membrane terminates at a position intermediate the first and second ends of the body of the first membrane.

12. The system of claim 10, wherein the first membrane includes a first head portion and a second head portion.

13. The system of claim 12, wherein the first head portion of the first membrane is positioned within the passageway of the collet, and wherein the second head portion of the first membrane is engaged with an end of the body of the collet.

14. The system of claim 12, wherein the first head portion of the first membrane includes a frusto-conical surface.

15. The system of claim 14, wherein the second head portion of the first membrane includes a convex surface.

16. The system of claim 12, wherein the first end of the collet defines a counterbore, the first head portion of the first membrane engaging the collet and positioned within the counterbore.

17. A syringe adapter comprising:
a housing having a first end and a second end, the first end configured to be secured to a first container;
a cannula having a first end and a second end, the second end of the cannula positioned within the housing; and
a collet having a first end and a second end, at least a portion of the collet received within the housing, the collet comprising a body defining a passageway, a membrane received by the passageway, and a locking member connected to the body of the collet,
wherein the membrane comprises a body having a first end and a second end, the body of the membrane including a first head portion and a second head portion, the first and second head portions extending radially outward from the body of the membrane and engaging the collet, the first head portion of the membrane including a frusto-conical surface, the second head portion of the membrane including a convex surface,
wherein the collet is movable from a first position where the locking member is open to receive a mating connector to a second position where radially outward movement of the locking member is restricted,
wherein, during movement of the collet from the first position to the second position, the membrane is axially fixed to the collet relative to the locking member and the membrane slides relative to the cannula, and
wherein, in the second position of the collet, the second end of the body of the membrane is pierced by the cannula and the collet is rotatable relative to the housing about a longitudinal axis of the housing.

18. The syringe adapter of claim 17, wherein the body of the membrane defines a passageway extending from the first end of the body of the membrane towards the second end of the body of the membrane.

19. The syringe adapter of claim 18, wherein the passageway terminates at a position intermediate the first and second ends of the body of the membrane.

* * * * *

UNITED STATES PATENT AND TRADEMARK OFFICE
CERTIFICATE OF CORRECTION

PATENT NO. : 10,376,654 B2  
APPLICATION NO. : 14/691922  
DATED : August 13, 2019  
INVENTOR(S) : Laurie Sanders et al.

Page 1 of 1

It is certified that error appears in the above-identified patent and that said Letters Patent is hereby corrected as shown below:

In the Claims

Column 15, Line 6, Claim 7, delete "comprising;" and insert -- comprising: --

Column 15, Line 33, Claim 7, after "end" insert -- of the --

Signed and Sealed this  
Twenty-second Day of October, 2019

Andrei Iancu  
*Director of the United States Patent and Trademark Office*